(12) United States Patent
Kikkawa et al.

(10) Patent No.: US 12,024,663 B2
(45) Date of Patent: *Jul. 2, 2024

(54) ONIUM SALT-CONTAINING TREATMENT LIQUID FOR SEMICONDUCTOR WAFERS

(71) Applicant: TOKUYAMA CORPORATION, Yamaguchi (JP)

(72) Inventors: Yuki Kikkawa, Yamaguchi (JP); Tomoaki Sato, Yamaguchi (JP); Takafumi Shimoda, Yamaguchi (JP); Takayuki Negishi, Yamaguchi (JP)

(73) Assignee: TOKUYAMA CORPORATION, Yamaguchi (JP)

( * ) Notice: Subject to any disclaimer, the term of this patent is extended or adjusted under 35 U.S.C. 154(b) by 257 days.

This patent is subject to a terminal disclaimer.

(21) Appl. No.: 17/419,058

(22) PCT Filed: Feb. 13, 2020

(86) PCT No.: PCT/JP2020/005663
§ 371 (c)(1),
(2) Date: Jun. 28, 2021

(87) PCT Pub. No.: WO2020/166677
PCT Pub. Date: Aug. 20, 2020

(65) Prior Publication Data
US 2022/0073820 A1 Mar. 10, 2022

(30) Foreign Application Priority Data

Feb. 13, 2019 (JP) .................................. 2019-024016
Mar. 13, 2019 (JP) .................................. 2019-045761
(Continued)

(51) Int. Cl.
*C09K 13/06* (2006.01)
*H01L 21/304* (2006.01)

(52) U.S. Cl.
CPC ............ *C09K 13/06* (2013.01); *H01L 21/304* (2013.01)

(58) Field of Classification Search
None
See application file for complete search history.

(56) References Cited

U.S. PATENT DOCUMENTS 5,670,011 A * 9/1997 Togawa .................. B24B 57/02
438/693
6,143,192 A 11/2000 Westmoreland
(Continued)

FOREIGN PATENT DOCUMENTS

EP    3 089 200        11/2016
JP    2001-234373      8/2001
(Continued)

OTHER PUBLICATIONS

Office Action issued Feb. 22, 2022 in corresponding Japanese Patent Application No. 2021-012388, with English translation.
(Continued)

*Primary Examiner* — Shamim Ahmed
(74) *Attorney, Agent, or Firm* — WENDEROTH, LIND & PONACK, L.L.P.

(57) ABSTRACT

Provided is a treatment liquid for a semiconductor wafer or the like used in a process for forming a semiconductor. Namely a treatment liquid containing (A) a hypochlorite ion, and (B) an alkylammonium salt expressed by the following Formula (1), or the like is provided.

(1)

(Continued)

(In the Formula, "a" is an integer from 6 to 20; $R^1$, $R^2$, and $R^3$ are independently, for example, an alkyl group with a carbon number from 1 to 20; and $X^-$ is, for example, a chloride ion.).

19 Claims, 2 Drawing Sheets

(30) Foreign Application Priority Data

May 16, 2019 (JP) ................................. 2019-093194
Jun. 14, 2019 (JP) ................................. 2019-110984

(56) References Cited

U.S. PATENT DOCUMENTS

| | | | |
|---|---|---|---|
| 2001/0023701 A1 | 9/2001 | Aoki et al. | |
| 2002/0060202 A1* | 5/2002 | Fukunaga | H01L 21/6708 |
| | | | 257/E21.309 |
| 2002/0123235 A1* | 9/2002 | Kraus | C09K 13/00 |
| | | | 257/E21.309 |
| 2003/0017419 A1 | 1/2003 | Futase et al. | |
| 2003/0132103 A1 | 7/2003 | Kobata et al. | |
| 2006/0226122 A1 | 10/2006 | Wojtczak et al. | |
| 2008/0121839 A1 | 5/2008 | Park et al. | |
| 2008/0299350 A1* | 12/2008 | Mezaki | B24B 37/0056 |
| | | | 451/36 |
| 2009/0035942 A1 | 2/2009 | White et al. | |
| 2009/0124082 A1 | 5/2009 | Park et al. | |
| 2010/0221417 A1* | 9/2010 | Miyamoto | C11D 1/75 |
| | | | 427/129 |
| 2012/0256122 A1 | 10/2012 | Sato et al. | |
| 2016/0032186 A1 | 2/2016 | Chen et al. | |
| 2017/0222138 A1 | 8/2017 | Park et al. | |
| 2018/0087006 A1 | 3/2018 | Oie et al. | |
| 2018/0138053 A1 | 5/2018 | Yao et al. | |
| 2018/0291309 A1 | 10/2018 | Frye et al. | |

FOREIGN PATENT DOCUMENTS

| | | |
|---|---|---|
| JP | 2002-161381 | 6/2002 |
| JP | 2003-324091 | 11/2003 |
| JP | 2008-135746 | 6/2008 |
| JP | 2008-536312 | 9/2008 |
| JP | 2009-16854 | 1/2009 |
| JP | 5314019 | 10/2013 |
| JP | 2016-510175 | 4/2016 |
| JP | 2017-28257 | 2/2017 |
| JP | 2020-87945 | 6/2020 |
| WO | 2008/129891 | 10/2008 |
| WO | 2011/074601 | 6/2011 |
| WO | 2016/068183 | 5/2016 |
| WO | 2016/140246 | 9/2016 |
| WO | 2016/167184 | 10/2016 |
| WO | 2020/123126 | 6/2020 |

OTHER PUBLICATIONS

International Search Report (ISR) issued Apr. 28, 2020 in International (PCT) Application No. PCT/JP2020/005663.
Partial Supplementary European Search Report issued Sep. 19, 2022 in corresponding European Patent Application No. 20756178.8.
Extended European Search Report issued Dec. 9, 2022 in European Patent Application No. 20756178.8.
Office Action issued Dec. 19, 2023 in Japanese Patent Application No. 2020-572319, with English-language translation.

* cited by examiner

ONIUM SALT-CONTAINING TREATMENT LIQUID FOR SEMICONDUCTOR WAFERS

TECHNICAL FIELD

The present invention relates to a novel treatment liquid for etching metallic ruthenium present on a semiconductor wafer to be used in a manufacturing process of a semiconductor element.

BACKGROUND ART

In recent years, microfabrication design has been promoted for the design rule for semiconductor elements, and thus the wiring resistance tends to increase. As a result of the increase in wiring resistance, the high-speed operation of a semiconductor element is markedly impaired, thus making it necessary to take countermeasures. In view of this, a desired wiring material is a wiring material having more solid electromigration resistance and a lower electric resistance value than conventional wiring materials.

Ruthenium has higher electromigration resistance than aluminum and copper which are conventional wiring materials, and ruthenium can decrease the electric resistance value of the wiring, thus attracting attention particularly as a wiring material for which the design rule for semiconductor elements is 10 nm or less. Not only in cases where ruthenium is used as a wiring material but also in cases where copper is used as a wiring material, ruthenium can prevent electromigration, and thus, using ruthenium as a barrier metal for copper wiring is under study.

In cases where ruthenium is selected as a wiring material in a wiring formation step of a semiconductor element, the wiring is formed by dry or wet etching in the same manner as in cases where a conventional wiring material is used. However, since it is difficult to remove ruthenium by dry etching with an etching gas, or by CMP polishing, more precise etching is desired, and specifically, wet etching is attracting attention.

Therefore, when ruthenium is used as a wiring material or a barrier metal, precise microprocessing of ruthenium by wet etching is required. In order to carry out precise ruthenium microprocessing, accurate control of the etching rate on ruthenium is required. Furthermore, in order to realize multilayer wiring, the flatness of each ruthenium layer is essential, and the flatness of the ruthenium surface after etching is also desired.

In Patent Document 1, as an etching method for a ruthenium film, a method for etching a ruthenium film using a chemical liquid having a pH of 12 or more and an oxidation-reduction potential of 300 mV vs SHE or more, specifically a solution of a halogen oxoate, such as hypochlorite, chlorite, and bromate, is presented. However, what Patent Document 1 discloses is a chemical liquid that is for surely removing an adhered ruthenium by etching, and is designed for removing ruthenium.

Meanwhile, Patent Document 2 proposes a method for oxidizing ruthenium thereby dissolving and removing the ruthenium by using an aqueous solution of pH 11 or higher containing orthoperiodic acid. Furthermore, Patent Document 3 proposes an etching liquid for ruthenium metal having a pH of 10 or more and less than 12 containing a bromine-containing compound, an oxidizing agent, a basic compound, and water.

In addition, Patent Document 4 proposes a cleaning method in which ruthenium is oxidized, thereby dissolved, and removed using a removal solution containing cerium (IV) ammonium nitrate and additionally a strong acid such as nitric acid.

Meanwhile, in cases where ruthenium is subjected to wet etching under alkaline conditions, ruthenium is dissolved, for example, in the form of $RuO_4^-$ or $RuO_4^{2-}$ in a treatment liquid. $RuO_4^-$ or $RuO_4^{2-}$ is changed to $RuO_4$ in a treatment liquid, and part of the same is gasified and released into a gas phase. $RuO_4$ is strongly oxidative, and thus, not only is harmful to the human body but also is easily reduced to generate $RuO_2$ particles. In general, particles cause a decrease in the yield rate, which constitutes a serious problem in semiconductor formation steps. Against such a background, it is very important to inhibit the generation of a $RuO_4$ gas.

Patent Document 5 describes a chemical liquid having a pH of 12 or higher and an oxidation-reduction potential of 300 mV vs. SHE or higher as an etching liquid for a ruthenium film. In addition, a method for etching a ruthenium film using a solution of a halogen oxoate, such as hypochlorite, chlorite, and bromate, is disclosed.

Patent Document 6 proposes a method of oxidizing, thereby dissolving, and removing ruthenium by using an aqueous solution containing orthoperiodic acid having a pH of 11 or higher.

Patent Document 7 describes a CMP slurry containing a ruthenium-coordinated nitrogen oxide ligand (N—O ligand) that does not generate a $RuO_4$ gas in chemical mechanical polishing (CMP) of ruthenium.

CITATION LIST

Patent Document

Patent Document 1: Japanese Patent Laid-Open No. 2002-161381
Patent Document 2: International Publication No. WO2016/068183
Patent Document 3: International Publication No. WO2011/074601
Patent Document 4: Japanese Patent Laid-Open No. 2001-234373
Patent Document 5: Japanese Patent Laid-Open No. 2002-161381
Patent Document 6: International Publication No. WO2016/068183
Patent Document 7: Japanese Patent No. 5314019

SUMMARY OF INVENTION

Technical Problem

However, based on the study by the present inventors, it has been found that there is room for improvement with respect to the conventional etching liquids described in the cited documents 1 to 4 because of the following.

For example, the method for etching ruthenium described in Patent Document 1 or 4 is intended to remove a ruthenium residue adhered to the back surface or bevels of a semiconductor substrate, and is capable of dissolving and removing ruthenium. However, with the etching liquid described in Patent Document 1 or 4, it was difficult to maintain the desired flatness of the ruthenium surface after the etching treatment in the wiring step. Therefore, it was difficult to use the etching liquid according to Patent Document 1 or 4 as that for ruthenium in the step of forming the wiring of a semiconductor element.

Further, the etching liquid described in Patent Document 2 was an etching liquid targeting an etching residue containing ruthenium similarly as in Patent Document 1, and since it was difficult to maintain the flatness of the ruthenium surface after the etching treatment, the same could hardly be used in the step of forming the wiring.

In addition, with respect to the etching liquid described in Patent Document 3, it is described that ruthenium used in the manufacturing process of a semiconductor element, wiring, and a barrier metal which are constructed on a substrate such as a semiconductor wafer is etched with the same. However, since its purpose is for cleaning the back surface and bevels of a substrate such as a semiconductor wafer similarly to Patent Document 1 and Patent Document 4, and when ruthenium was etched with an etching liquid described in Patent Document 3, the flatness of the ruthenium surface was not maintained after the etching treatment, and there was room for further improvement.

Therefore, the first object of the present invention is to provide a treatment liquid that can wet-etch ruthenium present on a semiconductor wafer. Another object is to provide a treatment liquid that can maintain the flatness of the ruthenium surface after the etching treatment.

Through the investigations by the inventors, it was found that the conventional treatment liquids described in the cited documents 5 to 7 were still in need for improvement in the following points.

For example, the method of etching ruthenium described in Patent Document 5 is intended to remove ruthenium residues adhered to the back surface or bevels of a semiconductor substrate, and it is possible to dissolve and remove ruthenium. However, Patent Document 5 does not mention anything about the inhibition of a $RuO_4$ gas, and in fact, the method described in Patent Document 5 lacked stability, and was not able to inhibit generation of a $RuO_4$ gas, and a large amount of $RuO_4$ gas was generated. There was also a problem in that a large amount of $RuO_2$ (particles) was generated.

In addition, Patent Document 6 discloses a ruthenium removal composition containing orthoperiodic acid, which can etch an etching residue containing ruthenium. However, Patent Document 6 does not mention anything about the inhibition of a $RuO_4$ gas, and a $RuO_4$ gas generated during the etching treatment could not be inhibited.

Further, Patent Document 7 shows that it is possible to inhibit a toxic $RuO_4$ gas by using a CMP slurry containing a ruthenium-coordinated nitrogen oxide ligand (N—O ligand) in performing CMP. However, since the CMP slurry shown in Patent Document 7 is acidic, it is difficult to inhibit a $RuO_4$ gas by the CMP slurry composition shown in Patent Document 7 under alkaline conditions where the dissolution mechanism of ruthenium is different. In fact, when the ruthenium-coordinated nitrogen oxide ligand described in Patent Document 7 was added to an alkaline ruthenium etching liquid containing hypochlorous acid, a $RuO_4$ gas was generated to confirm that there was no $RuO_4$ gas inhibitory effect.

Therefore, the second object of the present invention is to provide a treatment liquid for a semiconductor wafer that can inhibit $RuO_4$ gas generation when a semiconductor wafer containing ruthenium is brought into contact with the treatment liquid under alkaline conditions.

Solution to Problem

The present inventors diligently conducted investigations to achieve the first object above. For this purpose, the effect of addition of a specific alkylammonium salt to a treatment liquid containing hypochlorite ions was examined. Since the flatness of the ruthenium surface after the etching treatment could not be maintained with the treatment liquid containing only hypochlorite ions, various additive ingredients were combined. As a result, it was found that it became possible to maintain the flatness of the ruthenium surface after the etching treatment by adding a specific alkylammonium salt, thereby completing the first invention.

In addition, the present inventors diligently conducted investigations to achieve the above second object. Namely, addition of a variety of onium salts to a treatment liquid for semiconductor wafers containing ruthenium was investigated. Since it was not possible to inhibit a $RuO_4$ gas merely by using a treatment liquid for semiconductor wafers containing ruthenium, various additive ingredients were combined. As a result, it was found that the $RuO_4$ gas generation could be inhibited by adding a specific onium salt, thereby completing the second invention.

A first aspect of the present invention for achieving the first object described above includes the following (1) to (7).

(1) A treatment liquid for etching a metal contained in a semiconductor wafer, wherein the treatment liquid is used in a process for forming the semiconductor and comprising:
(A) a hypochlorite ion
(B) an alkylammonium salt expressed by the following Formula (1).

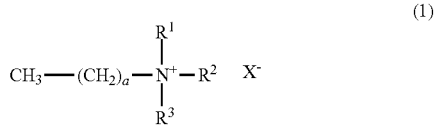

(In the Formula, "a" is an integer from 6 to 20; and $R^1$, $R^2$, and $R^3$ are a hydrogen atom, or an alkyl group with a carbon number from 1 to 20. X− is a fluoride ion, a chloride ion, an iodide ion, a hydroxide ion, a nitrate ion, a phosphate ion, a sulfate ion, a hydrogen sulfate ion, a methanesulfate ion, a perchlorate ion, an acetate ion, a fluoroborate ion, or a trifluoroacetate ion.)

As the mechanism by which the treatment liquid of the first aspect of the present invention maintains the flatness of the ruthenium surface after the etching treatment, the following is conceivable. That is, alkylammonium ions of the alkylammonium salt contained in the treatment liquid adhere to the surface of ruthenium, which is the etching target, and form a protective layer. The protective layer formed from alkylammonium ions prevents a contact with hypochlorite ions, which oxidize and dissolve ruthenium, so that the flatness of the ruthenium surface after the etching treatment can be conceivably better maintained compared to an etching treatment with a treatment liquid containing solely hypochlorite ions.

According to the first aspect of the present invention, the following embodiment is also possible. For inhibiting the ruthenium surface from roughening through the etching treatment, (2) it is preferable to formulate the treatment liquid according to (1), wherein the concentration of the alkylammonium salt (B) expressed by Formula (1) is from 0.0001 to 10 mass %.

Furthermore, in order to accelerate the etching rate of ruthenium, (3) it is preferable to formulate the treatment liquid according to (1) or (2), wherein the concentration of the hypochlorite ion (A) is from 0.05 to 20.0 mass %.

Further, in order to reduce impurities such as sodium to be contained in a treatment liquid, (4) it is preferable to formulate the treatment liquid according to any one of (1) to (3) comprising at least one kind of ammonium ion (C) selected from a tetramethylammonium ion, a tetraethylammonium ion, a tetrapropylammonium ion, and a tetrabutylammonium ion.

Similarly, in order to secure both inhibition of roughened surface of ruthenium after the etching treatment and a satisfactory etching rate of ruthenium, (5) it is preferable to formulate the treatment liquid according to any one of (1) to (4), wherein the pH at 25° C. is greater than 7 and less than 14.0.

Furthermore, (6) it is also possible to provide the treatment liquid according to any one of (1) to (5), wherein the metal contained in the semiconductor wafer is ruthenium.

Further, (7) it is also possible to provide an etching method comprising a step of bringing the semiconductor wafer into contact with the treatment liquid according to any one of (1) to (6).

Next, a second aspect of the present invention for achieving the second object described above includes the following (8) to (23):

(8) a treatment liquid for a semiconductor wafer, comprising an onium salt consisting of an onium ion and an anion, wherein the onium salt is a quaternary onium salt expressed by Formula (2), or a tertiary onium salt expressed by Formula (3).

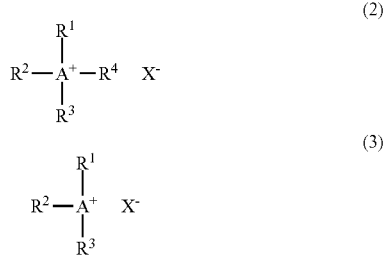

(In Formula (2), $A^+$ is an ammonium ion, or a phosphonium ion; and $R^1$, $R^2$, $R^3$, and $R^4$ are independently an alkyl group with a carbon number from 1 to 25, an allyl group, an aralkyl group having an alkyl group with a carbon number from 1 to 25, or an aryl group. When $R^1$, $R^2$, $R^3$, and $R^4$ are alkyl groups, at least one of the alkyl groups in $R^1$, $R^2$, $R^3$, and $R^4$ has a carbon number of 2 or more. At least one hydrogen in a ring of an aryl group in the aralkyl group, and the aryl group may be replaced with fluorine, chlorine, an alkyl group with a carbon number from 1 to 10, an alkenyl group with a carbon number from 2 to 10, an alkoxy group with a carbon number from 1 to 9, or an alkenyloxy group with a carbon number from 2 to 9; and in these groups, at least one hydrogen may be replaced with fluorine or chlorine. In Formula (3), $A^+$ is a sulfonium ion; and $R^1$, $R^2$, and $R^3$ are independently an alkyl group with a carbon number from 1 to 25, an allyl group, an aralkyl group having an alkyl group with a carbon number from 1 to 25, or an aryl group. When $R^1$, $R^2$, and $R^3$ are alkyl groups, at least one of the alkyl groups in $R^1$, $R^2$, and $R^3$ has a carbon number of 2 or more. At least one hydrogen in a ring of an aryl group in the aralkyl group, or the aryl group may be replaced with fluorine, chlorine, an alkyl group with a carbon number from 1 to 10, an alkenyl group with a carbon number from 2 to 10, an alkoxy group with a carbon number from 1 to 9, or an alkenyloxy group with a carbon number from 2 to 9; and in these groups, at least one hydrogen may be replaced with fluorine or chlorine. In Formula (2) or (3), $X^-$ is a fluoride ion, a chloride ion, an iodide ion, a hydroxide ion, a nitrate ion, a phosphate ion, a sulfate ion, a hydrogen sulfate ion, a methanesulfate ion, a perchlorate ion, a chlorate ion, a chlorite ion, a hypochlorite ion, an orthoperiodate ion, a metaperiodate ion, an iodate ion, an iodite ion, a hypoiodite ion, an acetate ion, a carbonate ion, a hydrogencarbonate ion, a fluoroborate ion, or a trifluoroacetate ion.)

As the mechanism by which the treatment liquid of the second aspect of the present invention inhibits $RuO_4$ gas generation, the following is conceivable. That is, in an alkaline treatment liquid, anions such as $RuO_4^-$ and $RuO_4^{2-}$ generated by dissolution of ruthenium (hereinafter occasionally referred to as $RuO_4^-$, etc.) electrostatically interact with the onium ions contained in the treatment liquid, and part of them come to exist stably as ion pairs. This prevents the change from $RuO_4^-$ etc. to $RuO_4$, and as a result, $RuO_4$ gas generation is inhibited. In addition, since formation of $RuO_4$ is prevented, it is presumed that generation of $RuO_2$ particles caused by reduction of $RuO_4$ is also inhibited.

Therefore, the $RuO_4$ gas inhibitory effect by addition of the onium salt in the treatment liquid of the second aspect of the present invention is not limited to the type or amount of an oxidizing agent or other additives that can be included in the treatment liquid, the treatment method, or the treatment condition. For example, as an oxidizing agent that can be included in the treatment liquid of the second aspect, it can be utilized any publicly known oxidizing agents used as an oxidizing agent in a treatment liquid for a semiconductor. For example, a halogen oxyacid, permanganic acid, and their salts or ions, hydrogen peroxide, ozone, a cerium (IV) salt, etc. can be suitably used. When the treatment liquid of the second aspect of the present invention contains such an oxidizing agent, it can exhibit the $RuO_4$ gas inhibitory effect owing to the onium salt contained in the treatment liquid. Further, the treatment method for a semiconductor wafer with the treatment liquid of the second aspect of the present invention is not limited to wet etching, but can also be suitably used as a treatment liquid for cleaning applications or residue removal applications. Furthermore, when the treatment liquid of the second aspect of the present invention is used for CMP polishing, $RuO_4$ gas generation can also be inhibited in the CMP polishing step. The treatment of a wafer containing ruthenium with the treatment liquid of the second aspect of the present invention can be performed by a single wafer treatment, or an immersion treatment. The temperature of the treatment liquid is not particularly restricted, and at any treatment temperature, the inhibitory effect on $RuO_4$ gas generation can be obtained owing to the onium salt contained in the treatment liquid.

Further, for the sake of stronger inhibition of $RuO_4$ gas generation by increasing the reactivity of $RuO_4^-$, etc. with the onium salt, the following is preferable, that is:

(9) it is preferable to formulate the treatment liquid according to (8) wherein the quaternary onium salt is an ammonium salt.

(10) it is preferable to formulate the treatment liquid according to (8) or (9), wherein the quaternary onium salt is a tetraalkylammonium salt.

(11) it is preferable to formulate the treatment liquid according to any one of (8) to (10), wherein the quaternary onium salt is a salt composed of at least one ammonium ion selected from a tetrapropylammonium ion, a tetrabutylammonium ion, or a tetrapentylammonium ion.

In addition, in order to further inhibit a $RuO_4$ gas by increasing the addition amount of the onium salt,

(12) it is preferable to formulate the treatment liquid according to any one of (8) to (11), wherein the concentration of the onium salt in the treatment liquid is from 0.0001 to 50 mass %.

In addition, in order to inhibit generation of $RuO_2$ particles, and to further inhibit $RuO_4$ gas generation,

(13) it is preferable to formulate the treatment liquid according to (8) to (12), wherein the treatment liquid comprises an oxidizing agent.

Further, in order to achieve both satisfactory processing speed of a ruthenium-containing wafer and inhibition of $RuO_4$ gas,

(14) it is preferable to formulate the treatment liquid according to any one of (8) to (13), wherein the treatment liquid comprises a hypochlorite ion and the concentration of the hypochlorite ion is from 0.05 to 20.0 mass %.

As described above, in the second aspect of the present invention, $RuO_4^-$ etc. generated by dissolution of ruthenium are trapped by the onium salt contained in the treatment liquid, thereby inhibiting $RuO_4$ gas generation. In this case, $RuO_4^-$ etc. and onium ions are dissolved in the treatment liquid in the form of ion pairs, however when the solubility is exceeded, precipitates are formed. Since the precipitates become particles in the semiconductor formation process and cause decrease in the yield rate. Therefore, in order to dissolve the precipitates, it is necessary to increase the solubility, for which addition of an organic solvent is an effective method. Therefore, in the second aspect of the present invention the following embodiment is desirable. In other words, the treatment liquid is preferably:

(15) the treatment liquid according to any one of (8) to (14), further comprising an organic solvent.

When the precipitates dissolve into the treatment liquid, they may exist in the treatment liquid as ion pairs (in a state where the electrical interaction between $RuO_4^-$, etc. and onium ions is maintained), or exist independently as the respective ions, for which the interaction between $RuO_4^-$, etc. and onium ions has been lost. In the former case, $RuO_4^-$, etc. are trapped by the onium ion, and a $RuO_4$ gas is not generated, but in the latter case, $RuO_4^-$, etc. change to $RuO_4$ and a $RuO_4$ gas is generated. In the above, the difference between the former and the latter cases ascribes to the relative dielectric constant of the organic solvent to be added. Since, generally, when the relative dielectric constant of the solvent is lower, they are likely to exist as ion pairs, by adding an organic solvent with a low relative dielectric constant, it becomes possible to inhibit $RuO_4$ gas generation.

Namely,

(16) it is preferable to formulate the treatment liquid according to (15), wherein the relative dielectric constant of the organic solvent is 45 or less.

Furthermore, when the treatment liquid contains a strong oxidizing agent, an organic solvent to be added should preferably not react with the treatment liquid. Consequently,

(17) it is preferable to formulate the treatment liquid according to (15) or (16), wherein the organic solvent is a sulfolane, an alkyl nitrile, a halogenated alkane, or an ether.

Furthermore, in order to sufficiently dissolve the formed precipitates,

(18) it is preferable to formulate the treatment liquid according to any one of (15) to (17), wherein the concentration of the organic solvent in the treatment liquid is 0.1 mass % or more.

In order to maintain the processing speed of a ruthenium-containing wafer and the storage stability, while inhibiting $RuO_4$ gas generation

(19) it is preferable to formulate the treatment liquid according to any one of (8) to (18), wherein the pH at 25° C. is 7 or more and 14 or less.

Furthermore,

(20) the treatment liquid according to any one of (8) to (19) to be used for etching a semiconductor wafer containing ruthenium can be provided.

Also,

(21) use of the treatment liquid according to any one of (8) to (19) for etching a semiconductor wafer containing ruthenium can be provided.

Further,

(22) a method for etching a semiconductor wafer, comprising a step of bringing a semiconductor wafer containing ruthenium into contact with the treatment liquid according to any one of (8) to (19) can be provided.

Further,

(23) An inhibitor for ruthenium-containing gas generation comprising an onium salt consisting of an onium ion and an anion, wherein the onium salt is a quaternary onium salt expressed by Formula (2), or a tertiary onium salt expressed by Formula (3) can be provided.

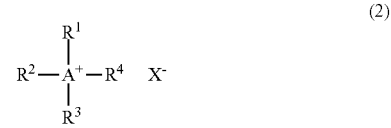

(2)

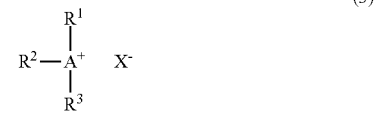

(3)

(In Formula (2), $A^+$ is an ammonium ion or a phosphonium ion; and $R^1$, $R^2$, $R^3$, and $R^4$ are independently an alkyl group with a carbon number from 1 to 25, an allyl group, an aralkyl group having an alkyl group with a carbon number from 1 to 25, or an aryl group. When $R^1$, $R^2$, $R^3$, and $R^4$ are alkyl groups, at least one of the alkyl groups in $R^1$, $R^2$, $R^3$, and $R^4$ has a carbon number of 2 or more. At least one hydrogen in a ring of an aryl group in the aralkyl group, or the aryl group may be replaced with fluorine, chlorine, an alkyl group with a carbon number from 1 to 10, an alkenyl group with a carbon number from 2 to 10, an alkoxy group with a carbon number from 1 to 9, or an alkenyloxy group with a carbon number from 2 to 9; and in these groups, at least one hydrogen may be replaced with fluorine or chlorine. In Formula (3), $A^+$ is a sulfonium ion; and $R^1$, $R^2$, and $R^3$ are independently an alkyl group with a carbon number from 1 to 25, an allyl group, an aralkyl group having an alkyl group with a carbon number from 1 to 25, or an aryl group. However, when $R^1$, $R^2$, and $R^3$ are alkyl groups, at least one of the alkyl groups in $R^1$, $R^2$, and $R^3$ has a carbon number of 2 or more. At least one hydrogen in a ring of an aryl group in the aralkyl group, or the aryl group may be replaced with fluorine, chlorine, an alkyl group with a carbon number from 1 to 10, an alkenyl group with a carbon number from 2 to 10, an alkoxy group with a carbon number from 1 to 9, or an alkenyloxy group with a carbon number from 2 to 9; and in these groups, at least one hydrogen may be replaced with fluorine or chlorine. In Formula (2) or (3), $X^-$ is a fluoride ion, a chloride ion, an iodide ion, a hydroxide ion, a nitrate ion, a phosphate ion, a sulfate ion, a hydrogen sulfate ion, a methanesulfate ion, a perchlorate ion, a chlorate ion, a chlorite ion, a hypochlorite ion, an orthoperiodate ion, a metaperiodate ion, an iodate ion, an iodite ion, a hypoiodite ion, an acetate ion, a carbonate ion, a hydrogencarbonate ion, a fluoroborate ion, or a trifluoroacetate ion.)

(24) A method for inhibiting ruthenium-containing gas generation using the inhibitor for ruthenium-containing gas generation according to (23) can be provided.

Further, a third aspect of the present invention for achieving the second object includes the following (25) to (40).

(25) A treatment liquid for a semiconductor wafer comprising an onium salt consisting of an onium ion and an anion, wherein the onium salt is an onium salt expressed by Formula (4).

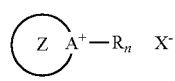

(4)

(In Formula (4), Z is an aromatic group or an alicyclic group that may contain a nitrogen, sulfur, or oxygen atom, and in the aromatic group or alicyclic group, the carbon or nitrogen may have;
chlorine, bromine, fluorine, iodine,
at least one alkyl group with a carbon number from 1 to 15,
at least one alkenyloxy group with a carbon number from 2 to 9,
an aromatic group that may be substituted with at least one alkyl group with a carbon number from 1 to 15, or
an alicyclic group that may be substituted with at least one alkyl group with a carbon number from 1 to 15;
A is nitrogen or sulfur;
R is chlorine, bromine, fluorine, iodine, an alkyl group with a carbon number from 1 to 15, an allyl group, an aromatic group that may be substituted with at least one alkyl group with a carbon number from 1 to 15, or an alicyclic group that may be substituted with at least one alkyl group with a carbon number from 1 to 15;
$X^-$ is an organic or inorganic anion; and
n is an integer of 1 or 2 and indicates the number of R, wherein when n is 2, R may be the same or different, and may form a ring.)

The invention may also employ the following aspect.

(26) A treatment liquid for a semiconductor wafer comprising an oxidizing agent and an onium salt consisting of an onium ion and an anion, wherein the onium salt is an onium salt expressed by Formula (4).

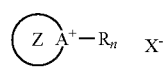

(4)

(In Formula (4), Z is an aromatic group or an alicyclic group that may contain a nitrogen, sulfur, or oxygen atom, and in the aromatic group or alicyclic group, the carbon or nitrogen may have;
chlorine, bromine, fluorine, iodine,
at least one alkyl group with a carbon number from 1 to 15,
at least one alkenyloxy group with a carbon number from 2 to 9,
an aromatic group that may be substituted with at least one alkyl group with a carbon number from 1 to 15, or
an alicyclic group that may be substituted with at least one alkyl group with a carbon number from 1 to 15;
A is nitrogen or sulfur;
R is chlorine, bromine, fluorine, iodine, an alkyl group with a carbon number from 1 to 15, an allyl group, an aromatic group that may be substituted with at least one alkyl group with a carbon number from 1 to 15, or an alicyclic group that may be substituted with at least one alkyl group with a carbon number from 1 to 15;
$X^-$ is an organic or inorganic anion; and
n is an integer of 1 or 2 and indicates the number of R, wherein when n is 2, R may be the same or different, and may form a ring.)

The invention may also employ the following aspect.

As the mechanism by which the treatment liquid of the third aspect of the present invention inhibits $RuO_4$ gas generation, the following is conceivable. That is, in an alkaline treatment liquid, anions such as $RuO_4^-$ and $RuO_4^{2-}$ generated by dissolution of ruthenium (hereinafter occasionally referred to as $RuO_4^-$, etc.) electrostatically interact with the onium ions contained in the treatment liquid, and part of them come to exist stably as ion pairs. This prevents the change from $RuO_4^-$ etc. to $RuO_4$, and as a result, $RuO_4$ gas generation is inhibited. In addition, since formation of $RuO_4$ is prevented, it is presumed that generation of $RuO_2$ particles caused by reduction of $RuO_4$ is also inhibited.

Therefore, the $RuO_4$ gas inhibitory effect by addition of the onium salt in the treatment liquid of the third aspect of the present invention is not limited to the type or amount of an oxidizing agent or other additives that can be included in the treatment liquid, the treatment method, the treatment condition or the like. For example, an oxidizing agent that can be included in the treatment liquid can be any publicly known oxidizing agents used as an oxidizing agent in a treatment liquid for a semiconductor. For example, a halogen oxyacid, permanganic acid, and their salts or ions, hydrogen peroxide, ozone, a cerium (IV) salt, etc. can be suitably used. When the treatment liquid of the third aspect of the present invention contains such an oxidizing agent, it can exhibit the $RuO_4$ gas inhibitory effect owing to the onium salt contained in the treatment liquid. Further, the treatment method for a semiconductor wafer with the treatment liquid of the third aspect of the present invention is not limited to wet etching, but can also be suitably used as a treatment liquid for cleaning applications or residue removal applications. Furthermore, when the treatment liquid of the third aspect of the present invention is used for CMP polishing, $RuO_4$ gas generation can also be inhibited in the CMP polishing step. The treatment of a wafer containing ruthenium with the treatment liquid of the third aspect of the present invention can be performed by a single wafer treatment, or an immersion treatment. The temperature of the treatment liquid is not particularly restricted, and at any treatment temperature, the inhibitory effect on $RuO_4$ gas generation can be obtained owing to the onium salt contained in the treatment liquid.

Further, for the sake of stronger inhibition of $RuO_4$ gas generation by increasing the reactivity of $RuO_4^-$, etc. with the onium salt, the following is preferable.

(27) The treatment liquid according to (25) or (26), wherein the onium salt is an imidazolium salt, a pyrrolidinium salt, a pyridinium salt, an oxazolium salt, or a piperidinium salt, is preferable.

(28) The treatment liquid according to any one of (25) to (27), wherein the organic or inorganic anion is a fluoride ion, a chloride ion, an iodide ion, a hydroxide ion, a nitrate ion, a phosphate ion, a sulfate ion, a hydrogen sulfate ion, a methanesulfate ion, a perchlorate ion, a chlorate ion, a chlorite ion, a hypochlorite ion, an orthoperiodate ion, a metaperiodate ion, an iodate ion, an iodite ion, a hypoiodite ion, an acetate ion, a carbonate ion, a hydrogencarbonate ion, a fluoroborate ion, a fluorophosphate ion, or a trifluoroacetate ion, is preferable.

In order to further inhibit a $RuO_4$ gas by increasing the addition amount of the onium salt,

(29) it is preferable to formulate the treatment liquid according to any one of (25) to (28), wherein the concentration of the onium salt in the treatment liquid is from 0.0001 to 50 mass %.

Further, in order to inhibit generation of $RuO_2$ particles, and to further inhibit $RuO_4$ gas generation, as well as to attain both a satisfactory processing speed of a ruthenium-containing wafer and the inhibition of $RuO_4$ gas,

(30) the treatment liquid according to any one of (25) to (29), wherein the treatment liquid comprises a hypochlorite ion and the concentration of the hypochlorite ion is from 0.05 to 20.0 mass %, is preferable.

As described above, in the third aspect of the present invention, $RuO_4^-$ etc. generated by dissolution of ruthenium are trapped by the onium salt contained in the treatment liquid, thereby inhibiting $RuO_4$ gas generation. In this case, $RuO_4^-$ etc. and onium ions are dissolved in the treatment liquid in the form of ion pairs, however when the solubility is exceeded, precipitates are formed. Since the precipitates become particles in the semiconductor formation process and cause decrease in the yield rate. Therefore, in order to dissolve the precipitates, it is necessary to increase the solubility, for which addition of an organic solvent is an effective method. Therefore, in the third aspect of the present invention the following embodiment is desirable. In other words, the treatment liquid is preferably:

(31) the treatment liquid according to any one of (25) to (30), further comprising an organic solvent.

When the precipitates dissolve into the treatment liquid, they may exist in the treatment liquid as ion pairs (in a state where the electrical interaction between $RuG_4^-$, etc. and onium ions is maintained), or exist independently as the respective ions, for which the interaction between $RuG_4^-$, etc. and onium ions has been lost. In the former case, $RuG_4^-$, etc. are trapped by the onium ion, and a $RuG_4$ gas is not generated, but in the latter case, $RuG_4^-$, etc. change to $RuG_4$ and a $RuG_4$ gas is generated. In the above, the difference between the former and the latter cases ascribes to the relative dielectric constant of the organic solvent to be added. Since, generally, when the relative dielectric constant of the solvent is lower, they are likely to exist as ion pairs, by adding an organic solvent with a low relative dielectric constant, it becomes possible to inhibit $RuO_4$ gas generation.

Namely,

(32) it is preferable to formulate the treatment liquid according to (31), wherein the relative dielectric constant of the organic solvent is 45 or less.

Furthermore, when the treatment liquid contains a strong oxidizing agent, an organic solvent to be added should preferably not react with the treatment liquid. Consequently,

(33) the treatment liquid according to (31) or (32), wherein the organic solvent is a sulfolane, an alkyl nitrile, a halogenated alkane, and an ether, is preferable.

Furthermore, in order to sufficiently dissolve the formed precipitates,

(34) it is preferable to formulate the treatment liquid according to any one of (31) to (33), wherein the concentration of the organic solvent in the treatment liquid is 0.1 mass % or more.

In order to maintain the processing speed of a ruthenium-containing wafer and the storage stability, while inhibiting $RuO_4$ gas generation,

(35) the treatment liquid according to any one of (25) to (34), wherein the pH at 25° C. is 7 or more and 14 or less, is preferable.

Further,

(36) use of the treatment liquid according to any one of (25) to (35) for etching a semiconductor wafer containing ruthenium can be provided.

Further,

(37) a method for etching a semiconductor wafer, comprising a step of bringing a semiconductor wafer containing ruthenium into contact with the treatment liquid according to any one of (25) to (35) can be provided.

Further,

(38) an inhibitor for ruthenium-containing gas generation comprising an onium salt consisting of an onium ion and an anion, wherein the onium salt is an onium salt expressed by Formula (4), is preferable.

(4)

(In Formula (4), Z is an aromatic group or an alicyclic group that may contain a nitrogen, sulfur, or oxygen atom, and in the aromatic group or alicyclic group, the carbon or nitrogen may have;

chlorine, bromine, fluorine, iodine, at least one alkyl group with a carbon number from 1 to 15, at least one alkenyloxy group with a carbon number from 2 to 9, an aromatic group that may be substituted with at least one alkyl group with a carbon number from 1 to 15, or an alicyclic group that may be substituted with at least one alkyl group with a carbon number from 1 to 15;

A is nitrogen or sulfur;

R is chlorine, bromine, fluorine, iodine, an alkyl group with a carbon number from 1 to 15, an allyl group, an aromatic group that may be substituted with at least one alkyl group with a carbon number from 1 to 15, or an alicyclic group that may be substituted with at least one alkyl group with a carbon number from 1 to 15;

X⁻ is an organic or inorganic anion; and n is an integer of 1 or 2 and indicates the number of R, wherein when n is 2, R may be the same or different, and may form a ring.)

In addition,

(39) an inhibitor for ruthenium-containing gas generation comprising an oxidizing agent and an onium salt consisting of an onium ion and an anion, wherein the onium salt is an onium salt expressed by Formula (4) is preferable.

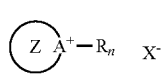

(4)

(In Formula (4), Z is an aromatic group or an alicyclic group that may contain a nitrogen, sulfur, or oxygen atom, and in the aromatic group or alicyclic group, the carbon or nitrogen may have;

chlorine, bromine, fluorine, iodine, at least one alkyl group with a carbon number from 1 to 15, at least one alkenyloxy group with a carbon number from 2 to 9, an aromatic group that may be substituted with at least one alkyl group with a carbon number from 1 to 15, or an alicyclic group that may be substituted with at least one alkyl group with a carbon number from 1 to 15;

A is nitrogen or sulfur;

R is chlorine, bromine, fluorine, iodine, an alkyl group with a carbon number from 1 to 15, an allyl group, an aromatic group that may be substituted with at least one alkyl group with a carbon number from 1 to 15, or an alicyclic group that may be substituted with at least one alkyl group with a carbon number from 1 to 15;

X⁻ is an organic or inorganic anion; and n is an integer of 1 or 2 and indicates the number of R, wherein when n is 2, R may be the same or different, and may form a ring.)

In addition,

(40) a method for inhibiting ruthenium-containing gas generation using the inhibitor for ruthenium-containing gas generation according to (38) or (39) is preferable.

Furthermore, a fourth aspect of the present invention for achieving the second object described above includes the following (41) to (53):

(41) a treatment liquid for a semiconductor wafer comprising an onium salt consisting of an onium ion and an anion, wherein the onium salt is an onium salt expressed by Formula (5).

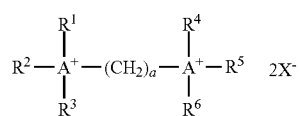

(5)

(In Formula (5), A⁺ are independently an ammonium ion, or a phosphonium ion; and R¹, R², R³, R⁴, R⁵, and R⁶ are independently an alkyl group with a carbon number from 1 to 25, an allyl group, an aralkyl group having an alkyl group with a carbon number from 1 to 25, or an aryl group. At least one hydrogen in a ring of an aryl group in the aralkyl group, or the aryl group may be replaced with fluorine, chlorine, an alkyl group with a carbon number from 1 to 10, an alkenyl group with a carbon number from 2 to 10, an alkoxy group with a carbon number from 1 to 9, or an alkenyloxy group with a carbon number from 2 to 9; and in these groups, at least one hydrogen may be replaced with fluorine or chlorine. In Formula (5), X⁻ is a fluoride ion, a chloride ion, an iodide ion, a hydroxide ion, a nitrate ion, a phosphate ion, a sulfate ion, a hydrogen sulfate ion, a methanesulfate ion, a perchlorate ion, a chlorate ion, a chlorite ion, a hypochlorite ion, an orthoperiodate ion, a metaperiodate ion, an iodate ion, an iodite ion, a hypoiodite ion, an acetate ion, a carbonate ion, a hydrogencarbonate ion, a fluoroborate ion, or a trifluoroacetate ion; and a is an integer of 1 to 10.)

As the mechanism by which the treatment liquid of the fourth aspect of the present invention inhibits RuO₄ gas generation, the following is conceivable. That is, in an alkaline treatment liquid, anions such as RuO₄⁻ and RuO₄²⁻ generated by dissolution of ruthenium (hereinafter occasionally referred to as RuO₄⁻, etc.) electrostatically interact with the onium ions contained in the treatment liquid, and part of them come to exist stably as ion pairs. This prevents the change from RuO₄⁻ etc. to RuO₄, and as a result, RuO₄ gas generation is inhibited. In addition, since formation of RuO₄ is prevented, it is presumed that generation of RuO₂ particles caused by reduction of RuO₄ is also inhibited.

Therefore, the RuO₄ gas inhibitory effect by addition of the onium salt in the treatment liquid of the fourth aspect of the present invention is not limited to the type or amount of an oxidizing agent or other additives that can be included in the treatment liquid, the treatment method, the treatment condition or the like. For example, an oxidizing agent that can be included in the treatment liquid of the fourth aspect can be any publicly known oxidizing agents used as an oxidizing agent in a treatment liquid for a semiconductor. For example, a halogen oxyacid, permanganic acid, and their salts or ions, hydrogen peroxide, ozone, a cerium (IV) salt, etc. can be suitably used. When the treatment liquid of the fourth aspect of the present invention contains such an oxidizing agent, it can exhibit the RuO₄ gas inhibitory effect owing to the onium salt contained in the treatment liquid. Further, the treatment method for a semiconductor wafer with the treatment liquid of the fourth aspect of the present invention is not limited to wet etching, but can also be suitably used as a treatment liquid for cleaning applications or residue removal applications. Furthermore, when the treatment liquid of the fourth aspect of the present invention is used for CMP polishing, RuO₄ gas generation can also be inhibited in the CMP polishing step. The treatment of a wafer containing ruthenium with the treatment liquid of the fourth aspect of the present invention can be performed by a single wafer treatment, or an immersion treatment. The temperature of the treatment liquid is not particularly restricted, and at any treatment temperature, the inhibitory effect on RuO₄ gas generation can be obtained owing to the onium salt contained in the treatment liquid.

Further, for the sake of stronger inhibition of a RuO₄ gas by increasing the addition amount of the onium salt,

(42) the treatment liquid according to (41), wherein the concentration of the onium salt in the treatment liquid is from 0.0001 to 50 mass %, is preferable.

Further, for the sake of inhibiting generation of $RuO_2$ particles and for the sake of stronger inhibition of $RuO_4$ gas generation,
- (43) the treatment liquid according to (41) or (42), wherein the treatment liquid comprises an oxidizing agent, is preferable.

Further, in order to achieve both satisfactory processing speed of a ruthenium-containing wafer and inhibition of a $RuO_4$ gas,
- (44) the treatment liquid according to any one of (41) to (43), wherein the treatment liquid comprises hypochlorite ions and the concentration of hypochlorite ions is from 0.05 to 20.0 mass %, is preferable.

As described above, in the fourth aspect of the present invention, $RuO_4^-$ etc. generated by dissolution of ruthenium are trapped by the onium salt contained in the treatment liquid, thereby inhibiting $RuO_4$ gas generation. In this case, $RuO_4^-$ etc. and onium ions are dissolved in the treatment liquid in the form of ion pairs, however when the solubility is exceeded, precipitates are formed. Since the precipitates become particles in the semiconductor formation process and cause decrease in the yield rate. Therefore, in order to dissolve the precipitates, it is necessary to increase the solubility, for which addition of an organic solvent is an effective method. Therefore, in the fourth aspect of the present invention the following embodiment is desirable. In other words, the treatment liquid is preferably:
- (45) the treatment liquid according to any one of (41) to (44) further comprising an organic solvent.

When the precipitates dissolve into the treatment liquid, they may exist in the treatment liquid as ion pairs (in a state where the electrical interaction between $RuO_4$, etc. and onium ions is maintained), or exist independently as the respective ions, for which the interaction between $RuO_4^-$, etc. and onium ions has been lost. In the former case, $RuO_4^-$, etc. are trapped by the onium ion, and a $RuO_4$ gas is not generated, but in the latter case, $RuO_4$, etc. change to $RuO_4$ and a $RuO_4$ gas is generated. In the above, the difference between the former and the latter cases ascribes to the relative dielectric constant of the organic solvent to be added. Since, generally, when the relative dielectric constant of the solvent is lower, they are likely to exist as ion pairs, by adding an organic solvent with a low relative dielectric constant, it becomes possible to inhibit $RuO_4$ gas generation. Namely,
- (46) the treatment liquid according to (45), wherein the relative dielectric constant of the organic solvent is 45 or less, is preferable.

Furthermore, when the treatment liquid contains a strong oxidizing agent, an organic solvent to be added should preferably not react with the treatment liquid. Consequently,
- (47) it is preferable to formulate the treatment liquid according to (45) or (46), wherein the organic solvent is a sulfolane, an alkyl nitrile, a halogenated alkane, or an ether.

Furthermore, in order to sufficiently dissolve the formed precipitates,
- (48) it is preferable to formulate the treatment liquid according to any one of (45) to (47), wherein the concentration of the organic solvent in the treatment liquid is 0.1 mass % or more.

In order to maintain the processing speed of a ruthenium-containing wafer and the storage stability, while inhibiting $RuO_4$ gas generation
- (49) it is preferable to formulate the treatment liquid according to any one of (41) to (48), wherein the pH at 25° C. is 7 or more and 14 or less.

Further,
- (50) use of the treatment liquid according to any one of (41) to (49) for etching a semiconductor wafer containing ruthenium can be provided.

Further,
- (51) a method for etching a semiconductor wafer comprising a step of bringing a semiconductor wafer containing ruthenium into contact with the treatment liquid according to any one of (41) to (49) can be provided.

Further,
- (52) an inhibitor for ruthenium-containing gas generation comprising an onium salt consisting of an onium ion and an anion, wherein the onium salt is an onium salt expressed by Formula (5) can be provided.

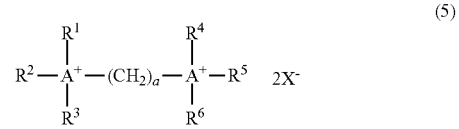

(In Formula (5), $A^+$ are independently an ammonium ion or a phosphonium ion, and $R^1$, $R^2$, $R^3$, $R^4$, $R^5$, and $R^6$ are independently an alkyl group with a carbon number from 1 to 25, an allyl group, an aralkyl group having an alkyl group with a carbon number from 1 to 25, or an aryl group. At least one hydrogen in a ring of an aryl group in the aralkyl group, or the aryl group may be replaced with fluorine, chlorine, an alkyl group with a carbon number from 1 to 10, an alkenyl group with a carbon number from 2 to 10, an alkoxy group with a carbon number from 1 to 9, or an alkenyloxy group with a carbon number from 2 to 9; and in these groups, at least one hydrogen may be replaced with fluorine or chlorine. In Formula (5), $X^-$ is a fluoride ion, a chloride ion, an iodide ion, a hydroxide ion, a nitrate ion, a phosphate ion, a sulfate ion, a hydrogen sulfate ion, a methanesulfate ion, a perchlorate ion, a chlorate ion, a chlorite ion, a hypochlorite ion, an orthoperiodate ion, a metaperiodate ion, an iodate ion, an iodite ion, a hypoiodite ion, an acetate ion, a carbonate ion, a hydrogencarbonate ion, a fluoroborate ion, or a trifluoroacetate ion; and a is an integer of 1 to 10.)

Further,
- (53) A method for inhibiting ruthenium-containing gas generation using the inhibitor for ruthenium-containing gas generation according to (52) can be provided.

Also, according to the present invention, which achieves the second object, (54) a treatment agent for a ruthenium-containing waste fluid, comprising an onium salt consisting of an onium ion and an anion, wherein the onium salt is a quaternary onium salt expressed by Formula (2), a tertiary onium salt expressed by Formula (3), an onium salt expressed by Formula (4), or an onium salt expressed by Formula (5), can be provided.

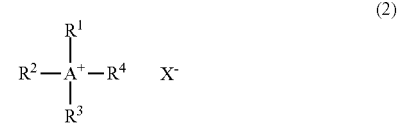

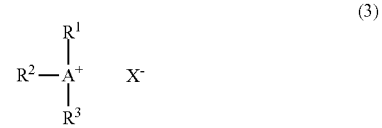

-continued

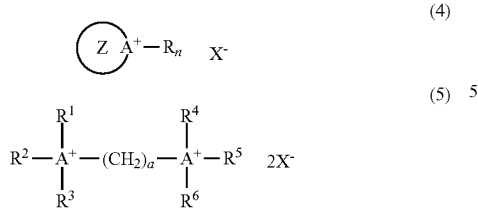
(4)

$$R^2-\overset{\overset{\displaystyle R^1}{|}}{\underset{\underset{\displaystyle R^3}{|}}{A^+}}-(CH_2)_a-\overset{\overset{\displaystyle R^4}{|}}{\underset{\underset{\displaystyle R^6}{|}}{A^+}}-R^5 \quad 2X^- \quad (5)$$

(In Formula (2), $A^+$ is an ammonium ion or a phosphonium ion; and $R^1$, $R^2$, $R^3$, and $R^4$ are independently an alkyl group with a carbon number from 1 to 25, an allyl group, an aralkyl group having an alkyl group with a carbon number from 1 to 25, or an aryl group. When $R^1$, $R^2$, $R^3$, and $R^4$ are alkyl groups, at least one of the alkyl groups in $R^1$, $R^2$, $R^3$, and $R^4$ has a carbon number of 2 or more. At least one hydrogen in a ring of an aryl group in the aralkyl group, or the aryl group may be replaced with fluorine, chlorine, an alkyl group with a carbon number from 1 to 10, an alkenyl group with a carbon number from 2 to 10, an alkoxy group with a carbon number from 1 to 9, or an alkenyloxy group with a carbon number from 2 to 9; and in these groups, at least one hydrogen may be replaced with fluorine or chlorine.

In Formula (3), $A^+$ is a sulfonium ion; and $R^1$, $R^2$, and $R^3$ are independently an alkyl group with a carbon number from 1 to 25, an allyl group, an aralkyl group having an alkyl group with a carbon number from 1 to 25, or an aryl group. When $R^1$, $R^2$, and $R^3$ are alkyl groups, at least one of the alkyl groups in $R^1$, $R^2$, and $R^3$ has a carbon number of 2 or more. At least one hydrogen in a ring of an aryl group in the aralkyl group, or the aryl group may be replaced with fluorine, chlorine, an alkyl group with a carbon number from 1 to 10, an alkenyl group with a carbon number from 2 to 10, an alkoxy group with a carbon number from 1 to 9, or an alkenyloxy group with a carbon number from 2 to 9; and in these groups, at least one hydrogen may be replaced with fluorine or chlorine.

In Formula (2) or (3), $X^-$ is a fluoride ion, a chloride ion, an iodide ion, a hydroxide ion, a nitrate ion, a phosphate ion, a sulfate ion, a hydrogen sulfate ion, a methanesulfate ion, a perchlorate ion, a chlorate ion, a chlorite ion, a hypochlorite ion, an orthoperiodate ion, a metaperiodate ion, an iodate ion, an iodite ion, a hypoiodite ion, an acetate ion, a carbonate ion, a hydrogencarbonate ion, a fluoroborate ion, or a trifluoroacetate ion.

In Formula (4), Z is an aromatic group or an alicyclic group that may contain a nitrogen, sulfur, or oxygen atom, and in the aromatic group or alicyclic group, the carbon or nitrogen may have;

chlorine, bromine, fluorine, iodine,
at least one alkyl group with a carbon number from 1 to 15,
at least one alkenyloxy group with a carbon number from 2 to 9,
an aromatic group that may be substituted with at least one alkyl group with a carbon number from 1 to 15, or
an alicyclic group that may be substituted with at least one alkyl group with a carbon number from 1 to 15;
A is nitrogen or sulfur;
R is chlorine, bromine, fluorine, iodine, an alkyl group with a carbon number from 1 to 15, an allyl group, an aromatic group that may be substituted with at least one alkyl group with a carbon number from 1 to 15, or an alicyclic group that may be substituted with at least one alkyl group with a carbon number from 1 to 15;
$X^-$ is an organic or inorganic anion; and
n is an integer of 1 or 2 and indicates the number of R, wherein when n is 2, R may be the same or different, and may form a ring.

In Formula (5), $A^+$ are independently an ammonium ion or a phosphonium ion, and $R^1$, $R^2$, $R^3$, $R^4$, $R^5$, and $R^6$ are independently an alkyl group with a carbon number from 1 to 25, an allyl group, an aralkyl group having an alkyl group with a carbon number from 1 to 25, or an aryl group. At least one hydrogen in a ring of an aryl group in the aralkyl group, or the aryl group may be replaced with fluorine, chlorine, an alkyl group with a carbon number from 1 to 10, an alkenyl group with a carbon number from 2 to 10, an alkoxy group with a carbon number from 1 to 9, or an alkenyloxy group with a carbon number from 2 to 9; and in these groups, at least one hydrogen may be replaced with fluorine or chlorine. In Formula (5), $X^-$ is a fluoride ion, a chloride ion, an iodide ion, a hydroxide ion, a nitrate ion, a phosphate ion, a sulfate ion, a hydrogen sulfate ion, a methanesulfate ion, a perchlorate ion, a chlorate ion, a chlorite ion, a hypochlorite ion, an orthoperiodate ion, a metaperiodate ion, an iodate ion, an iodite ion, a hypoiodite ion, an acetate ion, a carbonate ion, a hydrogencarbonate ion, a fluoroborate ion, or a trifluoroacetate ion; and a is an integer of 1 to 10.)

Further, 55. a method for treating a ruthenium-containing waste fluid using the treatment agent for a ruthenium-containing waste fluid according to (54) can be provided.

Advantageous Effects of Invention

Using a treatment liquid of the first aspect of the present invention, ruthenium can be wet-etched in a forming process of a semiconductor element, and furthermore, the flatness of the ruthenium surface after the etching treatment can be maintained. Therefore, it is suitable for use in the formation of a semiconductor element having a multilayer wiring structure, for which the flatness of each layer is required.

Since the treatment liquid of the first aspect of the present invention gives excellent flatness of the ruthenium surface after the etching treatment, the ruthenium surface in contact with the treatment liquid can be etched evenly. Especially, even in the formation of a semiconductor element with a wiring structure with a dimension of 10 nm or less, where precise etching of ruthenium at several nanometer level is required, since the ruthenium surface in contact with the treatment liquid can be etched notably evenly, the treatment liquid can be used favorably.

Furthermore, the treatment liquid of the first aspect of the present invention is capable of etching ruthenium at an etching rate of 20 Å/min or higher. With an etching rate of 20 Å/min or higher, it can be used satisfactorily in the process of forming a semiconductor element.

Meanwhile, with the treatment liquids of the second to fourth aspects of the invention, owing to the effect of the onium salt, ruthenium-containing gas generation, which may cause particle formation, or decline in the yield rate in a semiconductor manufacturing process, can be inhibited. Further, since the selectable pH range and types of oxidizing agents can be increased, it becomes possible to create a stable treatment liquid by selecting an appropriate oxidizing agent.

DESCRIPTION OF EMBODIMENTS

In this description, ruthenium (also expressed as Ru) is not limited to a ruthenium metal, insofar as the ruthenium element is included.

(Treatment Liquid of First Aspect)

The treatment liquid of the first aspect of the present invention is a treatment liquid that can etch ruthenium present on a semiconductor wafer without damaging the semiconductor wafer. Therefore, the treatment liquid of the first aspect of the present invention is a treatment liquid that can be suitably used in the wiring formation step in the semiconductor manufacturing process.

Figure 1:
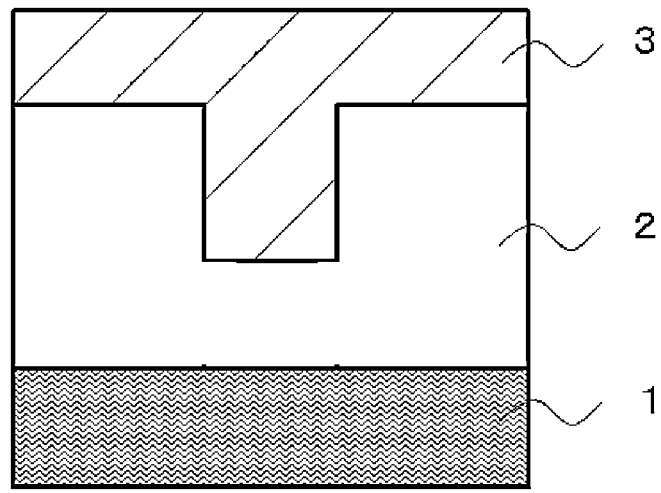
FIG. 1: A schematic cross-sectional view showing an example of the wiring formation step in which the treatment liquid of the first aspect of the present invention can be suitably employed.
Figure 2:
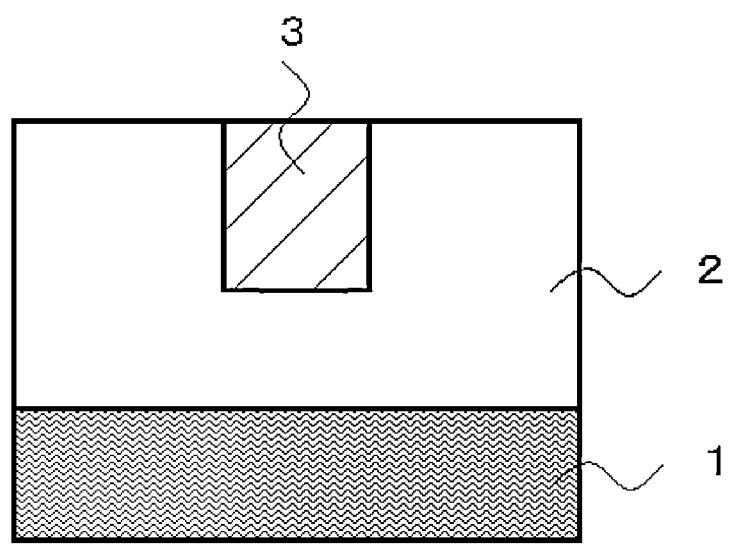
FIG. 2: A schematic cross-sectional view showing an example of the wiring formation step after the treatment with the treatment liquid of the first aspect of the present invention.

The ruthenium to which the treatment liquid of the first aspect of the present invention is applied is mainly formed by a publicly known method, such as CVD, ALD, and a sputtering method, used in the semiconductor element process. Through etching the formed ruthenium, the wiring is formed in the semiconductor. FIGS. 1 and 2 show an example of the wiring formation step.

First, a substrate 1 made of a semiconductor (e.g. Si) is prepared. The prepared substrate is subjected to an oxidation treatment to form a silicon oxide film on the substrate. Then, an interlayer insulating film 2 constituted with a low dielectric constant (low-k) film is formed, and in which via holes are formed at predetermined intervals. After formation, the via holes are filled with ruthenium 3 by thermal CVD, and a ruthenium film is further deposited thereon (FIG. 1). The ruthenium film is etched and planarized by dry etching or wet etching to form the ruthenium wiring (FIG. 2).

The treatment liquid of the first aspect of the present invention contains (A) a hypochlorite ion, and (B) an alkylammonium salt expressed by the following Formula (1). The following is a step by step description.

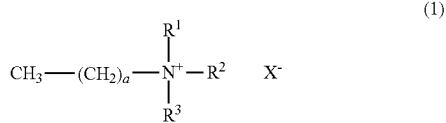
(1)

(In the Formula, "a" is an integer from 6 to 20; and $R^1$, $R^2$, and $R^3$ are independently a hydrogen atom, or an alkyl group with a carbon number from 1 to 20. $X^-$ is a fluoride ion, a chloride ion, an iodide ion, a hydroxide ion, a nitrate ion, a phosphate ion, a sulfate ion, a hydrogen sulfate ion, a methanesulfate ion, a perchlorate ion, an acetate ion, a fluoroborate ion, or a trifluoroacetate ion.)

(A) Hypochlorite Ion

With respect to the hypochlorite ion to be used in the first aspect of the present invention, it is possible to generate hypochlorous acid and hypochlorite ions by dissolving hypochlorite in water. The hypochlorite ion is an oxidizing agent with strong oxidizability, and the treatment liquid of the present invention containing hypochlorite ions can etch a metal contained in a semiconductor wafer.

In the first aspect of the present invention, the concentration of hypochlorite ions is preferably in a range of 0.05 to 20 mass % with respect to the total treatment liquid. Within the above range, it is possible to prevent the hypochlorite ion concentration from decreasing by inhibiting the decomposition reaction of hypochlorite ions in a treatment liquid (hereinafter, the effect of inhibiting the decomposition reaction of hypochlorite ions in a treatment liquid so as to inhibit the hypochlorite ion concentration from decreasing is occasionally referred to as "high storage stability"), and to etch ruthenium at an etching rate of 20 Å/min or higher. Therefore, the concentration of hypochlorite ions is preferably in a range of 0.1 to 15 mass %, more preferably 0.3 to 10 mass %, further preferably 0.5 to 6 mass %, and especially preferably 0.5 to 4 mass %.

The concentration of hypochlorite ions in a treatment liquid of the first aspect of the present invention can be calculated at the time of the production of the treatment liquid, or can be affirmed by a direct analysis of the treatment liquid. The concentration of hypochlorite ions described in Example below was determined by measuring the effective chlorine concentration of the treatment liquid. Specifically, referring to Ministry of Health, Labour and Welfare Notification No. 318 (final revision on 11 Mar. 2005), potassium iodide and acetic acid were added to a solution containing hypochlorite ions, the liberated iodine was redox-titrated with an aqueous solution of sodium thiosulfate, and the effective chlorine concentration was calculated. The concentration of hypochlorite ions of the present invention is obtained by converting from the calculated effective chlorine concentration.

(B) Alkylammonium Salt Expressed by the Following Formula (1)

The alkylammonium salt contained in a treatment liquid of the first aspect of the present invention is the alkylammonium salt expressed by the following Formula (1).

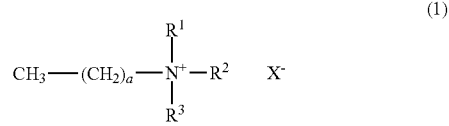
(1)

(In the Formula, "a" is an integer from 6 to 20; and $R^1$, $R^2$, and $R^3$ are independently a hydrogen atom, or an alkyl group with a carbon number from 1 to 20. $X^-$ is a fluoride ion, a chloride ion, an iodide ion, a hydroxide ion, a nitrate ion, a phosphate ion, a sulfate ion, a hydrogen sulfate ion, a methanesulfate ion, a perchlorate ion, an acetate ion, a fluoroborate ion, or a trifluoroacetate ion.)

The integer "a" in the above Formula (1) represents the number of methylene groups, and those in which the integer "a" is from 6 to 20 can be used without any particular restriction, and the integer "a" is more preferably from 6 to 15, and further preferably from 8 to 13. An alkylammonium salt having methylene groups within the aforedescribed range can be adsorbed onto the ruthenium surface to form an appropriate protective layer, and therefore can be favorably used. In this regard, when the integer "a" of the alkylammonium salt is larger, the amount of alkylammonium ions of the alkylammonium salt adsorbed onto the ruthenium surface increases, and therefore the etching rate of ruthenium tends to decrease. On the other hand, when the integer "a" of the alkylammonium salt is smaller, the amount adsorbed onto the ruthenium surface decreases, and an appropriate protective layer is not formed on the ruthenium surface, and the flatness of the ruthenium surface after the etching treatment is not likely to be maintained.

Meanwhile, when the integer "a" of the alkylammonium salt is large, the water solubility of the alkylammonium salt is low, which will cause generation of particles in the treatment liquid. When particles remain on the ruthenium surface after the etching treatment, the yield rate of semiconductor elements will be reduced, so a smaller amount of particles is preferable. Considering the adsorption performance to the ruthenium surface and the water solubility into a treatment liquid, it is more preferable that the integer "a" in Formula (1) is from 6 to 15, and further preferable from 8 to 13.

In Formula (1), $R^1$, $R^2$, and $R^3$ are independently a hydrogen atom, or an alkyl group having a carbon number from 1 to 20, and may be the same or different from each other. $R^1$, $R^2$, and $R^3$ are preferably alkyl groups having a carbon number from 1 to 20. Furthermore, it is preferable that the carbon numbers of $R^1$, $R^2$, and $R^3$ are respectively the same as, or smaller than the integer "a". It is more preferable that any one of $R^1$, $R^2$, and $R^3$ is a methyl group. When any one of $R^1$, $R^2$, and $R^3$ is a methyl group, a more uniform and dense protective layer is formed on the ruthenium surface, and the flatness of the ruthenium surface after the etching treatment can be maintained.

$X^-$ in Formula (1) is a fluoride ion, a chloride ion, an iodide ion, a hydroxide ion, a nitrate ion, a phosphate ion, a sulfate ion, a hydrogen sulfate ion, a methanesulfate ion, a perchlorate ion, an acetate ion, a fluoroborate ion, or a trifluoroacetate ion. There is no particular restriction on the anion of an alkylammonium salt, and it can be used in a treatment liquid.

As the mechanism by which the treatment liquid of the first aspect of the present invention can maintain the flatness of the ruthenium surface after the etching treatment, the following is conceivable. That is, the cation (alkylammonium ion) of the alkylammonium salt contained in the treatment liquid is conceivably adsorbed onto the ruthenium surface at the polar group centered by a nitrogen atom. The non-polar alkyl groups of the adsorbed cation take positions away from the ruthenium surface, resulting in formation of a hydrophobic protective layer on the ruthenium surface. Since the formed protective layer inhibits the contact between hypochlorite ions contained in the treatment liquid and ruthenium, as a result, the ruthenium is etched evenly, and the flatness of the ruthenium surface after the etching treatment is maintained.

Specific examples of the alkylammonium salt expressed by Formula (1) that can be suitably used in the first aspect of the present invention include n-octyltrimethylammonium chloride, decyltrimethylammonium chloride, lauryltrimethylammonium chloride, tetradecyltrimethylammonium chloride, hexadecyltrimethylammonium chloride, octadecyltrimethylammonium chloride, didecyldimethylammonium chloride, didodecyldimethylammonium chloride, and tetraheptylammonium chloride.

The addition amount of an alkylammonium salt is preferably in a range of 0.001 to 10 mass % with respect to the entire treatment liquid. Within this range, the etching rate of ruthenium does not decrease, and a sufficient protective layer can be formed on the ruthenium surface. When the alkylammonium salt is added, only one kind can be added, or a mixture of two or more kinds can be added.

The treatment liquid of the first aspect of the present invention is composed of (A), (B), (C) which is described in detail below, and other additives, as well as water as the balance. The water contained in the treatment liquid of the present invention is preferably water from which metal ions, organic impurities, particles, etc. have been removed by distillation, an ion exchange treatment, a filtration treatment, various adsorption treatments, or the like, and especially pure water or ultrapure water is particularly preferable.

(C) Ammonium Ion

In the treatment liquid of the first aspect of the present invention, a hypochlorite ion is included in the treatment liquid by dissolving a hypochlorite in water, or likewise. Therefore, the counter ion of the hypochlorite ion is included inevitably in the treatment liquid. Usually, the hypochlorite is sodium hypochlorite, calcium hypochlorite, or the like, and in such a case, a sodium ion or a calcium ion is included as the counter ion.

In this regard, when the above-mentioned alkali metal ion or alkaline earth metal ion, such as a sodium ion, and a calcium ion, remains on the semiconductor wafer, an adverse effect (adverse effect such as decrease in the yield rate of the semiconductor wafer) will be exerted on the semiconductor wafer. Therefore, the content of the hypochlorite ion should preferably be small, and most preferably it should be substantially not contained. Therefore, as the counter ion of a hypochlorite ion, an organic counter ion is preferable, and in consideration of industrial production, at least one kind of ammonium ion selected from tetramethylammonium ion, tetraethylammonium ion, tetrapropylammonium ion, and tetrabutylammonium ion is preferable, and particularly tetramethylammonium ion is preferable. Accordingly, when a tetramethylammonium ion is selected as the counter ion, the content of sodium ions and calcium ions in the treatment liquid can be reduced, therefore it is preferable to include tetramethylammonium ions in the treatment liquid. It may additionally include the same as tetramethylammonium hydroxide or a tetramethylammonium hydroxide salt.

In the first aspect of the present invention, the concentration of ammonium ions is preferably in a range of 0.1 to 30 mass % with respect to the entire treatment liquid. When this concentration range of ammonium ions is satisfied, the treatment liquid can have excellent long-term storage stability. To further improve the storage stability, the concentration of ammonium ions is more preferably from 0.15 to 20 mass %, further preferably from 0.3 to 15 mass %, and especially preferably from 0.5 to 8 mass %.

In the first aspect of the present invention, tetramethylammonium ions can be made to be contained in a treatment liquid by, for example, passing an aqueous solution of tetramethylammonium hydroxide through an ion exchange resin to prepare the ion exchange resin exchanged to the tetramethylammonium ion form. A solution containing hypochlorite ions is brought into contact therewith so that ion exchange occurs with cations contained in the solution, thereby introducing tetramethylammonium ions into the treatment liquid.

With respect to the treatment liquid of the first aspect of the present invention, the pH is preferably greater than 7 and less than 14. When the pH of the treatment liquid is less than 7, a decomposition reaction of hypochlorite ions is prone to occur, and the concentration of hypochlorite ions tends to decrease easily. Therefore, in order to satisfactorily secure both the storage stability of the treatment liquid and the etching rate of ruthenium, the pH of the treatment liquid is preferably greater than 7 and less than 14, and more preferably 8 or more and less than 11. For example, when the pH is within the above range, the concentration of hypochlorite ions is not likely to decrease during the storage. For example, even after the storage in the dark at 23° C. in an inert gas atmosphere for 15 days, the treatment liquid can exhibit adequate ruthenium etching performance. In this regard, a pH refers to the value at 25° C. in this specification.
(Other Additives)

Other additives conventionally used in a treatment liquid for semiconductors can be optionally added to a treatment liquid of the first aspect of the present invention, to the extent that the purpose of the present invention is not impaired. For example, an acid, a metal corrosion inhibitor, a water-soluble organic solvent, a fluorine compound, an oxidizing agent, a reducing agent, a complexing agent, a chelating agent, a nonionic surfactant, a defoaming agent, and a pH adjuster can be added as other additives.

Derived from such other additives, or for reasons in manufacturing a treatment liquid, an alkali metal ion, and an alkaline earth metal ion, such as a sodium ion and a calcium ion may be included in a treatment liquid of the present invention. However, as mentioned above, when the alkali metal ion or alkaline earth metal ion remains on a semiconductor wafer, an adverse effect (adverse effect such as decrease in the yield rate of the semiconductor wafer) will be exerted on the semiconductor wafer. Therefore, the content thereof should preferably be small, and most preferably it should be substantially not contained. Therefore, for example, as a pH adjuster, it is preferable to use an organic alkali such as a tetraalkylammonium hydroxide, rather than an alkali metal hydroxide such as sodium hydroxide, or an alkaline earth metal hydroxide.

Specifically, the total amount of alkali metal ions and alkaline earth metal ions is preferably 1 mass % or less, more preferably 0.7 mass % or less, further preferably 0.3 mass % or less, especially preferably 10 ppm or less, and most preferably 500 ppb or less.
(Method for Producing Treatment Liquid of First Aspect)

The treatment liquid, etc. of the first aspect of the present invention will be described below.

A treatment liquid of the first aspect of the present invention can be produced by adding and mixing an alkylammonium salt to an aqueous solution of hypochlorite containing hypochlorite ions. The hypochlorite aqueous solution can be produced by dissolving a commercially available hypochlorite, such as sodium hypochlorite or calcium hypochlorite, in water, or blowing chlorine into an alkali aqueous solution such as a sodium hydroxide aqueous solution or a tetramethylammonium hydroxide aqueous solution. Further, for example, when an aqueous solution of sodium hypochlorite is brought into contact with an ion exchange resin modified to a tetramethylammonium form, the counter ion of a hypochlorite ion can be exchanged.

A method for producing a treatment liquid of the first aspect of the present invention in which a sodium hypochlorite aqueous solution is converted to a tetramethylammonium hypochlorite aqueous solution by a method for producing a treatment liquid using a hypochlorite aqueous solution in which the counter ion of the hypochlorite ion is exchanged by an ion exchange resin, will be described in detail below.

First, an aqueous solution containing tetramethylammonium ions, specifically, an aqueous solution of tetramethylammonium hydroxide, is brought into contact with an ion exchange resin to prepare an ion exchange resin in a tetramethylammonium form.

There is no particular restriction on the ion exchange resin to be used, insofar as it is a publicly known cation exchange resin. For example, a hydrogen-form ion exchange resin or a sodium-form ion exchange resin can be used. Among others, a hydrogen-form ion exchange resin, which is less likely to be contaminated with sodium, is preferable. Further, in the case of a hydrogen form ion exchange resin, a mildly acidic, or a strongly acidic ion exchange resin can be used without particular restriction.

After preparing the ion exchange resin in a tetramethylammonium form, an aqueous solution of tetramethylammonium hypochlorite can be produced by bringing a hypochlorite aqueous solution into contact with the ion exchange resin.

A sodium hypochlorite aqueous solution can be prepared by dissolving sodium hypochlorite in water. Although in this case sodium hypochlorite is used because it is superior in storage stability and handling property, calcium hypochlorite, etc. can also be used insofar as it is on the market and easily available.

Further, the step of ion exchange can be repeated. By repeating the step of ion exchange, it is possible to decrease metal ions such as sodium and calcium, which become counter ions of hypochlorite ions contained in the aqueous solution of tetramethylammonium hypochlorite.

A treatment liquid of the present invention containing tetramethylammonium ions can be produced by mixing and dissolving an alkylammonium salt and other optional additives into the obtained aqueous solution of tetramethylammonium hypochlorite.
(Method for Etching Ruthenium)

The etching conditions using a treatment liquid of the first aspect of the present invention can be appropriately selected according to the etching conditions of the etching equipment used, while the temperature is in a range of 10 to 80° C., and preferably 20 to 70° C.

The etching rate of ruthenium varies with temperature. Therefore, in order to increase the etching rate of ruthenium, a range of 40 to 70° C. should be selected in the above temperature range. In the temperature range of 40 to 70° C., the etching rate can be accelerated, and the treatment can be performed in a simple apparatus but with good operability.

The application time of a treatment liquid of the present invention is in a range of 0.1 to 120 min, and preferably 0.5 to 60 min, and can be appropriately selected according to the etching conditions and the type of a semiconductor element to be applied. As a rinse liquid after the application of the treatment liquid, an organic solvent such as alcohol can be used, but simply rinsing with deionized water is sufficient.

As described above, with the treatment liquid of the first aspect of the present invention, the etching rate on ruthenium can achieve 20 Å/min or more, and preferably 50 Å/min or more, and the flatness of the ruthenium surface after etching can be made excellent. As obvious from the above, the treatment liquid of the present invention can be suitably used when ruthenium is used in the semiconductor element formation process.
(Treatment Liquid of the Second Aspect)

The treatment liquid, etc. of the second aspect of the present invention will be described below.

The treatment liquid of the second aspect of the present invention is a treatment liquid that can treat a semiconductor wafer containing ruthenium without generating a $RuO_4$ gas. Therefore, the treatment liquid of the second aspect of the present invention is a treatment liquid that can be suitably used in a step of etching, a step of removing residues, a step of washing, a CMP step, etc. in a semiconductor manufacturing process.

The ruthenium contained in a semiconductor wafer to which the treatment liquid of the second aspect of the present invention is applied can be formed by any method. For film formation of ruthenium, a method publicly well known for a semiconductor manufacturing process, such as CVD, ALD, sputtering, and plating, can be utilized. Such ruthenium can be metallic ruthenium, a ruthenium oxide, an alloy with another metal, an intermetallic compound, an ionic compound, or a complex. The ruthenium can be exposed on the surface of the wafer, or covered with another metal, a metal oxide film, an insulating film, a resist, or the like. Even in a case covered with another material, when ruthenium comes into contact with the treatment liquid and dissolution of ruthenium occurs, the onium salt contained in the treatment liquid of the second aspect of the present invention exerts the inhibitory effect on $RuO_4$ gas generation. Furthermore, in a case where ruthenium is not forced to be dissolved, in other words, in a treatment where ruthenium is the object of protection, the treatment liquid of the second aspect of the present invention is still capable of inhibiting a $RuO_4$ gas generated from a very small amount of dissolved ruthenium For example, in a case where the treatment liquid of the second aspect of the present invention is used in a step of forming a ruthenium wiring, the procedure is as follows. First, a substrate made of a semiconductor (e.g. Si) is prepared. The prepared substrate is subjected to an oxidation treatment to form a silicon oxide film on the substrate. Then, an interlayer insulating film constituted with a low dielectric constant (low-k) film is formed, and in which via holes are formed at predetermined intervals. After formation of via holes, the via holes are filled with ruthenium by thermal CVD, and a ruthenium film is further deposited thereon. The ruthenium film is etched using the treatment liquid of the present invention for planarization while inhibiting $RuO_4$ gas generation. By doing so, a highly reliable ruthenium wiring can be formed, while formation of $RuO_2$ particles can be inhibited.

The treatment liquid of the second aspect of the present invention comprises an onium salt consisting of an onium ion and an anion. This will be described step by step below.

The onium salt is represented by the following Formula (2) or (3).

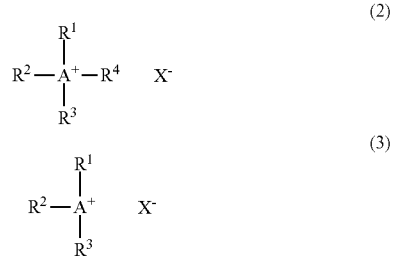

(In Formula (2), $A^+$ is an ammonium ion, or a phosphonium ion; and $R^1$, $R^2$, $R^3$, and $R^4$ are independently an alkyl group with a carbon number from 1 to 25, an allyl group, an aralkyl group having an alkyl group with a carbon number from 1 to 25, or an aryl group. When $R^1$, $R^2$, $R^3$, and $R^4$ are alkyl groups, at least one of the alkyl groups in $R^1$, $R^2$, $R^3$, and $R^4$ has a carbon number of 2 or more. At least one hydrogen in a ring of an aryl group in the aralkyl group, or the aryl group may be replaced with fluorine, chlorine, an alkyl group with a carbon number from 1 to 10, an alkenyl group with a carbon number from 2 to 10, an alkoxy group with a carbon number from 1 to 9, or an alkenyloxy group with a carbon number from 2 to 9; and in these groups, at least one hydrogen may be replaced with fluorine or chlorine. In Formula (3), $A^+$ is a sulfonium ion; and $R^1$, $R^2$, and $R^3$ are independently an alkyl group with a carbon number from 1 to 25, an allyl group, an aralkyl group having an alkyl group with a carbon number from 1 to 25, or an aryl group. When $R^1$, $R^2$, and $R^3$ are alkyl groups, at least one of the alkyl groups in $R^1$, $R^2$, and $R^3$ has a carbon number of 2 or more. At least one hydrogen in a ring of an aryl group in the aralkyl group, or the aryl group may be replaced with fluorine, chlorine, an alkyl group with a carbon number from 1 to 10, an alkenyl group with a carbon number from 2 to 10, an alkoxy group with a carbon number from 1 to 9, or an alkenyloxy group with a carbon number from 2 to 9; and in these groups, at least one hydrogen may be replaced with fluorine or chlorine. In Formula (2) or (3), $X^-$ is a fluoride ion, a chloride ion, an iodide ion, a hydroxide ion, a nitrate ion, a phosphate ion, a sulfate ion, a hydrogen sulfate ion, a methanesulfate ion, a perchlorate ion, a chlorate ion, a chlorite ion, a hypochlorite ion, an orthoperiodate ion, a metaperiodate ion, an iodate ion, an iodite ion, a hypoiodite ion, an acetate ion, a carbonate ion, a hydrogencarbonate ion, a fluoroborate ion, or a trifluoroacetate ion.)

The alkyl groups of $R^1$, $R^2$, $R^3$, and $R^4$ in Formula (2) or (3) can be used without any particular restriction insofar as the carbon numbers are independently from 1 to 25. The larger the carbon number, the stronger the interaction of the onium ion with $RuO_4$, etc. becomes, and the more easily the $RuO_4$ gas is inhibited. On the other hand, the larger the carbon number, the bulkier the onium ion becomes, and therefore ion pairs to be generated on the occasion of the electrostatic interaction with $RuO_4$, etc. become less soluble in the treatment liquid to form precipitates. The precipitates become particles which cause decrease in the yield rate of a semiconductor element. In addition, the larger the carbon number, the smaller the solubility in the treatment liquid becomes, and bubbles are more likely to be formed in the treatment liquid. On the other hand, when the carbon number is small, the interaction between the onium ion and $RuO_4^-$ etc. becomes weak, and therefore the $RuO_4$ gas inhibitory effect becomes weak. Therefore, the carbon numbers of the alkyl groups in Formula (2) or (3) are independently preferably from 1 to 25, more preferably from 2 to 10, and most preferably from 3 to 6. However, when $R^1$, $R^2$, $R^3$, and $R^4$ in Formula (2) are alkyl groups, the carbon number of at least one alkyl group among $R^1$, $R^2$, $R^3$, and $R^4$ may be 3 or more, and when $R^1$, $R^2$, and $R^3$ in Formula (3) are alkyl groups, the carbon number of at least one alkyl group among $R^1$, $R^2$, and $R^3$ can be 3 or more. When an onium salt has an alkyl group with such a carbon number, $RuO_4$ gas generation can be inhibited owing to the interaction with $RuO_4$, etc., and precipitates are less likely to be formed. Therefore, it can be suitably used as a treatment liquid for a semiconductor.

The aryl groups of $R^1$, $R^2$, $R^3$, and $R^4$ in Formula (2) or (3) independently include not only an aromatic hydrocarbon but also a heteroaryl having a heteroatom, and, although there is no particular restriction, a phenyl group or a naphthyl group is preferable.

There is no particular restriction on $X^-$ in Formula (2) or Formula (3), insofar as it is an anion, however a fluoride ion, a chloride ion, an iodide ion, a hydroxide ion, a nitrate ion, a phosphate ion, a sulfate ion, a hydrogen sulfate ion, a methanesulfate ion, a perchlorate ion, a chlorate ion, a chlorite ion, a hypochlorite ion, an orthoperiodate ion, a metaperiodate ion, an iodate ion, an iodite ion, a hypoiodite ion, an acetate ion, a carbonate ion, a hydrogencarbonate ion, a fluoroborate ion, or a trifluoroacetate ion is preferable.

As the mechanism by which the treatment liquid of the second aspect of the present invention inhibits a $RuO_4$ gas, the following is conceivable. That is, $RuO_4^-$ etc. generated by dissolution of ruthenium are trapped due to electrostatic interaction with onium ions. Since the trapped $RuO_4^-$ etc. are relatively stable in the treatment liquid as ion pairs, they are not easily transformed into $RuO_4$. As a result, $RuO_4$ gas generation is inhibited, and generation of $RuO_2$ particles is also inhibited.

The quaternary onium salt expressed by Formula (2) is a salt comprising an ammonium ion, or a phosphonium ion that can exist stably in the treatment liquid, namely an ammonium salt, or a phosphonium salt. In general, the alkyl chain length of an ammonium ion, or a phosphonium ion can be easily regulated, and an allyl group or an aryl group can be easily introduced. This makes it possible to regulate the size, symmetry, hydrophilicity, hydrophobicity, stability, solubility, charge density, surface active performance, etc. of the ammonium or phosphonium ion. Therefore, it is also possible to regulate the size, symmetry, hydrophilicity, hydrophobicity, stability, solubility, surface active performance, etc. of an ammonium salt or a phosphonium salt comprising the above ion. Such an ammonium salt or phosphonium salt can be used as the quaternary onium salt expressed by Formula (2) of a treatment liquid of the second aspect of the present invention.

The tertiary onium salt expressed by Formula (3) is a salt comprising a sulfonium ion that can exist stably in the treatment liquid, i.e., a sulfonium salt. In general, the alkyl chain length of a sulfonium ion can be easily regulated, and an allyl group or an aryl group can be easily introduced. This makes it possible to regulate the size, symmetry, hydrophilicity, hydrophobicity, stability, solubility, charge density, surface active performance, etc. of the sulfonium ion. Therefore, it is also possible to regulate the size, symmetry, hydrophilicity, hydrophobicity, stability, solubility, surface active performance, etc. of a sulfonium salt comprising the above ion. Such a sulfonium salt can be used as the tertiary onium salt expressed by Formula (3) of a treatment liquid of the second aspect of the present invention.

The above quaternary onium salt contained in the treatment liquid of the second aspect of the present invention is preferably an ammonium salt for reasons that the stability is high, and a high-purity industrial product thereof is easily and inexpensively available.

The above quaternary onium salt is preferably a tetraalkylammonium salt, which is particularly superior in stability, and can be easily synthesized. The tetraalkylammonium salt is more preferably a hydroxide or a halide.

Examples of a quaternary onium salt that can be suitably used in the second aspect of the present invention can include ammonium salts comprising a tetrapropylammonium ion, a tetrabutylammonium ion, a tetrapentylammonium ion, or a tetrahexylammonium ion. Furthermore, it is more preferable that these salts are hydroxides or halides. The treatment liquid containing any of these quaternary onium salts can inhibit a $RuO_4$ gas, especially in the processing of a semiconductor wafer, and can perform a treatment without generating $RuO_2$ particles.

The concentration of the onium salt in the treatment liquid of the second aspect of the present invention is preferably from 0.0001 to 50 mass %. When the addition amount of the onium salt is too small, not only the interaction with $RuO_4^-$ etc. is weakened and the $RuO_4$ gas inhibitory effect is reduced, but also the amount of $RuO_4^-$ etc. soluble in the treatment liquid is reduced, and as a result the number of reuse cycles of the treatment liquid is reduced. On the other hand, when the addition amount is too large, the amount of adsorbed onium salt on the ruthenium surface is increased which causes decrease in the dissolving rate of ruthenium, or uneven etching of the ruthenium surface. Therefore, the treatment liquid of the second aspect of the present invention preferably contains an onium salt at from 0.0001 to 50 mass %, more preferably from 0.01 to 35 mass %, and further preferably from 0.1 to 20 mass %. In this regard, in adding an onium salt, only one kind can be added, or a combination of two or more kinds can be added. Even when two or more kinds of onium salts are contained, if the total concentration of onium salts is within the above concentration range, $RuO_4$ gas generation can be effectively inhibited.

(Oxidizing Agent)

The treatment liquid of the second aspect of the present invention may contain an oxidizing agent. Examples of the oxidizing agent can include, but is not limited to, a halogen oxyacid, permanganic acid, and salts thereof, hydrogen peroxide, ozone, and a cerium (IV) salt. In this regard, a halogen oxyacid refers to hypochlorous acid, chlorous acid, chloric acid, perchloric acid, hypoiodous acid, iodous acid, iodic acid, metaperiodic acid, orthoperiodic acid, and the ions thereof. When the oxidizing agent is contained, not only dissolution of ruthenium is accelerated, but also redissolution of precipitated $RuO_2$ particles is accelerated. Therefore, a treatment liquid containing the onium salt and the oxidizing agent can efficiently treat a Ru-containing wafer, while inhibiting generation of $RuO_4$ gas and $RuO_2$ particles. Among the above oxidizing agents, a halogen oxyacid and its ion, or hydrogen peroxide are suitable as the oxidizing agent, because they can be used stably under an alkaline condition, and selection in a broad concentration range is possible. Hypochlorous acid, metaperiodic acid, orthoperiodic acid and ions thereof are more suitable, and hypochlorous acid and hypochlorite ions are most suitable.

When the treatment liquid of the second aspect of the present invention is a treatment liquid containing hypochlorite ions, the concentration of the hypochlorite ions is preferably in a range of 0.05 to 20.0 mass % with respect to the entire treatment liquid. Within the above range, it is possible to inhibit the decomposition reaction of hypochlorite ions in the treatment liquid, to inhibit decrease in the concentration of the hypochlorite ions, and to etch ruthenium at an etching rate of 20 Å/min or higher. Therefore, the concentration of hypochlorite ions is preferably in a range of 0.1 to 15 mass %, more preferably in a range of 0.3 to 10 mass %, further preferably in a range of 0.5 to 6 mass %, and especially preferably in a range of 0.5 to 4 mass %.

In the treatment liquid of the second aspect of the present invention, the balance component other than the onium salt, the organic solvent described in detail below, and other additives is water. The water contained in the treatment liquid of the second aspect of the present invention is preferably water from which metal ions, organic impurities, particles, etc. have been removed by distillation, an ion exchange treatment, a filtration treatment, various adsorption treatments, or the like, and especially pure water or ultrapure water is particularly preferable. Such water can be obtained by a publicly known method, which is widely used in semiconductor manufacturing.

(Organic Solvent)

As described above, in the second aspect of the present invention, $RuO_4$ gas generation is inhibited because $RuO_4^-$ etc. generated when ruthenium is dissolved are retained in the treatment liquid by electrostatic interaction with onium ions. In this case, $RuO_4^-$ etc. and onium ions are dissolved in the solution in the form of ion pairs, but if the solubility is exceeded, precipitates are formed. Since precipitates are a cause of particles in the semiconductor formation process, the decrease in the yield rate occurs. Therefore, it is important to prevent precipitation, preferably by increasing the solubility of the ion pairs. For this purpose, addition of an organic solvent is effective.

In general, when a solvent has a lower relative dielectric constant, it can dissolve more easily an electrically neutral chemical species. Also a solvent can dissolve more easily an electrically neutral ion pair, when it has a lower relative dielectric constant. Therefore, in order to increase the solubility of ion pairs, it is desirable to add an organic solvent with a relative dielectric constant lower than water (relative dielectric constant 78) as the organic solvent to be added to the treatment liquid of the second aspect of the present invention. In this way, the relative dielectric constant of the treatment liquid can be lowered compared to the case of water alone, and the solubility of ion pairs of the onium ions and $RuO_4^-$ etc. can be increased, so as to effectively inhibit $RuO_4$ gas generation. As such an organic solvent to be added, any organic solvent having a relative dielectric constant lower than water can be used, but the relative dielectric constant is preferably 45 or lower, more preferably 20 or lower, and further preferably 10 or lower. Note that these relative dielectric constants are values at 25° C.

Specific examples of such an organic solvent include sulfolane (relative dielectric constant 43), acetonitrile (relative dielectric constant 37), carbon tetrachloride (relative dielectric constant 2.2), and 1,4-dioxane (relative dielectric constant 2.2), however, of course, the organic solvent is not limited thereto.

When an organic solvent having a low relative dielectric constant is added, blending with water may be occasionally difficult. However, even in such a case, the organic solvent slightly dissolved in water can increase the solubility of the ion pairs, and therefore, the addition of the organic solvent is effective in inhibiting $RuO_4$ gas generation.

When an oxidizing agent is contained in a treatment liquid, it is preferable that the oxidizing agent and an organic solvent do not react with each other to prevent the organic solvent from being decomposed by the oxidizing agent, however any organic solvent can be used insofar as its reactivity with the oxidizing agent is low. For example, in a case where the oxidizing agent is a hypochlorite ion, a sulfolane, an alkyl nitrile, a halogenated alkane, or an ether can be suitably used as an organic solvent to be added to the treatment liquid of the second aspect of the present invention, because their reactivity with a hypochlorite ion is low. Specific examples of such an organic solvent include sulfolane, acetonitrile, carbon tetrachloride, and 1,4-dioxane, however, of course, the organic solvent is not limited thereto.

An organic solvent can be added in an amount as much as necessary to inhibit formation of precipitates. For this reason, the concentration of an organic solvent in the treatment liquid of the second aspect of the present invention is necessary to be 0.1 mass % or more, but in order to increase the dissolved amount of ion pairs so as to stably retain $RuO_4^-$, etc. as ion pairs in the solution, the concentration of an organic solvent is preferably 1 mass % or more. In addition, insofar as the solubility of ruthenium and the storage stability of the treatment liquid are not compromised, the addition amount of an organic solvent is preferably increased as much as possible, because there are many advantages such that the amount of ion pairs which can be dissolved in the treatment liquid increases to inhibit formation of precipitates, the inhibitory effect on a $RuO_4$ gas is not compromised, even when a small amount of organic solvent evaporates, and, when the treatment liquid is reused, $RuO_4$ gas generation can be still inhibited. One kind of organic solvents can be added, or a combination of plural kinds thereof can be added.

When a highly volatile solvent is used as the organic solvent, the organic solvent in the treatment liquid evaporates while treating a semiconductor wafer to change the concentration of the organic solvent, which changes the relative dielectric constant of the treatment liquid, making stable treatment difficult. Also, from the viewpoint of storage stability, an organic solvent with low volatility is preferable. Specifically, an organic solvents with a vapor pressure at 20° C. of 50 mmHg or less is preferable, and an organic solvent with a vapor pressure of 20 mmHg or less is more preferable.

The pH at 25° C. of the treatment liquid of the second aspect of the present invention is preferably 7 or more and 14 or less. When the pH of the treatment liquid is less than 7, the dissolution of ruthenium occurs not via anions of $RuO_4^-$, etc. but via $RuO_2$ or $Ru(OH)_3$, and therefore the effect of cation addition is reduced. Also, when the pH is less than 7, there arise problems that $RuO_2$ particles are more likely to be generated, and the generation amount of a $RuO_4$ gas increases. Therefore, in order for the treatment liquid of the second aspect of the present invention to fully demonstrate its ability to inhibit $RuO_4$ gas generation, the pH of the treatment liquid is preferably 7 or more and 14 or less, and more preferably 9 or more and 13 or less. In this pH range, the ruthenium dissolved in the treatment liquid exists as anions such as $RuO_4^-$ or $RuO_{42}$, and therefore it can easily form ion-pairs with the onium ions contained in the treatment liquid of the second aspect of the present invention to inhibit effectively $RuO_4$ gas generation.

(Other Additives)

Other additives conventionally used in a treatment liquid for semiconductors can be optionally added to a treatment liquid of the second aspect of the present invention, to the extent that the purpose of the present invention is not impaired. For example, an acid, a metal corrosion inhibitor, a water-soluble organic solvent, a fluorine compound, an oxidizing agent, a reducing agent, a complexing agent, a chelating agent, a surfactant, a defoaming agent, a pH adjuster, and a stabilizer can be added as other additives. These additives can be added singly or in combination of plural kinds.

Derived from such additives, or for reasons in manufacturing a treatment liquid, an alkali metal ion, an alkaline earth metal ion, etc. can be included in a treatment liquid of the second aspect of the present invention. For example, sodium ions, potassium ions, or calcium ions can be contained. However, when the alkali metal ion, alkaline earth metal ion, or the like remains on a semiconductor wafer, an adverse effect (adverse effect such as decrease in the yield rate of the semiconductor wafer) will be exerted on a semiconductor element. Therefore, the amount thereof should preferably be small, and most preferably it should be substantially not contained. Therefore, for example, as a pH adjuster, it is preferable to use an organic alkali such as ammonia, amine, choline, or tetraalkylammonium hydroxide, rather than an alkali metal hydroxide such as sodium hydroxide, or an alkaline earth metal hydroxide.

Specifically, the total amount of alkali metal ions and alkaline earth metal ions is preferably 1 mass % or less, more preferably 0.7 mass % or less, further preferably 0.3 mass % or less, especially preferably 10 ppm or less, and most preferably 500 ppb or less.

(Treatment Liquid of the Third Aspect)

The treatment liquid, etc. of the third aspect of the present invention will be described below.

The treatment liquid of the third aspect of the present invention is a treatment liquid that can treat a semiconductor wafer containing ruthenium without generating a $RuO_4$ gas. Therefore, the treatment liquid of the third aspect of the present invention is a treatment liquid that can be suitably used in a step of etching, a step of removing residues, a step of washing, a CMP step, etc. in a semiconductor manufacturing process.

The ruthenium in a semiconductor wafer to which the treatment liquid of the third aspect of the present invention is applied can be formed by any method. For film formation of ruthenium, a method publicly well known for a semiconductor manufacturing process, such as CVD, ALD, sputtering, and plating, cab be utilized. Such ruthenium can be metallic ruthenium, a ruthenium oxide, an alloy with another metal, an intermetallic compound, an ionic compound, or a complex. The ruthenium can be exposed on the surface of the wafer, or covered with another metal, a metal oxide film, an insulating film, a resist, or the like. Even in a case covered with another material, when ruthenium comes into contact with the treatment liquid and dissolution of ruthenium occurs, the onium salt contained in the treatment liquid of the third aspect of the present invention exerts the inhibitory effect on $RuO_4$ gas generation. Furthermore, in a case where ruthenium is not forced to be dissolved, in other words, in a treatment where ruthenium is the object of protection, the treatment liquid of the present invention is still capable of inhibiting a $RuO_4$ gas generated from a very small amount of dissolved ruthenium For example, in a case where the treatment liquid of the third aspect of the present invention is used in a step of forming a ruthenium wiring, the procedure is as follows. First, a substrate made of a semiconductor (e.g. Si) is prepared. The prepared substrate is subjected to an oxidation treatment to form a silicon oxide film on the substrate. Then, an interlayer insulating film constituted with a low dielectric constant (low-k) film is formed, and in which via holes are formed at predetermined intervals. After formation of via holes, the via holes are filled with ruthenium by thermal CVD, and a ruthenium film is further deposited thereon. The ruthenium film is etched using the treatment liquid of the present invention for planarization while inhibiting $RuO_4$ gas generation. By doing so, a highly reliable ruthenium wiring can be formed, while formation of $RuO_2$ particles can be inhibited.

The treatment liquid of the third aspect of the present invention comprises an onium salt. This will be described step by step below.

<Onium Salt>.

An onium salt is added to trap ions comprising a ruthenium atom ($RuO_4$, etc.) generated by dissolution of ruthenium, and is composed of an onium ion and an anion.

The onium ion is a compound of a polyatomic cation formed by addition of excess protons (hydrogen cations) to a monoatomic anion. The onium ion is a cation, such as an imidazolium ion, a pyrrolidinium ion, a pyridinium ion, a piperidinium ion, an ammonium ion, a phosphonium ion, a fluoronium ion, a chloronium ion, a bromonium ion, a iodonium ion, a oxonium ion, a sulfonium ion, a selenonium ion, a telluronium ion, an arsonium ion, a stibonium ion, and a bismuthonium ion; and an imidazolium ion, a pyrrolidinium ion, a pyridinium ion, a piperidinium ion, and an oxazolium ion are preferable.

An anion means a negatively charged ion, and can be an organic or inorganic anion. Although there is no particular restriction on an organic or an inorganic anion, a fluoride ion, a chloride ion, an iodide ion, a hydroxide ion, a nitrate ion, a phosphate ion, a sulfate ion, a hydrogen sulfate ion, a methanesulfate ion, a perchlorate ion, a chlorate ion, a chlorite ion, a hypochlorite ion, an orthoperiodate ion, a metaperiodate ion, an iodate ion, an iodite ion, a hypoiodite ion, an acetate ion, a carbonate ion, a hydrogencarbonate ion, a fluoroborate ion, a fluorophosphate ion, and a trifluoroacetate ion are preferable, and a hydroxide ion, a chloride ion, and a perchlorate ion are more preferable.

The above onium salts are expressed by the following Formula (4).

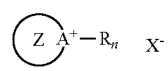

(4)

(In Formula (4), Z is an aromatic or an alicyclic group that may contain a nitrogen, sulfur, or oxygen atom, and in the aromatic group or alicyclic group, the carbon or nitrogen may have;

chlorine, bromine, fluorine, iodine, at least one alkyl group with a carbon number from 1 to 15, at least one alkenyloxy group with a carbon number from 2 to 9, an aromatic group that may be substituted with at least one alkyl group with a carbon number from 1 to 15, or an alicyclic group that may be substituted with at least one alkyl group with a carbon number from 1 to 15;

A is nitrogen or sulfur;

R is chlorine, bromine, fluorine, iodine, an alkyl group with a carbon number from 1 to 15, an allyl group, an aromatic group that may be substituted with at least one alkyl group with a carbon number from 1 to 15, or an alicyclic group that may be substituted with at least one alkyl group with a carbon number from 1 to 15;

$X^-$ is an organic or inorganic anion; and n is an integer of 1 or 2 and indicates the number of R, wherein when n is 2, R may be the same or different, and may form a ring.)

A cation having the above structure can exist stably in an alkaline semiconductor treatment liquid. Further, the solubility of an onium salt comprising the cation into the treatment liquid, and the stability of ion pairs between the cation and $RuO_4^-$, etc. can be controlled by replacing carbon or nitrogen in the aromatic group, or the alicyclic group of Z in Formula (4), with an aromatic group substituted with an alkyl group, or an alkenyloxy group, having a suitable carbon number, or an alicyclic group substituted with an alkyl group, or by appropriately selecting an alkyl group, an allyl group, an aromatic group which may be substituted with an alkyl group, or an alicyclic group which may be substituted with an alkyl group as R.

Although there is no particular restriction on X⁻ in Formula (4), insofar as it is an organic or inorganic anion, a fluoride ion, a chloride ion, an iodide ion, a hydroxide ion, a nitrate ion, a phosphate ion, a sulfate ion, a hydrogen sulfate ion, a methanesulfate ion, a perchlorate ion, a chlorate ion, a chlorite ion, a hypochlorite ion, an orthoperiodate ion, a metaperiodate ion, an iodate ion, an iodite ion, a hypoiodite ion, an acetate ion, a carbonate ion, a hydrogencarbonate ion, a fluoroborate ion, a fluorophosphate ion, and a trifluoroacetate ion are preferable, and a hydroxide ion, and a chloride ion are more preferable.

Specific examples of an onium salt expressed by Formula (4) that can be suitably used in the present invention may include 1,3-dimethylimidazolium chloride, 1-butyl-3-methylimidazolium chloride, 1-butyl-2,3-dimethylimidazolium chloride, 1-hexyl-3-methylimidazolium chloride, 1-methyl-3-n-octylimidazolium chloride, 1,3-dimesitylimidazolium chloride, 1,3-bis(2,6-diisopropylphenyl)imidazolium chloride, 1,3-dicyclohexylimidazolium chloride, 1-butyl-1-methylpyrrolidinium chloride, 1-ethyl-1-methylpyrrolidinium chloride, 1,1-dimethylpiperidinium chloride, 1-butyl-1-methylpiperidinium chloride, 5-azoniaspiro[4,4]nonane chloride, 1-methylpyridinium chloride, 1-ethylpyridinium chloride, 1-propylpyridinium chloride, 1-fluoropyridinium tetrafluoroborate, 1-fluoro-2,4,6-trimethylpyridinium tetrafluoroborate, 1-fluoro-2,6-dichloropyridinium tetrafluoroborate, and N-tert-butyl-5-methylisoxazolium perchlorate.

As the mechanism by which the treatment liquid of the third aspect of the present invention inhibits a $RuO_4$ gas, the following is conceivable. That is, $RuO_4^-$ etc. generated by dissolution of ruthenium are trapped due to electrostatic interaction with onium ions. Since the trapped $RuO_4^-$ etc. are relatively stable in the treatment liquid as ion pairs, they are not easily transformed into $RuO_4$. As a result, $RuO_4$ gas generation is inhibited, and generation of $RuO_2$ particles is also inhibited.

The concentration of the onium salt in the treatment liquid of the third aspect of the present invention is preferably from 0.0001 to 50 mass %. When the addition amount of the onium salt is too small, not only the interaction with $RuO_4^-$ etc. is weakened and the $RuO_4$ gas inhibitory effect is reduced, but also the amount of $RuO_4^-$ etc. soluble in the treatment liquid is reduced, and as a result the number of reuse cycles of the treatment liquid is reduced. On the other hand, when the addition amount is too large, the amount of adsorbed onium salt on the ruthenium surface is increased which causes decrease in the dissolving rate of ruthenium, or uneven etching of the ruthenium surface. Therefore, the treatment liquid of the third aspect of the present invention preferably contains an onium salt at from 0.0001 to 50 mass %, more preferably from 0.01 to 35 mass %, and further preferably from 0.1 to 20 mass %. In this regard, in adding an onium salt, only one kind can be added, or a combination of two or more kinds can be added. Even when two or more kinds of onium salts are contained, if the total concentration of onium salts is within the above concentration range, $RuO_4$ gas generation can be effectively inhibited.

(Oxidizing Agent)

The treatment liquid of the third aspect of the present invention can contain an oxidizing agent. Examples of the oxidizing agent can include, but is not limited to, a halogen oxyacid, permanganic acid, and salts thereof, hydrogen peroxide, ozone, and a cerium (IV) salt. In this regard, a halogen oxyacid refers to hypochlorous acid, chlorous acid, chloric acid, perchloric acid, hypoiodous acid, iodous acid, iodic acid, metaperiodic acid, orthoperiodic acid, and the ions thereof. When the oxidizing agent is contained, not only dissolution of ruthenium is accelerated, but also redissolution of precipitated $RuO_2$ particles is accelerated. Therefore, a treatment liquid containing the onium salt and the oxidizing agent can efficiently treat a Ru-containing wafer, while inhibiting generation of $RuO_4$ gas and $RuO_2$ particles. Among the above oxidizing agents, a halogen oxyacid and its ion, or hydrogen peroxide are suitable as the oxidizing agent, because they can be used stably under an alkaline condition, and selection in a broad concentration range is possible. Hypochlorous acid, metaperiodic acid, orthoperiodic acid and ions thereof are more suitable, and hypochlorous acid and hypochlorite ions are most suitable. The oxidizing agent can be present as a salt in the treatment liquid, and as the salt, for example, a tetraalkylammonium hypochlorite is suitable, and tetramethylammonium hypochlorite is more suitable.

When the treatment liquid of the third aspect of the present invention is a treatment liquid containing hypochlorite ions, the concentration of the hypochlorite ions is preferably in a range of 0.05 to 20.0 mass % with respect to the entire treatment liquid. Within the above range, it is possible to inhibit the decomposition reaction of hypochlorite ions in the treatment liquid, to inhibit decrease in the concentration of the hypochlorite ions, and to etch ruthenium at an etching rate of 20 Å/min or higher. Therefore, the concentration of hypochlorite ions is preferably in a range of 0.1 to 15 mass %, more preferably in a range of 0.3 to 10 mass %, further preferably in a range of 0.5 to 6 mass %, and especially preferably in a range of 0.5 to 4 mass %.

In the treatment liquid of the third aspect of the present invention, the balance component other than the onium salt, the organic solvent described in detail below, and other additives is water. The water contained in the treatment liquid of the present invention is preferably water from which metal ions, organic impurities, particles, etc. have been removed by distillation, an ion exchange treatment, a filtration treatment, various adsorption treatments, or the like, and especially pure water or ultrapure water is particularly preferable. Such water can be obtained by a publicly known method, which is widely used in semiconductor manufacturing.

(Organic Solvent)

As described above, in the third aspect of the present invention, $RuO_4$ gas generation is inhibited because $RuO_4^-$ etc. generated when ruthenium is dissolved are retained in the treatment liquid by electrostatic interaction with onium ions. In this case, $RuO_4^-$ etc. and onium ions are dissolved in the solution in the form of ion pairs, but if the solubility is exceeded, precipitates are formed. Since precipitates are a cause of particles in the semiconductor formation process, the decrease in the yield rate occurs. Therefore, it is important to prevent precipitation, preferably by increasing the solubility of the ion pairs. For this purpose, addition of an organic solvent is effective.

In general, when a solvent has a lower relative dielectric constant, it can dissolve more easily an electrically neutral chemical species. Also a solvent can dissolve more easily an electrically neutral ion pair, when it has a lower relative dielectric constant. Therefore, in order to increase the solubility of ion pairs, it is desirable to add an organic solvent with a relative dielectric constant lower than water (relative dielectric constant 78) as the organic solvent to be added to the treatment liquid of the present invention. In this way, the relative dielectric constant of the treatment liquid can be lowered compared to the case of water alone, and the solubility of ion pairs of the onium ions and $RuO_4^-$ etc. can be increased, so as to effectively inhibit $RuO_4$ gas generation. As such an organic solvent to be added, any organic solvent having a relative dielectric constant lower than water can be used, but the relative dielectric constant is preferably 45 or lower, more preferably 20 or lower, and further preferably 10 or lower. Note that these relative dielectric constants are values at 25° C.

Specific examples of such an organic solvent include sulfolane (relative dielectric constant 43), acetonitrile (relative dielectric constant 37), carbon tetrachloride (relative dielectric constant 2.2), and 1,4-dioxane (relative dielectric constant 2.2), however, of course, the organic solvent is not limited thereto.

When an organic solvent having a low relative dielectric constant is added, blending with water may be occasionally difficult. However, even in such a case, the organic solvent slightly dissolved in water can increase the solubility of the ion pairs, and therefore, the addition of the organic solvent is effective in inhibiting $RuO_4$ gas generation.

When an oxidizing agent is contained in a treatment liquid, it is preferable that the oxidizing agent and an organic solvent do not react with each other to prevent the organic solvent from being decomposed by the oxidizing agent, however any organic solvent can be used insofar as its reactivity with the oxidizing agent is low. For example, in a case where the oxidizing agent is a hypochlorite ion, a sulfolane, an alkyl nitrile, a halogenated alkane, or an ether can be suitably used as an organic solvent to be added to the treatment liquid, because their reactivity with a hypochlorite ion is low. Specific examples of such an organic solvent include sulfolane, acetonitrile, carbon tetrachloride, and 1,4-dioxane, however, of course, the organic solvent is not limited thereto.

An organic solvent can be added in an amount as much as necessary to inhibit formation of precipitates. For this reason, the concentration of an organic solvent in the treatment liquid is necessary to be 0.1 mass % or more, but in order to increase the dissolved amount of ion pairs so as to stably retain $RuO_4$, etc. as ion pairs in the solution, the concentration of an organic solvent is preferably 1 mass % or more. In addition, insofar as the solubility of ruthenium and the storage stability of the treatment liquid are not compromised, the addition amount of an organic solvent is preferably increased as much as possible. Because there are many advantages such that the amount of ion pairs which can be dissolved in the treatment liquid increases to inhibit formation of precipitates, the inhibitory effect on a $RuO_4$ gas is not compromised, even when a small amount of organic solvent evaporates, and, when the treatment liquid is reused, $RuO_4$ gas generation can be still inhibited. One kind of organic solvents can be added, or a combination of plural kinds thereof can be added.

When a highly volatile solvent is used as the organic solvent, the organic solvent in the treatment liquid evaporates while treating a semiconductor wafer to change the concentration of the organic solvent, which changes the relative dielectric constant of the treatment liquid, making stable treatment difficult. Also, from the viewpoint of storage stability, an organic solvent with low volatility is preferable. Specifically, an organic solvents with a vapor pressure at 20° C. of 50 mmHg or less is preferable, and an organic solvent with a vapor pressure at 20° C. of 20 mmHg or less is more preferable.

The pH at 25° C. of the treatment liquid of the third aspect of the present invention is preferably 7 or more and 14 or less. When the pH of the treatment liquid is less than 7, the dissolution of ruthenium occurs not via anions of $RuO_4$, etc. but via $RuO_2$ or $Ru(OH)_3$, and therefore the effect of cation addition is reduced. Also, when the pH is less than 7, there arise problems that $RuO_2$ particles are more likely to be generated, and the generation amount of a $RuO_4$ gas increases. Therefore, in order for the treatment liquid of the third aspect of the present invention to fully demonstrate its ability to inhibit $RuO_4$ gas generation, the pH of the treatment liquid is preferably 7 or more and 14 or less, and more preferably 9 or more and 13 or less. In this pH range, the ruthenium dissolved in the treatment liquid exists as anions such as $RuO_4^-$ or $RuO_4^{2-}$, and therefore it can easily form ion-pairs with the onium ions contained in the treatment liquid of the present invention to inhibit effectively $RuO_4$ gas generation.

(Other Additives)

Other additives conventionally used in a treatment liquid for semiconductors can be optionally added to a treatment liquid of the third aspect of the present invention, to the extent that the purpose of the present invention is not impaired. For example, an acid, a metal corrosion inhibitor, a water-soluble organic solvent, a fluorine compound, an oxidizing agent, a reducing agent, a complexing agent, a chelating agent, a surfactant, a defoaming agent, a pH adjuster, and a stabilizer can be added as other additives. These additives can be added singly or in combination of plural kinds.

Derived from such additives, or for reasons in manufacturing a treatment liquid, an alkali metal ion, an alkaline earth metal ion, etc. can be included in a treatment liquid of the third aspect of the present invention. For example, sodium ions, potassium ions, or calcium ions can be contained. However, when the alkali metal ion, alkaline earth metal ion, or the like remains on a semiconductor wafer, an adverse effect (adverse effect such as decrease in the yield rate of the semiconductor wafer) will be exerted on a semiconductor element. Therefore, the amount thereof should preferably be small, and most preferably it should be substantially not contained. Therefore, for example, as a pH adjuster, it is preferable to use an organic alkali such as ammonia, amine, choline, or tetraalkylammonium hydroxide, rather than an alkali metal hydroxide such as sodium hydroxide, or an alkaline earth metal hydroxide.

Specifically, the total amount of alkali metal ions and alkaline earth metal ions is preferably 1 mass % or less, more preferably 0.7 mass % or less, further preferably 0.3 mass % or less, especially preferably 10 ppm or less, and most preferably 500 ppb or less.

(Treatment Liquid of the Fourth Aspect)

The treatment liquid, etc. of the fourth aspect of the present invention will be described below.

The treatment liquid of the fourth aspect of the present invention is a treatment liquid that can treat a semiconductor wafer containing ruthenium without generating a $RuO_4$ gas. Therefore, the treatment liquid of the fourth aspect of the present invention is a treatment liquid that can be suitably used in a step of etching, a step of removing residues, a step of washing, a CMP step, etc. in a semiconductor manufacturing process.

The ruthenium in a semiconductor wafer to which the treatment liquid of the fourth aspect of the present invention is applied can be formed by any method. For film formation of ruthenium, a method publicly well known for a semiconductor manufacturing process, such as CVD, ALD, sputtering, and plating, can be utilized. Such ruthenium can be metallic ruthenium, a ruthenium oxide, an alloy with another metal, an intermetallic compound, an ionic compound, or a complex. The ruthenium can be exposed on the surface of the wafer, or covered with another metal, a metal oxide film, an insulating film, a resist, or the like. Even in a case covered with another material, when ruthenium comes into contact with the treatment liquid and dissolution of ruthenium occurs, the onium salt contained in the treatment liquid of the fourth aspect of the present invention exerts the inhibitory effect on $RuO_4$ gas generation. Furthermore, in a case where ruthenium is not forced to be dissolved, in other words, in a treatment where ruthenium is the object of protection, the treatment liquid of the fourth aspect of the present invention is still capable of inhibiting a $RuO_4$ gas generated from a very small amount of dissolved ruthenium For example, in a case where the treatment liquid of the fourth aspect of the present invention is used in a step of forming a ruthenium wiring, $RuO_2$ particles are inhibited by the same procedure and operation as the case of using the treatment liquid of the second aspect of the present invention described above, so that a highly reliable ruthenium wiring can be formed.

The treatment liquid of the fourth aspect of the present invention comprises an onium salt consisting of an onium ion and an anion. This will be described step by step below.

The above onium salt is represented by the following Formula (5).

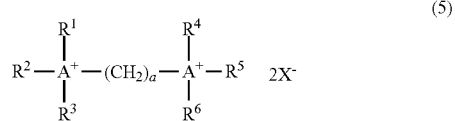

(In Formula (5), $A^+$ are independently an ammonium ion, or a phosphonium ion; and $R^1$, $R^2$, $R^3$, $R^4$, $R^5$, and $R^6$ are independently an alkyl group with a carbon number from 1 to 25, an allyl group, an aralkyl group having an alkyl group with a carbon number from 1 to 25, or an aryl group. At least one hydrogen in a ring of an aryl group in the aralkyl group, or the aryl group may be replaced with fluorine, chlorine, an alkyl group with a carbon number from 1 to 10, an alkenyl group with a carbon number from 2 to 10, an alkoxy group with a carbon number from 1 to 9, or an alkenyloxy group with a carbon number from 2 to 9; and in these groups, at least one hydrogen may be replaced with fluorine or chlorine. In Formula (5), $X^-$ is a fluoride ion, a chloride ion, an iodide ion, a hydroxide ion, a nitrate ion, a phosphate ion, a sulfate ion, a hydrogen sulfate ion, a methanesulfate ion, a perchlorate ion, a chlorate ion, a chlorite ion, a hypochlorite ion, an orthoperiodate ion, a metaperiodate ion, an iodate ion, an iodite ion, a hypoiodite ion, an acetate ion, a carbonate ion, a hydrogencarbonate ion, a fluoroborate ion, or a trifluoroacetate ion; and a is an integer of 1 to 10.)

The alkyl groups of $R^1$, $R^2$, $R^3$, $R^4$, $R^5$, and $R^6$ in Formula (5) can be used without any particular restriction insofar as the carbon numbers are independently from 1 to 25. The larger the carbon number, the stronger the interaction of the onium ion with $RuO_4$, etc. becomes, and the more easily the $RuO_4$ gas is inhibited. On the other hand, the larger the carbon number, the bulkier the onium ion becomes, and therefore ion pairs to be generated on the occasion of the electrostatic interaction with $RuO_4^-$, etc. become less soluble in the treatment liquid to form precipitates. The precipitates become particles which cause decrease in the yield rate of a semiconductor element. In addition, the larger the carbon number, the smaller the solubility in the treatment liquid becomes, and bubbles are more likely to be formed in the treatment liquid. On the other hand, when the carbon number is small, the interaction between the onium ion and $RuO_4^-$ etc. becomes weak, and therefore the $RuO_4$ gas inhibitory effect becomes weak. Therefore, the carbon numbers of the alkyl groups in Formula (5) are independently preferably from 1 to 25, more preferably from 2 to 10, and most preferably from 3 to 6. When an onium salt has an alkyl group with such a carbon number, $RuO_4$ gas generation can be inhibited owing to the interaction with $RuO_4$, etc., and precipitates are less likely to be formed. Therefore, it can be suitably used as a treatment liquid for a semiconductor.

The aryl groups of $R^1$, $R^2$, $R^3$, $R^4$, $R^5$, and $R^6$ in Formula (5) independently include not only an aromatic hydrocarbon but also a heteroaryl having a heteroatom, and, although there is no particular restriction, a phenyl group or a naphthyl group is preferable.

There is no particular restriction on $X^-$ in Formula (5), insofar as it is an anion, however a fluoride ion, a chloride ion, an iodide ion, a hydroxide ion, a nitrate ion, a phosphate ion, a sulfate ion, a hydrogen sulfate ion, a methanesulfate ion, a perchlorate ion, a chlorate ion, a chlorite ion, a hypochlorite ion, an orthoperiodate ion, a metaperiodate ion, an iodate ion, an iodite ion, a hypoiodite ion, an acetate ion, a carbonate ion, a hydrogencarbonate ion, a fluoroborate ion, or a trifluoroacetate ion is preferable.

As the mechanism by which the treatment liquid of the fourth aspect of the present invention inhibits a $RuO_4$ gas, the following is conceivable. That is, $RuO_4^-$ etc. generated by dissolution of ruthenium are trapped due to electrostatic interaction with onium ions. Since the trapped $RuO_4^-$ etc. are relatively stable in the treatment liquid as ion pairs, they are not easily transformed into $RuO_4$. As a result, $RuO_4$ gas generation is inhibited, and generation of $RuO_2$ particles is also inhibited.

The onium salt expressed by Formula (5) is a salt comprising an ammonium ion, or a phosphonium ion that can exist stably in the treatment liquid, namely an ammonium salt, or a phosphonium salt. In general, the alkyl chain length of an ammonium ion, or a phosphonium ion can be easily regulated, and an allyl group or an aryl group can be easily introduced. This makes it possible to regulate the size, symmetry, hydrophilicity, hydrophobicity, stability, solubility, charge density, surface active performance, etc. of the ammonium or phosphonium ion. Therefore, it is also possible to regulate the size, symmetry, hydrophilicity, hydrophobicity, stability, solubility, surface active performance, etc. of an ammonium salt or a phosphonium salt comprising the above ion.

The onium salt expressed by Formula (5) contained in the treatment liquid of the second aspect of the present invention is preferably an ammonium salt for reasons that the stability is high, a high-purity industrial product thereof is easily and inexpensively available.

The onium salt expressed by Formula (5) is preferably a hexamethonium salt, or a decamethonium salt, which are particularly superior in stability, and can be easily synthesized. The hexamethonium salt and decamethonium salt is more preferably a hydroxide or a halide.

Examples of an onium salt that can be suitably used in the fourth aspect of the present invention can include a methonium salt selected from hexamethonium chloride, and decamethonium iodide. Furthermore, it is more preferable that these salts are hydroxides or halides. The treatment liquid containing any of these onium salts can inhibit a $RuO_4$ gas, especially in treating a semiconductor wafer, and can perform a treatment without generating $RuO_2$ particles.

The concentration of the onium salt in the treatment liquid of the fourth aspect of the present invention is preferably from 0.0001 to 50 mass %. When the addition amount of the onium salt is too small, not only the interaction with $RuO_4^-$ etc. is weakened and the $RuO_4$ gas inhibitory effect is reduced, but also the amount of $RuO_4^-$ etc. soluble in the treatment liquid is reduced, and as a result the number of reuse cycles of the treatment liquid is reduced. On the other hand, when the addition amount is too large, the amount of adsorbed onium salt on the ruthenium surface is increased which causes decrease in the dissolving rate of ruthenium, or uneven etching of the ruthenium surface. Therefore, the treatment liquid of the second aspect of the present invention preferably contains an onium salt at from 0.0001 to 50 mass %, more preferably from 0.01 to 40 mass %, and further preferably from 0.1 to 30 mass %. In this regard, in adding an onium salt, only one kind can be added, or a combination of two or more kinds can be added. Even when two or more kinds of onium salts are contained, if the total concentration of onium salts is within the above concentration range, $RuO_4$ gas generation can be effectively inhibited.

(Oxidizing Agent)

The treatment liquid of the fourth aspect of the present invention may contain an oxidizing agent. Examples of the oxidizing agent can include, but is not limited to, a halogen oxyacid, permanganic acid, and salts thereof, hydrogen peroxide, ozone, and a cerium (IV) salt. In this regard, a halogen oxyacid refers to hypochlorous acid, chlorous acid, chloric acid, perchloric acid, hypoiodous acid, iodous acid, iodic acid, metaperiodic acid, orthoperiodic acid, and the ions thereof. When the oxidizing agent is contained, not only dissolution of ruthenium is accelerated, but also redissolution of precipitated $RuO_2$ particles is accelerated. Therefore, a treatment liquid containing the onium salt and the oxidizing agent can efficiently treat a Ru-containing wafer, while inhibiting generation of $RuO_4$ and $RuO_2$ particles. Among the above oxidizing agents, a halogen oxyacid and its ion, or hydrogen peroxide are suitable as the oxidizing agent, because they can be used stably under an alkaline condition, and selection in a broad concentration range is possible. Hypochlorous acid, metaperiodic acid, orthoperiodic acid and ions thereof are more suitable, and hypochlorous acid and hypochlorite ions are most suitable.

When the treatment liquid of the fourth aspect of the present invention is a treatment liquid containing hypochlorite ions, the concentration of the hypochlorite ions is preferably in a range of 0.05 to 20.0 mass % with respect to the entire treatment liquid. Within the above range, it is possible to inhibit the decomposition reaction of hypochlorite ions in the treatment liquid, to inhibit decrease in the concentration of the hypochlorite ions, and to etch ruthenium at an etching rate of 20 Å/min or higher. Therefore, the concentration of hypochlorite ions is preferably in a range of 0.1 to 15 mass %, more preferably in a range of 0.3 to 10 mass %, further preferably in a range of 0.5 to 6 mass %, and especially preferably in a range of 0.5 to 4 mass %.

In the treatment liquid of the fourth aspect of the present invention, the balance component other than the onium salt, the organic solvent described in detail below, and other additives is water. The water contained in the treatment liquid of the fourth aspect of the present invention is preferably water from which metal ions, organic impurities, particles, etc. have been removed by distillation, an ion exchange treatment, a filtration treatment, various adsorption treatments, or the like, and especially pure water or ultrapure water is particularly preferable. Such water can be obtained by a publicly known method, which is widely used in semiconductor manufacturing.

(Organic Solvent)

As described above, in the fourth aspect of the present invention, $RuO_4$ gas generation is inhibited because $RuO_4^-$ etc. generated when ruthenium is dissolved are retained in the treatment liquid by electrostatic interaction with onium ions. In this case, $RuO_4^-$ etc. and onium ions are dissolved in the solution in the form of ion pairs, but if the solubility is exceeded, precipitates are formed. Since precipitates are a cause of particles in the semiconductor formation process, the decrease in the yield rate occurs. Therefore, it is important to prevent precipitation, preferably by increasing the solubility of the ion pairs. For this purpose, addition of an organic solvent is effective.

In general, when a solvent has a lower relative dielectric constant, it can dissolve more easily an electrically neutral chemical species. Also a solvent can dissolve more easily an electrically neutral ion pair, when it has a lower relative dielectric constant. Therefore, in order to increase the solubility of ion pairs, it is desirable to add an organic solvent with a relative dielectric constant lower than water (relative dielectric constant 78) as the organic solvent to be added to the treatment liquid of the fourth aspect of the present invention. In this way, the relative dielectric constant of the treatment liquid can be lowered compared to the case of water alone, and the solubility of ion pairs of the onium ions and $RuO_4^-$ etc. can be increased, so as to effectively inhibit $RuO_4$ gas generation. As such an organic solvent to be added, any organic solvent having a relative dielectric constant lower than water can be used, but the relative dielectric constant is preferably 45 or lower, more preferably 20 or lower, and further preferably 10 or lower. Note that these relative dielectric constants are values at 25° C.

Specific examples of such an organic solvent include sulfolane (relative dielectric constant 43), acetonitrile (relative dielectric constant 37), carbon tetrachloride (relative dielectric constant 2.2), and 1,4-dioxane (relative dielectric constant 2.2), however, of course, the organic solvent is not limited thereto.

When an organic solvent having a low relative dielectric constant is added, blending with water may be occasionally difficult. However, even in such a case, the organic solvent slightly dissolved in water can increase the solubility of the ion pairs, and the addition of the organic solvent is effective in inhibiting $RuO_4$ gas generation.

When an oxidizing agent is contained in a treatment liquid, it is preferable that the oxidizing agent and an organic solvent do not react with each other to prevent the organic solvent from being decomposed by the oxidizing agent, however any organic solvent can be used insofar as its reactivity with the oxidizing agent is low. For example, in a case where the oxidizing agent is a hypochlorite ion, a sulfolane, an alkyl nitrile, a halogenated alkane, or an ether can be suitably used as an organic solvent to be added to the treatment liquid of the fourth aspect of the present invention, because their reactivity with a hypochlorite ion is low. Specific examples of such an organic solvent include sulfolane, acetonitrile, carbon tetrachloride, and 1,4-dioxane, however, of course, the organic solvent is not limited thereto.

An organic solvent can be added in an amount as much as necessary to inhibit formation of precipitates. For this reason, the concentration of an organic solvent in the treatment liquid of the fourth aspect of the present invention is necessary to be 0.1 mass % or more, but in order to increase the dissolved amount of ion pairs so as to stably retain $RuO_4$, etc. as ion pairs in the solution, the concentration of an organic solvent is preferably 1 mass % or more. In addition, insofar as the solubility of ruthenium and the storage stability of the treatment liquid are not compromised, the addition amount of an organic solvent is preferably increased as much as possible. Because there are many advantages such that the amount of ion pairs which can be dissolved in the treatment liquid increases to inhibit formation of precipitates, the inhibitory effect on a $RuO_4$ gas is not compromised, even when a small amount of organic solvent evaporates, and, when the treatment liquid is reused, $RuO_4$ gas generation can be still inhibited. One kind of organic solvents can be added, or a combination of plural kinds thereof can be added.

When a highly volatile solvent is used as the organic solvent, the organic solvent in the treatment liquid evaporates while treating a semiconductor wafer to change the concentration of the organic solvent, which changes the relative dielectric constant of the treatment liquid, making stable treatment difficult. Also, from the viewpoint of storage stability, an organic solvent with low volatility is preferable. Specifically, an organic solvent with a vapor pressure at 20° C. of 50 mmHg or less is preferable, and an organic solvent with a vapor pressure at 20° C. of 20 mmHg or less is more preferable.

The pH at 25° C. of the treatment liquid of the fourth aspect of the present invention is preferably 7 or more and 14 or less. When the pH of the treatment liquid is less than 7, the dissolution of ruthenium occurs not via anions of $RuO_4$, etc. but via $RuO_2$ or $Ru(OH)_3$, and therefore the effect of cation addition is reduced. Also, when the pH is less than 7, there arise problems that $RuO_2$ particles are more likely to be generated, and the generation amount of a $RuO_4$ gas increases. Therefore, in order for the treatment liquid of the fourth aspect of the present invention to fully demonstrate its ability to inhibit $RuO_4$ gas generation, the pH of the treatment liquid is preferably 7 or more and 14 or less, and more preferably 9 or more and 13 or less. In this pH range, the ruthenium dissolved in the treatment liquid exists as anions such as $RuO_4^-$ or $RuO_4^{2-}$, and therefore it can easily form ion-pairs with the onium ions contained in the treatment liquid of the fourth aspect of the present invention to inhibit effectively $RuO_4$ gas generation.

(Other Additives)

Other additives conventionally used in a treatment liquid for semiconductors can be optionally added to a treatment liquid of the fourth aspect of the present invention, to the extent that the purpose of the present invention is not impaired. For example, an acid, a metal corrosion inhibitor, a water-soluble organic solvent, a fluorine compound, an oxidizing agent, a reducing agent, a complexing agent, a chelating agent, a surfactant, a defoaming agent, a pH adjuster, and a stabilizer can be added as other additives. These additives can be added singly or in combination of plural kinds.

Derived from such additives, or for reasons in manufacturing a treatment liquid, an alkali metal ion, an alkaline earth metal ion, etc. can be included in a treatment liquid of the fourth aspect of the present invention. For example, sodium ions, potassium ions, or calcium ions can be contained. However, when the alkali metal ion, alkaline earth metal ion, or the like remains on a semiconductor wafer, an adverse effect (adverse effect such as decrease in the yield rate of the semiconductor element) will be exerted on a semiconductor element. Therefore, the amount thereof should preferably be small, and most preferably it should be substantially not contained. Therefore, for example, as a pH adjuster, it is preferable to use an organic alkali such as ammonia, amine, choline, or tetraalkylammonium hydroxide, rather than an alkali metal hydroxide such as sodium hydroxide, or an alkaline earth metal hydroxide.

Specifically, the total amount of alkali metal ions and alkaline earth metal ions is preferably 1 mass % or less, more preferably 0.7 mass % or less, further preferably 0.3 mass % or less, especially preferably 10 ppm or less, and most preferably 500 ppb or less.

(Inhibitor for Ruthenium-Containing Gas Generation)

The inhibitor for ruthenium-containing gas generation is a liquid containing an onium salt expressed by any of Formulas (2) to (5), which inhibits generation of a ruthenium-containing gas when it is added to a liquid for treating ruthenium.

There is no particular restriction on the liquid for treating ruthenium, insofar as the same contains a component which causes a physical or chemical change to ruthenium when the same is brought into contact with the ruthenium, examples thereof include a solution containing an oxidizing agent. Examples of the oxidizing agent include those oxidizing agents mentioned in connection with the treatment liquid of the second aspect of the present invention, the treatment liquid of the third aspect, and the treatment liquid of the fourth aspect. The ruthenium treated with a liquid for treating ruthenium entirely or partly dissolves, disperses, or precipitates in the treatment liquid, and thereby can cause generation of $RuO_4$ (gas) and/or $RuO_2$ (particles).

With the liquid comprising a liquid for treating ruthenium and an inhibitor for ruthenium-containing gas generation of the present invention (also referred to as a "treatment liquid containing inhibitor for gas generation"), $RuO_4^-$, etc. present in the treatment liquid and an onium ion form an ion pair soluble in the treatment liquid, so that the generation of $RuO_4$ (gas) and $RuO_2$ (particles) from $RuO_4^-$ etc. is inhibited. This is because $RuO_4$ (gas) formed from $RuO_4$ (solution) is substantially reduced, and formation of $RuO_2$ (particles) from $RuO_4$ (gas) is suppressed.

Since, as described above, each of the treatment liquid of the second aspect, the treatment liquid of the third aspect, and the treatment liquid of the fourth aspect of the present invention comprises any of the onium salts expressed by Formulas (2) to (5), it is a treatment liquid with which a semiconductor wafer containing ruthenium can be treated without generating a $RuO_4$ gas. In other words, each of the treatment liquid of the second aspect, the treatment liquid of the third aspect, and the treatment liquid of the fourth aspect of the present invention is a liquid for treating ruthenium, and at the same time an inhibitor for ruthenium-containing gas generation. Therefore the treatment liquids of these aspects can be used as an inhibitor for ruthenium-containing gas generation.

The conditions with respect to the inhibitor for ruthenium-containing gas generation, such as the kind and content of any of the onium salts expressed by Formulas (2) to (5), other components and the contents thereof, and the pH of the inhibitor for ruthenium-containing gas generation can use the same conditions as those described in connection with the treatment liquid for a semiconductor wafer of each aspect.

In addition to these conditions, for example, the content of any of the onium salts expressed by Formulas (2) to (5) in an inhibitor for ruthenium-containing gas generation is from 0.0001 to 50 mass %, more preferably from 0.01 to 35 mass %, and further preferably from 0.1 to 20 mass %. As described later, this concentration can be adjusted such that the concentration of the onium salt in the liquid mixture which is mixed with an object liquid for which generation of a ruthenium-containing gas is inhibited, namely the liquid for treating ruthenium, reaches a predetermined value. Further, a pH adjuster identical with those described above in the second through fourth aspects can be added as appropriate to the inhibitor for ruthenium-containing gas generation. The content of the pH adjuster can be adjusted such that the pH of the mixed liquid which is mixed with the liquid for treating ruthenium falls within the predetermined range as described below. For example, the content of a pH adjuster in an inhibitor for ruthenium-containing gas generation is required to reach an effective amount, specifically it is, for example, from 0.000001 to 10 mass %.

(Method for Inhibiting Ruthenium-Containing Gas Generation)

The method for inhibiting ruthenium-containing gas generation is a method for inhibiting ruthenium-containing gas generation comprising a step of adding the aforedescribed inhibitor for ruthenium-containing gas generation to a liquid for treating ruthenium. Specifically, the ruthenium-containing gas generation can be inhibited by adding an inhibitor for ruthenium-containing gas generation of the present invention to a liquid (a liquid for treating ruthenium) used in the steps of treating ruthenium, such as the etching step, residue removal step, washing step, and CMP step, in a semiconductor manufacturing process. In addition, the ruthenium-containing gas generation can be inhibited by using the inhibitor for ruthenium-containing gas generation, when ruthenium adhered to chamber inner walls, piping, etc. of each equipment used in the semiconductor manufacturing process is cleaned off. For example, on the occasion of a maintenance of equipment that forms Ru using physical vapor deposition (PVD), or chemical vapor deposition (CVD), it becomes possible to inhibit ruthenium-containing gas generation during cleaning by adding the inhibitor for ruthenium-containing gas generation of the present invention to a cleaning liquid used at the time of removing Ru adhered to chambers, pipes, or the like. According to this method, the ruthenium-containing gas generation can be inhibited by the mechanism described above in connection with the description concerning the inhibitor for ruthenium-containing gas generation.

In the method for inhibiting ruthenium-containing gas generation, it is preferable to adjust the concentration of the onium salt in the inhibitor for ruthenium-containing gas generation and the addition amount of the same, such that the concentration of one or more kinds of the onium salts expressed by any of the above Formulas (2) to (5) in a mixture liquid of the inhibitor for ruthenium-containing gas generation and the liquid for treating ruthenium falls within a range of 0.0001 to 50 mass %. As for the method for inhibiting ruthenium-containing gas generation, the same pH adjuster as those described in connection with the second through fourth aspects above can be added as appropriate to the inhibitor for ruthenium-containing gas generation. The content of a pH adjuster in the inhibitor for ruthenium-containing gas generation and the addition amount of the inhibitor for ruthenium-containing gas generation can be adjusted as appropriate such that the pH of the liquid mixed with the liquid for treating ruthenium becomes, for example, from 7 to 14.

The addition amount of the inhibitor for ruthenium-containing gas generation in a liquid for treating ruthenium depends on the amount of ruthenium to be dissolved in the treatment liquid containing the inhibitor for gas generation. There is no particular restriction on the addition amount of the inhibitor for ruthenium-containing gas generation, however it is preferably from 10 to 500000 in terms of weight ratio with respect to the amount of ruthenium dissolved in the liquid for treating ruthenium as 1, more preferably from 100 to 100000, and further preferably from 1000 to 50000.

(Treatment Agent for Ruthenium-Containing Waste Fluid)

The treatment agent for a ruthenium-containing waste fluid is a liquid, which comprises an onium salt expressed by any of Formulas (2) to (5), and is added to a ruthenium-containing waste fluid for inhibiting ruthenium-containing gas generation. Therefore, a treatment liquid comprising the onium salt expressed by Formula (2), (3), (4), or (5) (the treatment liquid of the second aspect, the treatment liquid of the third aspect, and the treatment liquid of the fourth aspect) can be used as a treatment agent for a ruthenium-containing waste fluid utilizing its inhibitory effect on ruthenium-containing gas generation.

In this regard, a ruthenium-containing waste fluid means a solution containing even a small amount of Ru. In this regard, Ru is not limited to ruthenium metal, but includes any substance comprising the ruthenium element, such as Ru, $RuO_4^-$, $RuO_4^{2-}$, $RuO_4$, and $RuO_2$. For example, a liquid after the etching treatment of a semiconductor wafer containing ruthenium using an etching liquid having a composition different from that of each aspect of the present invention, and a liquid after a treatment using a treatment liquid for a semiconductor wafer of each aspect of the present invention can be exemplified. However, not limited to etching of a semiconductor wafer, another example is a ruthenium-containing liquid generated in a semiconductor manufacturing process, or by chamber cleaning, as described above in connection with the method for inhibiting ruthenium-containing gas generation.

When even a small amount of Ru is contained in a waste fluid, $RuO_2$ particles are generated via a $RuO_4$ gas, and therefore tanks and piping are contaminated therewith and deterioration of equipment is accelerated due to the oxidation effect of the particles. In addition, the $RuO_4$ gas generated from the waste fluid is highly toxic to the human body even at a low concentration. As described above, a ruthenium-containing waste fluid has various adverse effects on equipment and the human body, and it is necessary to treat it as soon as possible to inhibit $RuO_4$ gas generation.

In the treatment agent for a ruthenium-containing waste fluid of the present invention, the same conditions as those described with respect to the treatment liquid for a semiconductor wafer of each aspect regarding the kind among the onium salts expressed by any of Formulas (2) to (5) and the content thereof, another component and the content thereof, and pH, can be applied.

In addition to these conditions, the content of the onium salt expressed by any of Formulas (2) to (5) in the treatment agent for a ruthenium-containing waste fluid is, for example, from 0.0001 to 50 mass %, and more preferably from 0.001 to 35 mass %. This concentration can be adjusted such that the concentration of the onium salt in the mixed solution when mixed with a ruthenium-containing waste fluid reaches a predetermined amount, as described below. The same pH adjuster as described in the second through fourth aspects above can be added as appropriate to the treatment agent for a ruthenium-containing waste fluid. The content of the pH adjuster can be adjusted such that the pH of the mixed liquid when mixed with the ruthenium-containing waste fluid falls within the predetermined range as described below. For example, the content of a pH adjuster in a treatment agent for ruthenium-containing waste fluid is required to reach an effective amount, and specifically it is, for example, from 0.000001 to 10 mass %.

(Method for Treating Ruthenium-Containing Waste Fluid)

The method for treating a ruthenium-containing waste fluid is a method for treating a ruthenium-containing waste fluid comprising a step of adding the aforedescribed treatment agent for a ruthenium-containing waste fluid to a ruthenium-containing waste fluid described below. According to this method, a ruthenium-containing gas generated from a ruthenium-containing waste fluid can be inhibited by the mechanism described above in connection with the inhibitor for ruthenium-containing gas generation. Therefore, by this method not only the handling of a ruthenium-containing waste fluid is facilitated, but also the exhaust equipment or removal equipment can be simplified, and the costs of a treatment of a ruthenium-containing gas can be reduced. Furthermore, the danger of workers to be exposed to the highly toxic ruthenium-containing gas is reduced, and the safety is greatly improved.

In the method for treating a ruthenium-containing waste fluid, it is preferable to adjust the concentration and addition amount of the onium salt in a treatment agent for ruthenium-containing waste fluid such that the concentration of one or more of the onium salts expressed by any of Formulas (2) to (5) in a mixed liquid of a treatment agent for a ruthenium-containing waste fluid and the ruthenium-containing waste fluid falls within a range of 0.0001 to 50 mass %. In the method for treating a ruthenium-containing waste fluid, the same pH adjuster as those described above in the second through fourth aspects can be added as appropriate to the treatment agent for a ruthenium-containing waste fluid. The content of the pH adjuster in the treatment agent for a ruthenium-containing waste fluid and the addition amount of the treatment agent for a ruthenium-containing waste fluid can be adjusted appropriately such that the pH of the mixed liquid when mixed with the ruthenium-containing waste fluid falls within a range of, for example, 7 to 14.

The addition amount of a treatment agent for a ruthenium-containing waste fluid with respect to a ruthenium-containing waste fluid depends on the amount of ruthenium in the ruthenium-containing waste fluid. Although there is no particular restriction on the addition amount of a treatment agent for a ruthenium-containing waste fluid, for example, it is preferably from 10 to 500000 in terms of weight ratio with respect to the amount of ruthenium in the ruthenium-containing waste fluid as 1, more preferably from 100 to 100000, and further preferably from 1000 to 50000.

EXAMPLES

The present invention will be described below more specifically with reference to Experimental Examples, but the present invention is not limited to these Experimental Examples.

Experimental Example 1 and Reference Example 1

(pH Measurement Method)

The pH was measured with 30 mL of each treatment liquid prepared in Experimental Example 1 and Reference Example 1 using a desktop pH meter (LAQUA F-73, manufactured by HORIBA, Inc.). The pH measurement was carried out after the temperature of the treatment liquid had stabilized at 25° C.

(Method for Calculating Effective Chlorine Concentration and Hypochlorite Ion Concentration)

After preparing treatment liquids of Experimental Examples and Reference Examples, 0.5 mL of each treatment liquid, 2 g of potassium iodide (special grade chemical, produced by Wako Pure Chemical Industries, Ltd), 8 mL of a 10% acetic acid, and 10 mL of ultrapure water were charged into a 100-mL Erlenmeyer flask, and stirred until the solids dissolved to obtain a brown solution. The prepared brown solution was subjected to redox titration using a 0.02 M sodium thiosulfate solution (for volumetric analysis, produced by Wako Pure Chemical Industries, Ltd.) until the color of the solution turns from brown to very pale yellow, and then a starch solution was added to obtain a light purple solution. Next, to this solution, a 0.02M sodium thiosulfate solution was further added until the endpoint at which the solution became colorless and transparent, based on which the effective chlorine concentration was calculated. The hypochlorite ion concentration was calculated from the effective chlorine concentration obtained. For example, if the effective chlorine concentration is 1%, the hypochlorite ion concentration is 0.73%. This is common in the following Experimental Examples 1 to 5.

(Method for Calculating Tetramethylammonium Ion Concentration)

Each concentration of tetramethylammonium ions in the treatment liquids of Experimental Examples and Reference Examples was calculated from the pH, hypochlorite ion concentration, and sodium ion concentration. In this regard, the sodium ion concentration was measured by an ICP-MS (inductively coupled plasma mass spectrometer).

(Method for Calculating Etching Rate of Ruthenium)

An oxide film was formed on a silicon wafer using a batch-type thermal oxidation furnace, and thereon a 1200 Å (±10%) ruthenium film was deposited using the sputtering method. The sheet resistance was measured with a four-probe resistance measurement device (LORESTA-GP, manufactured by Mitsubishi Chemical Analytech Co., Ltd.) and converted to a film thickness.

In a fluorine resin-made container with a lid (94.0 mL PFA container, produced by AS ONE Corporation), 30 mL of a treatment liquid of each Experimental Example and Reference Example was prepared, and a sample piece with a size of 10×20 mm was immersed in the treatment liquid at 23° C. for 1 min. The etching rate was calculated by dividing the change in the film thickness between before and after the above treatment by the immersion time.

From the calculated etching rate, the required time to etch 50 Å±10 Å of ruthenium was calculated, and after treating a ruthenium film for the time required to etch 50 Å±10 Å, the ruthenium surface was observed with a field emission-type scanning electron microscope (FE-SEM; Field Emission Scanning Electron Microscope) at 100000×. In this observation, if a roughened surface was observed, it was rated as poor (C), if a slightly roughened surface was observed, it was rated as good (B), and if no surface roughening was observed, it was rated as excellent (A).

Experimental Example 1-1

(Preparation of Sample to be Etched)

A silicon wafer with a cleaned surface was prepared, and a 500 nm thermal oxidation film was formed. Ruthenium was then deposited on the thus prepared silicon wafer by the sputtering method to prepare a sample in which a 1200 Å-thick ruthenium layer was laminated on the silicon wafer.

(Production of Treatment Liquid)

<Pretreatment of Ion Exchange Resin; Preparation of Hydrogen-Form Ion Exchange Resin>

In a glass column (Bio Column CF-50TK, manufactured by AS ONE Corporation) with an inner diameter of about 45 mm, 200 mL of a sodium-form strongly acidic ion exchange resin (AMBERLITE IR-120 BNa, produced by Organo Corporation) was charged. Then, 1 L of a iN hydrochloric acid (for volumetric analysis, Wako Pure Chemical Industries, Ltd.) was fed through the ion exchange resin column to change it to the hydrogen-form, and then 1 L of ultrapure water was fed to rinse the ion exchange resin.

<Step (a)>

Further, 1 L of a 10% tetramethylammonium hydroxide solution was fed to 209 mL of the ion exchange resin that had been exchanged to the hydrogen-form, and the ions were exchanged from the hydrogen form to the tetramethylammonium form. After the ion exchange, 1 L of ultrapure water was fed to rinse the ion exchange resin.

<Step (b)>

After 69 g of sodium hypochlorite pentahydrate (special grade chemical, produced by Wako Pure Chemical Industries) was placed in a 2 L fluorine resin-made container, 931 g of ultrapure water was added to prepare a 3.11 mass % aqueous solution of sodium hypochlorite. The prepared aqueous solution of sodium hypochlorite was fed to an ion exchange resin exchanged to a tetramethylammonium form to obtain 1000 g of an aqueous solution of tetramethylammonium hypochlorite. To 999.9 g of the obtained aqueous solution of tetramethylammonium hypochlorite, 100 mg of tetradecyltrimethylammonium chloride was added to obtain a treatment liquid having the composition registered in Table 1.

<Evaluation>

Figure 3:
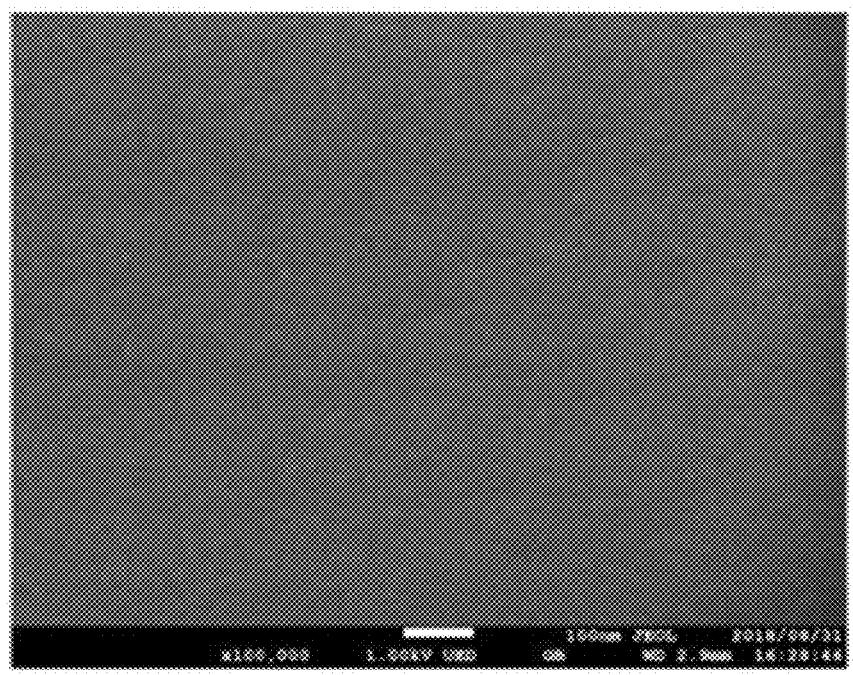
FIG. 3: A photograph of the ruthenium surface after the etching treatment shown in Example 1, observed with an electron microscope at 100,000×.

The pH, effective chlorine concentration, and hypochlorite ion concentration of the obtained treatment liquid were evaluated, and it was confirmed that the pH was 10 and the hypochlorite ion concentration was 2.15 mass %. The etching rate was also evaluated using the "Method for calculating etching rate of ruthenium" described above. From the calculated etching rate, the time required to etch 50 Å±10 Å of ruthenium was calculated, and a ruthenium film treated for the time required to etch 50 Å±10 Å was prepared, and used as the ruthenium film for surface observation. The ruthenium surface was observed using an electron microscope of 100000× power. The results of the observation are shown in FIG. 3.

Experimental Example 1-2

An aqueous solution of tetramethylammonium hypochlorite was obtained identically with Experimental Example 1-1, except that the amount of the ion exchange resin in the step (a) was set at 564 mL, the feed amount of the 10% tetramethylammonium hydroxide solution was set at 2 L, and the concentration of the aqueous solution of sodium hypochlorite in the step (b) was set at 8.39 mass %. In addition, as the pH adjustment step (c), a 25% tetramethylammonium hydroxide (TMAH) solution was added to the aqueous solution of tetramethylammonium hypochlorite until the pH became 11. To 999 g of the obtained aqueous solution of tetramethylammonium hypochlorite, 1 g of decyltrimethylammonium chloride was added to obtain a treatment liquid having the composition registered in Table 1. The evaluation results are shown in Table 2.

Experimental Example 1-3

An aqueous solution of tetramethylammonium hypochlorite was obtained identically with Example 1, except that the amount of the ion exchange resin in the step (a) was set at 705 mL, the feed amount of the 10% tetramethylammonium hydroxide solution was set at 2 L, and the concentration of the aqueous solution of sodium hypochlorite in the step (b) was set at 10.49 mass %. In addition, as the pH adjustment step (c), a 25% tetramethylammonium hydroxide (TMAH) solution was added to the aqueous solution of tetramethylammonium hypochlorite until the pH became 12. To 999.5 g of the obtained aqueous solution of tetramethylammonium hypochlorite, 500 mg of lauryltrimethylammonium chloride was added to obtain a treatment liquid having the composition registered in Table 1. The evaluation results are shown in Table 2.

Experimental Example 1-4

After obtaining an aqueous solution of tetramethylammonium hypochlorite by performing the same operation as in Experimental Example 1-2, 500 mg of octadecyltrimethylammonium chloride was added to 999.5 g of the aqueous solution of tetramethylammonium hypochlorite to obtain a treatment liquid having the composition registered in Table 1. The evaluation results are shown in Table 2.

Experimental Example 1-5

An aqueous solution of tetramethylammonium hypochlorite was obtained identically with Experimental Example 1-1, except that the amount of the ion exchange resin in the step (a) was set at 282 mL, and the concentration of the aqueous solution of sodium hypochlorite in the step (b) was set at 4.20 mass %. In addition, as the pH adjustment step (c), a 25% tetramethylammonium hydroxide (TMAH) solution was added to the aqueous solution of tetramethylammonium hypochlorite until the pH became 11. To 990 g of the obtained aqueous solution of tetramethylammonium hypochlorite, 10 g of n-octyltrimethylammonium chloride was added to obtain a treatment liquid having the composition registered in Table 1. The evaluation results are shown in Table 2.

Experimental Example 1-6

After obtaining an aqueous solution of tetramethylammonium hypochlorite by performing the same operation as in Experimental Example 1-1, as the pH adjustment step (c), the aqueous solution of tetramethylammonium hypochlorite was fed to a glass column packed with 50 mL of a sodium form strongly acidic ion exchange resin (AMBERLITE IR-120 BNa, produced by Organo Corporation) converted to a hydrogen form. To 999.9 g of the obtained aqueous solution of tetramethylammonium hypochlorite, 100 mg of tetradecyltrimethylammonium chloride was added to obtain a treatment liquid having the composition registered in Table 1. The evaluation results are shown in Table 2.

Experimental Example 1-7

After obtaining an aqueous solution of tetramethylammonium hypochlorite by performing the same operation as in Experimental Example 1-4, to 999.9 g of the aqueous solution of tetramethylammonium hypochlorite, 100 mg of hexadecyltrimethylammonium chloride was added to obtain a treatment liquid having the composition registered in Table 1. The evaluation results are shown in Table 2.

Experimental Example 1-8

Sodium hypochlorite pentahydrate (special grade chemical, produced by Wako Pure Chemical Industries, Ltd.) was dissolved in water such that the hypochlorite ion became 2.15 mass %. To 999 g of the obtained aqueous solution of sodium hypochlorite, 1 g of tetradecyltrimethylammonium chloride was added to obtain a treatment liquid having the composition registered in Table 1. The evaluation results are shown in Table 2.

Experimental Example 1-9

Compared to Experimental Example 1-1, the amount of ion exchange resin in the step (a) was set at 282 mL, and the concentration of the aqueous solution of sodium hypochlorite in the step (b) was set at 4.20 mass %. To 999.5 g of the obtained aqueous solution of tetramethylammonium hypochlorite, 500 mg of didecyldimethylammonium chloride was added to obtain a treatment liquid having the composition registered in Table 1. The evaluation results are shown in Table 2.

Experimental Example 1-10

After obtaining an aqueous solution of tetramethylammonium hypochlorite by performing the same operation as in Experimental Example 1-9, to 999.9 g of the obtained aqueous solution of tetramethylammonium hypochlorite, 100 mg of didodecyldimethylammonium chloride was added to obtain a treatment liquid having the composition registered in Table 1. The evaluation results are shown in Table 2.

Reference Example 1-1

A treatment liquid was prepared in the same manner as in Experimental Example 1-1, except that the alkylammonium salt expressed by Formula (1) was not added, and the same evaluation as in Experimental Example 1-1 was performed.

The compositions of each treatment liquid prepared in Experimental Example 1 and Reference Example 1 as above are shown in Table 1, and the results obtained are shown in Table 2.

TABLE 2

| | Ru etching (23° C.) Å · min$^{-1}$ | Surface roughness (SEM) |
|---|---|---|
| Experimental Example 1-1 | 50 | A |
| Experimental Example 1-2 | 75 | A |
| Experimental Example 1-3 | 30 | A |
| Experimental Example 1-4 | 80 | B |
| Experimental Example 1-5 | 45 | B |
| Experimental Example 1-6 | 420 | A |
| Experimental Example 1-7 | 90 | A |
| Experimental Example 1-8 | 95 | A |
| Experimental Example 1-9 | 65 | A |
| Experimental Example 1-10 | 55 | A |
| Reference Example 1-1 | 110 | C |

As shown in Table 2, in Experimental Examples 1-1 to 1-10, where the treatment liquid of the present invention is applied, the flatness of the ruthenium surface after etching is maintained, therefore the same can be suitably used as a treatment liquid for a semiconductor wafer. FIG. 3 shows an electron microscopic image of 100000× of the ruthenium after the etching treatment obtained in Experimental Example 1-1. It is to be known that formation of $RuO_2$ (particles) on the wafer surface was inhibited and a flat ruthenium surface was obtained.

Since no surfactant is added in Reference Example 1-1, it can be known that the flatness after etching was degraded compared to Experimental Examples 1-1 to 1-10.

Experimental Example 1-11

After obtaining an aqueous solution of tetramethylammonium hypochlorite by performing the same operation as in Experimental Example 1-1, to 999 g of the obtained aqueous solution of tetramethylammonium hypochlorite, 1 g of tetraheptylammonium chloride was added to obtain a treatment liquid having the composition registered in Table 3.

TABLE 1

| | ClO− (wt %) | TMA+ (wt %) | Surfactant Kind | Addition amount (ppm) | pH |
|---|---|---|---|---|---|
| Experimental Example 1-1 | 2.15 | 3.09 | Tetradecyltrimethylammonium chloride | 100 | 10 |
| Experimental Example 1-2 | 5.79 | 8.33 | Decyltrimethylammonium chloride | 1000 | 11 |
| Experimental Example 1-3 | 7.25 | 10.42 | Lauryltrimethylammonium chloride | 500 | 12 |
| Experimental Example 1-4 | 5.8 | 8.34 | Octadecyltrimethylammonium chloride | 500 | 11 |
| Experimental Example 1-5 | 2.87 | 4.14 | n-Octyltrimethylammonium chloride | 10000 | 11 |
| Experimental Example 1-6 | 2.15 | 2.35 | Tetradecyltrimethylammonium chloride | 100 | 8 |
| Experimental Example 1-7 | 5.8 | 8.34 | Hexadecyltrimethylammonium chloride | 100 | 11 |
| Experimental Example 1-8 | 2.9 | — | Tetradecyltrimethylammonium chloride | 1000 | 11 |
| Experimental Example 1-9 | 2.9 | 4.17 | Didecyldimethylammonium chloride | 500 | 10 |
| Experimental Example 1-10 | 2.9 | 4.17 | Didodecyldimethylammonium chloride | 100 | 10 |
| Reference Example 1-1 | 2.15 | 3.09 | — | — | 10 |

Reference Examples 1-2 to 1-3

The treatment liquids registered in Table 3 were obtained according to the procedure of Experimental Example 1-1.

TABLE 3

| | ClO- (wt %) | TMA+ (wt %) | Surfactant Kind | Surfactant Addition amount (ppm) | pH | Ru etching (23° C.) Å · min − 1 | Surface roughness (SEM) |
|---|---|---|---|---|---|---|---|
| Experimental Example 1-11 | 2.15 | 3.09 | Tetraheptyl-ammonium chloride | 100 | 10 | 60 | B |
| Reference Example 1-2 | 2.15 | 3.09 | — | — | 10 | 110 | C |
| Reference Example 1-3 | 2.9 | 4.17 | Triethylmethyl-ammonium chloride | 1000 | 10 | 140 | C |
| Reference Example 1-4 | 2.15 | 3.09 | Butyltrimethyl-ammonium chloride | 100 | 11 | 55 | C |

As obvious from the results shown in Table 3, desirable surface roughness could not be obtained when an alkylammonium salt in which structure an alkyl group with a carbon number of 7 or more was not present was used as a surfactant.

Experimental Example 2 and Reference Example 2

(Production of Treatment Liquid)
Treatment liquids were prepared as follows to meet the compositions set forth in Tables 4 and 5. In a 100 mL fluorine resin-made container, sodium hypochlorite (produced by Wako Pure Chemical Industries, Ltd.), or orthoperiodic acid (produced by Fujifilm Wako Pure Chemical Corporation), a quaternary onium salt or a tertiary onium salt, an organic solvent, and ultrapure water were charged, and the pH was adjusted to the value set forth in the table using a 15 wt % HCl aqueous solution, or a 1.0 mol/L NaOH aqueous solution to prepare 60 mL of a treatment liquid. (Note that an organic solvent was not added in Experimental Examples 2-1 to 2-12, and Reference Examples 2-1 to 2-5 shown in Table 4.) The effective chlorine concentration of each obtained treatment liquid was confirmed to be 2.0 wt %, and the treatment liquids listed in Tables 4 and 5 were obtained.

(pH Measurement Method)
The pH was measured with 10 mL of the treatment liquid prepared in each Experimental Example and Reference Example using a desktop pH meter (LAQUA F-73, manufactured by HORIBA, Inc.). The pH measurement was carried out after the temperature of the treatment liquid had stabilized at 25° C.

(Quantitative Analysis of $RuO_4$ Gas)
The amount of a generated $RuO_4$ gas was measured using ICP-OES. In an airtight container 5 mL of a treatment liquid was placed, and one piece of 10×20 mm Si wafer, on which ruthenium was deposited to a film thickness of 1200 Å, was immersed therein at 25° C. or 50° C. until all the ruthenium was dissolved. Then, air was fed into the airtight container such that the gas phase in the airtight container was bubbled into an absorbing liquid (1 mol/L NaOH) in a separate container for trapping therein the $RuO_4$ gas generated during immersion. The amount of ruthenium in the absorbing liquid was measured by ICP-OES to determine the amount of Ru in the generated $RuO_4$ gas. Whether all the ruthenium on the Si wafer immersed in the treatment liquid was dissolved was confirmed by measuring the respective sheet resistances before and after the immersion with a four-probe resistance measurement device (LORESTA-GP, manufactured by Mitsubishi Chemical Analytech Co., Ltd.), and by converting them into a film thickness.

(Confirmation of Precipitates)
In an airtight container, 10 mL of a treatment liquid was placed and five pieces of 10×20 mm Si wafer, on which ruthenium was deposited to a film thickness of 1200 Å, were immersed therein at 25° C. for 10 min. Thereafter, it was visually examined whether precipitates were formed in the treatment liquid.

Experimental Examples 2-1 to 2-17 and Reference Examples 2-1 to 2-5

The composition of each treatment liquid and each evaluation result are shown in Tables 4 and 5. The amount of Ru in Table 4 is the weight of Ru contained in the $RuO_4$ gas absorbing liquid divided by the area of the wafer with Ru.

TABLE 4

| | Oxidizing agent | Quaternary or Tertiary onium salt | pH | Temperature [° C.] | Ru content in $RuO_4$ gas [μg/cm²] |
|---|---|---|---|---|---|
| Experimental Example 2-1 | 2.0 mass % NaClO aqueous solution | Tetrapropylammonium chloride (40.2 mass %) | 7.0 | 25 | 2.0 |
| Experimental Example 2-2 | 2.0 mass % NaClO aqueous solution | Tetrapropylammonium hydroxide (21.4 mass %) | 9.5 | 25 | 2.3 |
| Experimental Example 2-3 | 2.0 mass % NaClO aqueous solution | Tetrapropylammonium hydroxide (8.8 mass %) | 12.0 | 25 | 2.7 |

TABLE 4-continued

|  | Oxidizing agent | Quaternary or Tertiary onium salt | pH | Temperature [° C.] | Ru content in RuO$_4$ gas [μg/cm$^2$] |
|---|---|---|---|---|---|
| Experimental Example 2-4 | 2.0 mass % NaClO aqueous solution | Didodecyldimethylammonium chloride (0.5 mass %) | 12.0 | 25 | 1.5 |
| Experimental Example 2-5 | 2.0 mass % NaClO aqueous solution | Triphenylsulfonium chloride (1.7 mass %) | 12.0 | 25 | 1.4 |
| Experimental Example 2-6 | 2.0 mass % NaClO aqueous solution | Butyltriphenylphosphonium chloride (0.1 mass %) | 12.0 | 25 | 1.2 |
| Experimental Example 2-7 | 2.0 mass % NaClO aqueous solution | Tetrabutylammonium hydroxide (33 mass %) | 12.0 | 25 | 1.8 |
| Experimental Example 2-8 | 2.0 mass % NaClO aqueous solution | Tetradecyltrimethylammonium chloride (8 mass %) | 12.0 | 25 | 1.4 |
| Experimental Example 2-9 | 2.0 mass % NaClO aqueous solution | Hexadecyltrimethylammonium chloride (7 mass %) | 12.0 | 25 | 1.5 |
| Experimental Example 2-10 | 2.0 mass % NaClO aqueous solution | n-Decyltrimethylammonium chloride (8 mass %) | 12.0 | 25 | 2.1 |
| Experimental Example 2-11 | 2.0 mass % NaClO aqueous solution | Tetapropylammonium chloride (40.2 mass %) | 12.0 | 50 | 1.6 |
| Experimental Example 2-12 | 1.0 mass % H$_5$IO$_6$ aqueous solution | Tetrapropylammonium chloride (40.2 mass %) | 7.0 | 25 | 1.3 |
| Reference Example 2-1 | 2.0 mass % NaClO aqueous solution | None | 7.0 | 25 | 58 |
| Reference Example 2-2 | 2.0 mass % NaClO aqueous solution | None | 9.5 | 25 | 40 |
| Reference Example 2-3 | 2.0 mass % NaClO aqueous solution | None | 12.0 | 25 | 18.9 |
| Reference Example 2-4 | 2.0 mass % NaClO aqueous solution | None | 12.0 | 50 | 45 |
| Reference Example 2-5 | 1.0 mass % H$_5$IO$_6$ aqueous solution | None | 7.0 | 25 | 50 |

Comparing respectively Experimental Example 2-1 with Reference Example 2-1 (pH 7.0), Experimental Example 2-2 with Reference Example 2-2 (pH 9.5), and Experimental Example 2-3 with Reference Example 2-3 (pH 12.0), it can be known that the amount of generated RuO$_4$ gas can be reduced by addition of a quaternary onium salt at any pH.

In Experimental Examples 2-4 to 2-10, different kinds of onium salts were used compared to Experimental Example 2-1 to 2-3. In a case where onium salts different in terms of carbon number, A$^+$, and X$^-$ were used as the quaternary onium salt or tertiary onium salt expressed by Formula (2) or Formula (3) above, when the carbon number of the alkyl chain of the onium salt was greater than 10, foaming of the treatment liquid was recognized, however in any of Experimental Examples 2-4 to 2-10 the inhibitory effect on a RuO$_4$ gas was obtained. For example, in the case of carbon number, the concentration of the quaternary onium salt in the treatment liquid was 8.8 wt % in Experimental Example 2-3, while in Experimental Example 2-4 it was 0.5 wt %. Namely, in Experimental Example 2-4 where the carbon number of the quaternary onium salt was larger, the inhibitory effect on the gas was obtained by addition of a smaller amount of the quaternary onium salt.

Comparing Reference Example 2-4 with Experimental Example 2-11, it can be seen that RuO$_4$ gas generation could be inhibited even at 50° C. by addition of the onium salt.

Comparing Reference Example 2-5 with Experimental Example 2-12, it can be seen that RuO$_4$ gas generation could be inhibited by addition of the onium salt even when 1 mass % orthoperiodic acid was used as an oxidizing agent.

Reference Example 2-6

The treatment liquid of Reference Example 2-6 was prepared in the same manner as in Reference Example 2-2 except that in contrast to Reference Example 2-2 shown in Table 4, 1 wt % of 2,2,6,6-tetramethylpiperidine 1-oxyl (TEMPO) was added. Using this treatment liquid, a quantitative analysis of RuO$_4$ gas was performed to find that the amount of Ru in the generated RuO$_4$ gas was 40 μg/cm$^2$. Although Patent Document 7 indicates that TEMPO has an inhibitory effect on a RuO$_4$ gas, the inhibitory effect on a RuO$_4$ gas could not be confirmed under alkaline conditions.

TABLE 5

|  | Oxidizing agent | Quaternary or Tertiary onium salt | Organic solvent (mass %) | Relative dielectric constant of organic solvent | Precipitate | Gas inhibitory effect |
|---|---|---|---|---|---|---|
| Experimental Example 2-13 | 2 mass % NaClO aqueous solution | Tetrapropylammonium hydroxide (8.8 mass %) | Acetonitrile (0.8 mass %) | 37 | No | Yes |
| Experimental Example 2-14 | 2 mass % NaClO aqueous solution | Tetrapropylammonium hydroxide (8.8 mass %) | Acetonitrile (8 mass %) | 37 | No | Yes |
| Experimental Example 2-15 | 2 mass % NaClO aqueous solution | Tetrapropylammonium hydroxide (8.8 mass %) | Acetonitrile (16 mass %) | 37 | No | Yes |

TABLE 5-continued

| | Oxidizing agent | Quaternary or Tertiary onium salt | Organic solvent (mass %) | Relative dielectric constant of organic solvent | Precipitate | Gas inhibitory effect |
|---|---|---|---|---|---|---|
| Experimental Example 2-16 | 2 mass % NaClO aqueous solution | Tetrapropylammonium hydroxide (8.8 mass %) | Sulfolane (2.5 mass %) | 43 | No | Yes |
| Experimental Example 2-17 | 2 mass % NaClO aqueous solution | Tetrapropylammonium hydroxide (8.8 mass %) | None | — | Yes | Yes |

In Experimental Example 2-17, $RuO_4$ gas generation was inhibited, but precipitates were generated that cause particle formation in the treatment liquid after the immersion treatment of Si wafers with Ru. On the other hand, formation of precipitates could be inhibited in Experimental Examples 2-13 to 2-16, in which acetonitrile or sulfolane, which have a lower relative dielectric constant than water, were added.

Treatment liquids were prepared as follows so as to meet the compositions set forth in Tables 6 to 9. Sodium hypochlorite (produced by Wako Pure Chemical Industries, Ltd.), a quaternary onium salt or a tertiary onium salt, and ultrapure water were charged into a 100 mL fluorine resin-made container, and then the pH was adjusted to the value set forth in the table using a 15 wt % HCl aqueous solution to prepare 60 mL of a treatment liquid. Thus the treatment liquids listed in Tables 6 to 9 were yielded, while it was confirmed that the yielded treatment liquids had an effective chlorine concentration of 2.0 wt %.

TABLE 6

| | Oxidizing agent | Onium salt | pH | Ru content in $RuO_4$ gas [$\mu g/cm^2$] |
|---|---|---|---|---|
| Reference Example 2-7 | 2.0 mass % NaClO aqueous solution | — | 12 | 18.9 |
| Experimental Example 2-18 | 2.0 mass % NaClO aqueous solution | Trimethylphenylammonium chloride (1.7 mass %) | 12 | 2.8 |
| Experimental Example 2-19 | 2.0 mass % NaClO aqueous solution | Trimethylphenylammonium chloride (7.1 mass %) | 12 | 1.2 |

TABLE 7

| | Oxidizing agent | Onium salt | pH | Ru content in $RuO_4$ gas [$\mu g/cm^2$] |
|---|---|---|---|---|
| Reference Example 2-8 | 2.0 mass % NaClO aqueous solution | — | 12 | 18.9 |
| Experimental Example 2-20 | 2.0 mass % NaClO aqueous solution | Tetraethylammonium chloride (10 mass %) | 12 | 13.8 |
| Experimental Example 2-21 | 2.0 mass % NaClO aqueous solution | Tetraethylammonium chloride (20 mass %) | 12 | 10.0 |
| Experimental Example 2-22 | 2.0 mass % NaClO aqueous solution | Tetraethylammonium chloride (40 mass %) | 12 | 5.0 |

TABLE 8

| | Oxidizing agent | Onium salt | pH | Ru content in $RuO_4$ gas [$\mu g/cm^2$] |
|---|---|---|---|---|
| Reference Example 2-9 | 2.0 mass % NaClO aqueous solution | — | 12 | 18.9 |
| Experimental Example 2-23 | 2.0 mass % NaClO aqueous solution | Neopentyltrimethylammonium chloride (1.1 mass %) | 12 | 13 |

As obvious from the results described in Tables 6 to 8, the inhibitory effect on a $RuO_4$ gas was obtained by using a treatment liquid comprising a quaternary onium salt expressed by Formula (2). From the results in Tables 6 and 7, it was found that the inhibitory effect became higher as the concentration of the same in the treatment liquid increased.

TABLE 9

| | Oxidizing agent | Onium salt | pH | Ru content in $RuO_4$ gas [$\mu g/cm^2$] |
|---|---|---|---|---|
| Reference Example 2-10 | 2.0 mass % NaClO aqueous solution | — | 7 | 58.0 |
| Experimental Example 2-24 | 2.0 mass % NaClO aqueous solution | n-Octyltrimethylammonium chloride (2.1 mass %) | 7 | 35.0 |
| Experimental Example 2-25 | 2.0 mass % NaClO aqueous solution | n-Octyltrimethylammonium chloride (16.6 mass %) | 7 | 3.0 |
| Reference Example 2-11 | 2.0 mass % NaClO aqueous solution | — | 9 | 42.0 |
| Experimental Example 2-26 | 2.0 mass % NaClO aqueous solution | n-Octyltrimethylammonium chloride (2.1 mass %) | 9 | 16.0 |

TABLE 9-continued

| | Oxidizing agent | Onium salt | pH | Ru content in RuO$_4$ gas [μg/cm$^2$] |
|---|---|---|---|---|
| Experimental Example 2-27 | 2.0 mass % NaClO aqueous solution | n-Octyltrimethylammonium chloride (16.6 mass %) | 9 | 1.0 |
| Reference Example 2-12 | 2.0 mass % NaClO aqueous solution | — | 10 | 33.0 |
| Experimental Example 2-28 | 2.0 mass % NaClO aqueous solution | n-Octyltrimethylammonium chloride (2.1 mass %) | 10 | 12.0 |
| Experimental Example 2-29 | 2.0 mass % NaClO aqueous solution | n-Octyltrimethylammonium chloride (12.5 mass %) | 10 | 1.1 |
| Experimental Example 2-30 | 2.0 mass % NaClO aqueous solution | n-Octyltrimethylammonium chloride (16.6 mass %) | 10 | 0 |
| Reference Example 2-13 | 2.0 mass % NaClO aqueous solution | — | 12 | 18.9 |
| Experimental Example 2-31 | 2.0 mass % NaClO aqueous solution | n-Octyltrimethylammonium chloride (2.1 mass %) | 12 | 1.5 |
| Experimental Example 2-32 | 2.0 mass % NaClO aqueous solution | n-Octyltrimethylammonium chloride (12.5 mass %) | 12 | 0 |
| Experimental Example 2-33 | 2.0 mass % NaClO aqueous solution | n-Octyltrimethylammonium chloride (16.6 mass %) | 12 | 0 |
| Experimental Example 2-34 | 2.0 mass % NaClO aqueous solution | n-Octyltrimethylammonium chloride (2.1 mass %) | 13 | 0.2 |
| Experimental Example 2-35 | 2.0 mass % NaClO aqueous solution | n-Octyltrimethylammonium chloride (16.6 mass %) | 13 | 0 |

From the results shown in Table 9, it was found that using a treatment liquid comprising a quaternary onium salt expressed by Formula (2), the inhibitory effect on a RuO$_4$ gas could be obtained even when the pHs of the treatment liquids were different. It was also found that the inhibitory effect became higher as the concentration of the quaternary onium salt in the treatment liquid increased.

As Reference Examples, treatment liquids comprising an onium salt, which did not satisfy the provisions of Formulas (2) and (3), were prepared to meet a composition set forth in the following Table 10. The preparation method was the same as the above Experimental Examples and Reference Examples.

As obvious from the results in Table 10, a sufficient inhibitory effect on gas generation was not obtained when the treatment liquid comprised an onium salt, which did not satisfy the provisions of Formulas (2) and (3).

TABLE 10

| | Oxidizing agent | Onium salt | ph | Ru content in RuO$_4$ gas [μg/cm$^2$] |
|---|---|---|---|---|
| Reference Example 2-14 | 2.0 mass % NaClO aqueous solution | — | 12 | 18.9 |
| Reference Example 2-15 | 2.0 mass % NaClO aqueous solution | Tetramethylammonium chloride (10 mass %) | 12 | 17.4 |
| Reference Example 2-16 | 2.0 mass % NaClO aqueous solution | Tetramethylammonium chloride (20 mass %) | 12 | 16.3 |
| Reference Example 2-17 | 2.0 mass % NaClO aqueous solution | Tetramethylammonium chloride (40 mass %) | 12 | 15.2 |

Experimental Example 3 and Reference Example 3

(Production of Treatment Liquid)

Treatment liquids were prepared as follows so as to meet a composition set forth in Table 11. Sodium hypochlorite (produced by Wako Pure Chemical Industries, Ltd.), an onium salt, and ultrapure water were charged into a 100 mL fluorine resin-made container, and then the pH was adjusted to pH 12.0 using a 15 wt % HCl aqueous solution to prepare 60 mL of a treatment liquid. Thus the treatment liquids listed in Table 11 were yielded, while it was confirmed that the yielded treatment liquids had an effective chlorine concentration of 2.0 wt %.

(pH Measurement Method)

The pH was measured with 10 mL of the treatment liquid prepared in each Experimental Example and Reference Example using a desktop pH meter (LAQUA F-73, manufactured by HORIBA, Inc.). The pH measurement was carried out after the temperature of the treatment liquid had stabilized at 25° C.

(Quantitative Analysis of RuO$_4$ Gas)

The amount of a generated RuO$_4$ gas was measured using ICP-OES. In an airtight container 5 mL of a treatment liquid was placed, and one piece of 10×20 mm Si wafer, on which ruthenium was deposited to a film thickness of 1200 Å, was immersed therein at 25° C. until all the ruthenium was dissolved. Then, air was fed into the airtight container such that the gas phase in the airtight container was bubbled into an absorbing liquid (1 mol/LNaOH) in a separate container for trapping therein the RuO$_4$ gas generated during immersion. The amount of ruthenium in the absorbing liquid was measured by ICP-OES to determine the amount of Ru in the generated RuO$_4$ gas. Whether all the ruthenium on the Si wafer immersed in the treatment liquid was dissolved was confirmed by measuring the respective sheet resistances before and after the immersion with a four-probe resistance measurement device (LORESTA-GP, manufactured by Mitsubishi Chemical Analytech Co., Ltd.), and by reducing them to a film thickness.

Experimental Examples 3-1 to 3-4 and Reference Example 3-1

The composition of each treatment liquid and each evaluation result are shown in Table 11. The amount of Ru in Table 11 is the weight of Ru contained in the $RuO_4$ gas absorbing liquid divided by the area of the wafer with Ru.

TABLE 11

| | Oxidizing agent | Onium salt | pH | Ru content in $RuO_4$ gas [μg/cm$^2$] |
|---|---|---|---|---|
| Experimental Example 3-1 | 2.0 mass % NaClO aqueous solution | 1-Butyl-1-methylpyrrolidinium chloride (0.36 mass %) | 12 | 6 |
| Experimental Example 3-2 | 2.0 mass % NaClO aqueous solution | 1-Butyl-2,3-dimethylimidazolium chloride (1.8 mass %) | 12 | 5 |
| Experimental Example 3-3 | 2.0 mass % NaClO aqueous solution | 1-Butyl-2,3-dimethylimidazolium chloride (7.1 mass %) | 12 | 1.4 |
| Experimental Example 3-4 | 2.0 mass % NaClO aqueous solution | 1,1-Dimethylpiperidinium chloride (1.5 mass %) | 12 | 6.2 |
| Reference Example 3-1 | 2.0 mass % NaClO aqueous solution | None | 12 | 18.9 |

Comparing Experimental Examples 3-1 to 3-4 with Reference Example 3-1, it can be known that the amount of a generated $RuO_4$ gas could be reduced by addition of an onium salt Treatment liquids were prepared by changing the kinds of onium salts to meet a composition set forth in the following Table 12 or Table 13 according to the same procedure as Experimental Example 3-1, etc.

TABLE 12

| | Oxidizing agent | Onium salt | pH | Ru content in $RuO_4$ gas [μg/cm$^2$] |
|---|---|---|---|---|
| Reference Example 3-2 | 2.0 mass % NaClO aqueous solution | — | 12 | 18.9 |
| Experimental Example 3-5 | 2.0 mass % NaClO aqueous solution | 5-Azoniaspiro[4.4]nonane chloride (1.7 mass %) | 12 | 6.5 |
| Experimental Example 3-6 | 2.0 mass % NaClO aqueous solution | 5-Azoniaspiro[4.4]nonane chloride (6.5 mass %) | 12 | 2.4 |

TABLE 13

| | Oxidizing agent | Onium salt | pH | Ru content in $RuO_4$ gas [μg/cm$^2$] |
|---|---|---|---|---|
| Reference Example 3-3 | 2.0 mass % NaClO aqueous solution | — | 12 | 18.9 |
| Experimental Example 3-7 | 2.0 mass % NaClO aqueous solution | 6-Azoniaspiro[5.5]undecane chloride (1.2 mass %) | 12 | 13 |

From the results shown in Tables 12 and 13, it was found that an adequate inhibitory effect on ruthenium-containing gas generation can be obtained by using a treatment liquid comprising an onium salt having a structure expressed by Formula (4) even if it is an onium salt having a structure different from the onium salts used in Experimental Example 3-1 to Experimental Example 3-4.

Experimental Example 4 and Reference Example 4

Treatment liquids were prepared to meet a composition set forth in Table 14 according to the procedure described in (Production of treatment liquid) for Experimental Example 3 and Reference Example 3. The pH measurement method for a treatment liquid and the quantitative analysis of $RuO_4$ gas were conducted according to the (pH measurement method) and (Quantitative analysis of $RuO_4$ gas) described with respect to Experimental Example 3 and Reference Example 3.

Experimental Examples 4-1 to 4-3 and Reference Example 4-1

The composition of each treatment liquid and each evaluation result are shown in Table 14. The amount of Ru in Table 14 is the weight of Ru contained in the $RuO_4$ gas absorbing liquid divided by the area of the wafer with Ru.

TABLE 14

| | Oxidizing agent | Onium salt | pH | Ru content in $RuO_4$ gas [μg/cm$^2$] |
|---|---|---|---|---|
| Reference Example 4-1 | 2.0 mass % NaClO aqueous solution | — | 12 | 18.9 |
| Experimental Example 4-1 | 2.0 mass % NaClO aqueous solution | Hexamethonium chloride (3.1 mass %) | 12 | 3.9 |
| Experimental Example 4-2 | 2.0 mass % NaClO aqueous solution | Hexamethonium chloride (12.4 mass %) | 12 | 1.2 |
| Experimental Example 4-3 | 2.0 mass % NaClO aqueous solution | Hexamethonium chloride (24.7 mass %) | 12 | 0.5 |

From the results shown in Table 14, it was found that generation of a ruthenium-containing gas can be sufficiently inhibited when the treatment liquid comprising an onium salt expressed by Formula (5) is used.

Experimental Example 5 and Reference Example 5

Experimental Examples 5-1 to 5-11

(Preparation of Mixed Liquid of Treatment Agent for Ruthenium-Containing Waste Fluid and Ruthenium-Containing Waste Fluid)

A treatment liquid for etching ruthenium with an effective chlorine concentration of 2.0 wt % was prepared by charging sodium hypochlorite (produced by Wako Pure Chemical Industries, Ltd.) and ultrapure water into a fluorine resin-made container, and then adjusting the pH to the value set forth in Table 15 using a 15 wt % HCl aqueous solution or a 4 wt % NaOH aqueous solution. A 300 mm Si wafer on which a 1360 Å-thick ruthenium film was deposited was immersed into 1 L of the obtained treatment liquid at 25° C. for 10 min, and thereafter the liquid was recovered in a waste fluid tank.

Then a treatment agent for a ruthenium-containing waste fluid with an effective chlorine concentration of 2.0 wt % was prepared by charging sodium hypochlorite (produced by Wako Pure Chemical Industries, Ltd.), an onium salt, and ultrapure water into a fluorine resin-made container, and then adjusting the pH to the value set forth in Table 15 using a 15 wt % HCl aqueous solution or a 4 wt % NaOH aqueous solution. By adding 1 L of the obtained treatment agent for a ruthenium-containing waste fluid to the waste fluid tank to be mixed at 25° C., a mixed liquid of the treatment agent for a ruthenium-containing waste fluid and the ruthenium-containing waste fluid (hereinafter also referred to simply as the "mixed liquid") containing $6.0 \times 10^{-4}$ mol/L of ruthenium as described in Table 15 was obtained.

(Quantitative Analysis of $RuO_4$ Gas)

The amount of a generated $RuO_4$ gas was measured using ICP-OES. In an airtight container 5 mL of the mixed liquid was placed. Air was fed into the airtight container for 15 min such that the gas phase in the airtight container was bubbled into an absorbing liquid (1 mol/L NaOH) in a separate container for trapping therein the $RuO_4$ gas generated from the mixed liquid. The amount of ruthenium in the absorbing liquid was measured by ICP-OES to determine the amount of Ru in the generated $RuO_4$ gas. Whether all the ruthenium on the treated Si wafer was dissolved was confirmed by measuring the respective sheet resistances before and after the treatment with a four-probe resistance measurement device (LORESTA-GP, manufactured by Mitsubishi Chemical Analytech Co., Ltd.), and by reducing them to a film thickness.

Experimental Example 5-12

A mixed liquid of the treatment agent for a ruthenium-containing waste fluid described in Table 15 and a ruthenium-containing waste fluid was obtained by the same method as in Experimental Example 5-1. However, the preparation was conducted such that the effective chlorine concentration of the treatment liquid for etching Ru became 4.0 wt %, and the same of the treatment agent for a ruthenium-containing waste fluid was 0% (oxidizing agent not included). A quantitative analysis of a $RuO_4$ gas was performed according to the same procedure as in Experimental Example 5-1.

Experimental Examples 5-13 to 5-15

A treatment liquid for etching Ru with an effective chlorine concentration of 4.0 wt % was obtained by the same method as in Experimental Example 5-1. 1 L of the obtained treatment liquid was poured over the surface of a 300 mm Si wafer deposited with a 2720 Å-thick ruthenium film over 10 min at 25° C., followed by rinsing with 1 L of ultrapure water, and the liquids were collected in a waste fluid tank. Next, 2 L of a treatment agent for a ruthenium-containing waste fluid with an effective chlorine concentration of 2.0 wt % obtained by the same method as in Experimental Example 5-1 was added to the waste fluid tank and mixed to obtain a mixed liquid of the treatment agent for a ruthenium-containing waste fluid described in Table 15, and the ruthenium-containing waste fluid, containing $6.0 \times 10^{-4}$ mol/L of Ru. A quantitative analysis of a $RuO_4$ gas was performed according to the same procedure as in Experimental Example 5-1.

Reference Examples 5-1 to 5-4

A treatment liquid for etching ruthenium with an effective chlorine concentration of 2.0 wt % was prepared by charging sodium hypochlorite (produced by Wako Pure Chemical Industries, Ltd.) and ultrapure water into a fluorine resin-made container, and then adjusting the pH to the value set forth in Table 16 using a 15 wt % HCl aqueous solution or a 4 wt % NaOH aqueous solution. A 300 mm Si wafer on which a 680 Å-thick ruthenium film was deposited was immersed into 1 L of the obtained treatment liquid at 25° C. for 10 min, and thereafter the liquid was recovered into a waste fluid tank to yield a ruthenium-containing waste fluid described in Table 16 containing $6.0 \times 10^{-4}$ mol/L of Ru. A quantitative analysis of a $RuO_4$ gas was performed according to the same procedure as in Experimental Example 5-1.

Reference Example 5-5

A treatment liquid for etching ruthenium with an effective chlorine concentration of 4.0 wt % was obtained by the same method as in Reference Example 5-1. 1 L of the obtained treatment liquid was poured over the surface of a 300 mm Si wafer deposited with a 1360 Å-thick ruthenium film over 10 min at 25° C., followed by rinsing with 1 L of ultrapure water, and the liquids were collected in a waste fluid tank to yield a ruthenium-containing waste fluid described in Table 16 containing $6.0 \times 10^{-4}$ mol/L of Ru.

TABLE 15

| | Composition of treatment agent for ruthenium-containing waste fluid | | | Ru concentration in mixed liquid of treatment agent for Ru-containing waste fluid | Treatment method for | Ru content in $RuO_4$ gas |
|---|---|---|---|---|---|---|
| | Oxidizing agent | Onium salt | pH | and waste fluid [mol/L] | wafer | [μg/cm²] |
| Experimental Example 5-1 | 2.0 mass % NaClO aqueous solution | n-Octyltrimethylammonium chloride (33.2 mass %) | 7 | $6.0 \times 10^{-4}$ | Immersion | 3 |
| Experimental Example 5-2 | 2.0 mass % NaClO aqueous solution | n-Octyltrimethylammonium chloride (33.2 mass %) | 9 | $6.0 \times 10^{-4}$ | Immersion | 1 |
| Experimental Example 5-3 | 2.0 mass % NaClO aqueous solution | n-Octyltrimethylammonium chloride (33.2 mass %) | 12 | $6.0 \times 10^{-4}$ | Immersion | 0 |
| Experimental Example 5-4 | 2.0 mass % NaClO aqueous solution | n-Octyltrimethylammonium chloride (33.2 mass %) | 13 | $6.0 \times 10^{-4}$ | Immersion | 0 |
| Experimental Example 5-5 | 2.0 mass % NaClO aqueous solution | Tetrapropylammonium hydroxide (17.6 mass %) | 12 | $6.0 \times 10^{-4}$ | Immersion | 3 |
| Experimental Example 5-6 | 2.0 mass % NaClO aqueous solution | Tetrabutylammonium hydroxide (30 mass %) | 12 | $6.0 \times 10^{-4}$ | Immersion | 2 |
| Experimental Example 5-7 | 2.0 mass % NaClO aqueous solution | Triphenylsulfonium chloride (3.4 mass %) | 12 | $6.0 \times 10^{-4}$ | Immersion | 1 |
| Experimental Example 5-8 | 2.0 mass % NaClO aqueous solution | Butyltriphenylphosphonium chloride (0.2 mass %) | 12 | $6.0 \times 10^{-4}$ | Immersion | 2 |

TABLE 15-continued

| | Composition of treatment agent for ruthenium-containing waste fluid | | | Ru concentration in mixed liquid of treatment agent for Ru-containing waste fluid and waste fluid [mol/L] | Treatment method for wafer | Ru content in RuO$_4$ gas [μg/cm$^2$] |
|---|---|---|---|---|---|---|
| | Oxidizing agent | Onium salt | pH | | | |
| Experimental Example 5-9 | 2.0 mass % NaClO aqueous solution | 1-Butyl-1-methyl-pyrrolidinium chloride (3.6 mass %) | 12 | 6.0 × 10$^{-4}$ | Immersion | 5 |
| Experimental Example 5-10 | 2.0 mass % NaClO aqueous solution | 5-Azoniaspiro[4.4]nonane chloride (3.4 mass %) | 12 | 6.0 × 10$^{-4}$ | Immersion | 6 |
| Experimental Example 5-11 | 2.0 mass % NaClO aqueous solution | Hexamethonium chloride (25.7 mass %) | 12 | 6.0 × 10$^{-4}$ | Immersion | 2 |
| Experimental Example 5-12 | — | n-Octyltrimethylammonium chloride (33.2 mass %) | 12 | 6.0 × 10$^{-4}$ | Immersion | 0 |
| Experimental Example 5-13 | 2.0 mass % NaClO aqueous solution | n-Octyltrimethylammonium chloride (33.2 mass %) | 12 | 6.0 × 10$^{-4}$ | Single wafer | 0 |
| Experimental Example 5-14 | 2.0 mass % NaClO aqueous solution | 5-Azoniaspiro[4.4]nonane chloride (3.4 mass %) | 12 | 6.0 × 10$^{-4}$ | Single wafer | 5 |
| Experimental Example 5-15 | 2.0 mass % NaClO aqueous solution | Hexamethonium chloride (25.7 mass %) | 12 | 6.0 × 10$^{-4}$ | Single wafer | 1 |

TABLE 16

| | Composition of treatment solution for etching ruthenium | | | Ru concentration in Ru-containing waste fluid [mol/L] | Treatment method for wafer | Ru content in RuO$_4$ gas [μg/cm$^2$] |
|---|---|---|---|---|---|---|
| | Oxidizing agent | Onium salt | pH | | | |
| Reference Example 5-1 | 2.0 mass % NaClO aqueous solution | — | 7 | 6.0 × 10$^{-4}$ | Immersion | 59 |
| Reference Example 5-2 | 2.0 mass % NaClO aqueous solution | — | 9 | 6.0 × 10$^{-4}$ | Immersion | 37 |
| Reference Example 5-3 | 2.0 mass % NaClO aqueous solution | — | 12 | 6.0 × 10$^{-4}$ | Immersion | 19 |
| Reference Example 5-4 | 2.0 mass % NaClO aqueous solution | — | 12 | 6.0 × 10$^{-4}$ | Single wafer | 18 |

From the results shown in Tables 15 and 16, it was found that ruthenium-containing gas generation was inhibited when a treatment liquid containing any of the onium salts expressed by Formulas (2) to (5) was added to a ruthenium-containing waste fluid. From this it was known that the treatment liquid of each aspect of the present invention can be suitably used for treating a ruthenium-containing waste fluid, because it inhibits ruthenium-containing gas generation when it is used for treating a ruthenium-containing waste fluid.

REFERENCE SIGNS LIST

1 Substrate
2 Interlayer insulating film
3 Ruthenium

The invention claimed is:

1. A treatment liquid for a semiconductor wafer, comprising an onium salt composed of an onium ion and an anion, wherein the treatment liquid has a pH at 25° C. of more than 7 and less than 14.

2. The treatment liquid for a semiconductor wafer according to claim 1, which is used for etching a metal contained in a semiconductor wafer, wherein the treatment liquid is used in a process for forming the semiconductor wafer comprising:
(A) a hypochlorite ion
(B) an alkylammonium salt expressed by the following Formula (1)

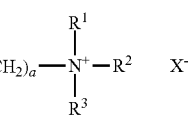

(1)

wherein in Formula (1), "a" is an integer from 6 to 20; R$^1$, R$^2$, and R$^3$ are independently a hydrogen atom, or an alkyl group with a carbon number from 1 to 20; and X$^-$ is a fluoride ion, a chloride ion, an iodide ion, a hydroxide ion, a nitrate ion, a phosphate ion, a sulfate ion, a hydrogen sulfate ion, a methanesulfate ion, a perchlorate ion, an acetate ion, a fluoroborate ion, or a trifluoroacetate ion.

3. The treatment liquid according to claim 2, wherein the concentration of the alkylammonium salt (B) expressed by Formula (1) is from 0.0001 to 10 mass %.

4. The treatment liquid according to claim 2, comprising at least one kind of ammonium ion (C) selected from a tetramethylammonium ion, a tetraethylammonium ion, a tetrapropylammonium ion, and a tetrabutylammonium ion.

5. The treatment liquid according to claim 2, wherein the metal contained in the semiconductor wafer is ruthenium.

6. An etching method comprising a step of bringing a semiconductor wafer into contact with the treatment liquid according to claim 2.

7. The treatment liquid for a semiconductor wafer according to claim 1, comprising an onium salt consisting of an onium ion and an anion, wherein the onium salt is a quaternary onium salt expressed by Formula (2), or a tertiary onium salt expressed by Formula (3)

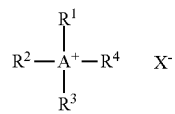
(2)

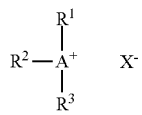
(3)

wherein in Formula (2), A⁺ is an ammonium ion, or a phosphonium ion; and R¹, R², R³, and R⁴ are independently an alkyl group with a carbon number from 1 to 25, an allyl group, an aralkyl group having an alkyl group with a carbon number from 1 to 25, or an aryl group; when R¹, R², R³, and R⁴ are alkyl groups, at least one of the alkyl groups in R¹, R², R³, and R⁴ has a carbon number of 2 or more; wherein at least one hydrogen in a ring of an aryl group in the aralkyl group, and the aryl group may be replaced with fluorine, chlorine, an alkyl group with a carbon number from 1 to 10, an alkenyl group with a carbon number from 2 to 10, an alkoxy group with a carbon number from 1 to 9, or an alkenyloxy group with a carbon number from 2 to 9; and in these groups, at least one hydrogen may be replaced with fluorine or chlorine;

wherein in Formula (3), A⁺ is a sulfonium ion; and R¹, R², and R³ are independently an alkyl group with a carbon number from 1 to 25, an allyl group, an aralkyl group having an alkyl group with a carbon number from 1 to 25, or an aryl group; when R¹, R², and R³ are alkyl groups, at least one of the alkyl groups in R¹, R², and R³ has a carbon number of 2 or more;

wherein at least one hydrogen in a ring of an aryl group in the aralkyl group, or the aryl group may be replaced with fluorine, chlorine, an alkyl group with a carbon number from 1 to 10, an alkenyl group with a carbon number from 2 to 10, an alkoxy group with a carbon number from 1 to 9, or an alkenyloxy group with a carbon number from 2 to 9; and in these groups, at least one hydrogen may be replaced with fluorine or chlorine; and wherein in Formula (2) or (3), X⁻ is a fluoride ion, a chloride ion, an iodide ion, a hydroxide ion, a nitrate ion, a phosphate ion, a sulfate ion, a hydrogen sulfate ion, a methanesulfate ion, a perchlorate ion, a chlorate ion, a chlorite ion, a hypochlorite ion, an orthoperiodate ion, a metaperiodate ion, an iodate ion, an iodite ion, a hypoiodite ion, an acetate ion, a carbonate ion, a hydrogencarbonate ion, a fluoroborate ion, or a trifluoroacetate ion.

8. The treatment liquid according to claim 7, wherein the quaternary onium salt is a salt comprising at least one ammonium ion selected from a tetrapropylammonium ion, a tetrabutylammonium ion, or a tetrapentylammonium ion.

9. The treatment liquid for a semiconductor wafer according to claim 1, comprising an onium salt consisting of an onium ion and an anion, wherein the onium salt is an onium salt expressed by Formula (4)

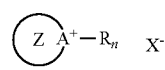
(4)

wherein in Formula (4), Z is an aromatic group or an alicyclic group that may contain a nitrogen, sulfur, or oxygen atom, and in the aromatic group or alicyclic group, the carbon or nitrogen may have:
chlorine, bromine, fluorine, iodine,
at least one alkyl group with a carbon number from 1 to 15,
at least one alkenyloxy group with a carbon number from 2 to 9,
an aromatic group that may be substituted with at least one alkyl group with a carbon number from 1 to 15, or
an alicyclic group that may be substituted with at least one alkyl group with a carbon number from 1 to 15;
A is nitrogen or sulfur;
R is chlorine, bromine, fluorine, iodine, an alkyl group with a carbon number from 1 to 15, an allyl group, an aromatic group that may be substituted with at least one alkyl group with a carbon number from 1 to 15, or an alicyclic group that may be substituted with at least one alkyl group with a carbon number from 1 to 15;
X⁻ is an organic or inorganic anion; and
n is an integer of 1 or 2 and indicates the number of R, wherein when n is 2, R may be the same or different, and may form a ring.

10. The treatment liquid according to claim 9, wherein the onium salt is an imidazolium salt, a pyrrolidinium salt, a pyridinium salt, an oxazolium salt, or a piperidinium salt.

11. The treatment liquid according to claim 9, wherein the organic or inorganic anion is a fluoride ion, a chloride ion, an iodide ion, a hydroxide ion, a nitrate ion, a phosphate ion, a sulfate ion, a hydrogen sulfate ion, a methanesulfate ion, a perchlorate ion, a chlorate ion, a chlorite ion, a hypochlorite ion, an orthoperiodate ion, a metaperiodate ion, an iodate ion, an iodite ion, a hypoiodite ion, an acetate ion, a carbonate ion, a hydrogencarbonate ion, a fluoroborate ion, a fluorophosphate ion, or a trifluoroacetate ion.

12. The treatment liquid for a semiconductor wafer according to claim 1, comprising an onium salt consisting of an onium ion and an anion, wherein the onium salt is an onium salt expressed by Formula (5)

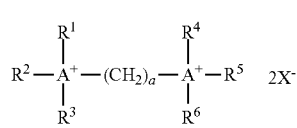
(5)

wherein in Formula (5), A⁺ are independently an ammonium ion, or a phosphonium ion; and R¹, R², R³, R⁴, R⁵, and R⁶ are independently an alkyl group with a carbon number from 1 to 25, an allyl group, an aralkyl group having an alkyl group with a carbon number from 1 to 25, or an aryl group; wherein at least one hydrogen in a ring of an aryl group in the aralkyl group, or the aryl group may be replaced with fluorine, chlorine, an alkyl group with a carbon number from 1 to 10, an alkenyl group with a carbon number from 2 to 10, an alkoxy group with a carbon number from 1 to 9, or an alkenyloxy group with a carbon number from 2 to 9; and in these groups, at least one hydrogen may be replaced with fluorine or chlorine; and wherein in Formula (5), $X^-$ is a fluoride ion, a chloride ion, an iodide ion, a hydroxide ion, a nitrate ion, a phosphate ion, a sulfate ion, a hydrogen sulfate ion, a methanesulfate ion, a perchlorate ion, a chlorate ion, a chlorite ion, a hypochlorite ion, an orthoperiodate ion, a metaperiodate ion, an iodate ion, an iodite ion, a hypoiodite ion, an acetate ion, a carbonate ion, a hydrogencarbonate ion, a fluoroborate ion, or a trifluoroacetate ion; and a is an integer of 1 to 10.

13. The treatment liquid according to claim 1, wherein the concentration of the onium salt in the treatment liquid is from 0.0001 to 50 mass %.

14. The treatment liquid according to claim 13, wherein the treatment liquid comprises an oxidizing agent.

15. The treatment liquid according to claim 13, wherein the treatment liquid comprises hypochlorite ions and the concentration of hypochlorite ions is from 0.05 to 20.0 mass %.

16. The treatment liquid according to claim 13, further comprising an organic solvent.

17. The treatment liquid according to claim 16, wherein the relative dielectric constant of the organic solvent is 45 or less.

18. The treatment liquid according to claim 16, wherein the organic solvent is a sulfolane, an alkyl nitrile, a halogenated alkane, or an ether.

19. A method for etching a semiconductor wafer comprising a step of bringing a semiconductor wafer containing ruthenium into contact with the treatment liquid according to claim 13.

* * * * *